United States Patent
Raimondi

(10) Patent No.: US 11,951,108 B2
(45) Date of Patent: Apr. 9, 2024

(54) COMBINATION THERAPY FOR TREATING CANCER

(71) Applicant: Epizyme, Inc., Cambridge, MA (US)

(72) Inventor: Maria Alejandra Raimondi, Jamaica Plain, MA (US)

(73) Assignee: EPIZYME, INC., Cambridge, MA (US)

( * ) Notice: Subject to any disclaimer, the term of this patent is extended or adjusted under 35 U.S.C. 154(b) by 0 days.

(21) Appl. No.: 16/073,558

(22) PCT Filed: Jan. 27, 2017

(86) PCT No.: PCT/US2017/015352
§ 371 (c)(1),
(2) Date: Jul. 27, 2018

(87) PCT Pub. No.: WO2017/132518
PCT Pub. Date: Aug. 3, 2017

(65) Prior Publication Data
US 2019/0151325 A1  May 23, 2019

Related U.S. Application Data

(60) Provisional application No. 62/289,050, filed on Jan. 29, 2016.

(51) Int. Cl.
| | | |
|---|---|---|
| *A61K 31/5377* | (2006.01) | |
| *A61K 31/138* | (2006.01) | |
| *A61K 31/166* | (2006.01) | |
| *A61K 31/167* | (2006.01) | |
| *A61K 31/282* | (2006.01) | |
| *A61K 31/337* | (2006.01) | |
| *A61K 31/4045* | (2006.01) | |
| *A61K 31/4196* | (2006.01) | |
| *A61K 31/436* | (2006.01) | |
| *A61K 31/437* | (2006.01) | |
| *A61K 31/4375* | (2006.01) | |
| *A61K 31/4406* | (2006.01) | |
| *A61K 31/4439* | (2006.01) | |
| *A61K 31/4545* | (2006.01) | |
| *A61K 31/4745* | (2006.01) | |

(Continued)

(52) U.S. Cl.
CPC ........ *A61K 31/5377* (2013.01); *A61K 31/138* (2013.01); *A61K 31/166* (2013.01); *A61K 31/167* (2013.01); *A61K 31/282* (2013.01); *A61K 31/337* (2013.01); *A61K 31/4045* (2013.01); *A61K 31/4196* (2013.01); *A61K 31/436* (2013.01); *A61K 31/437* (2013.01); *A61K 31/4375* (2013.01); *A61K 31/4406* (2013.01); *A61K 31/4439* (2013.01); *A61K 31/4545* (2013.01); *A61K 31/4745* (2013.01); *A61K 31/502* (2013.01); *A61K 31/506* (2013.01); *A61K 31/517* (2013.01); *A61K 31/519* (2013.01); *A61K 31/52* (2013.01); *A61K 31/551* (2013.01); *A61K 31/555* (2013.01); *A61K 31/567* (2013.01); *A61K 31/575* (2013.01); *A61K 31/635* (2013.01); *A61K 31/675* (2013.01); *A61K 31/704* (2013.01); *A61K 31/7048* (2013.01); *A61K 31/706* (2013.01); *A61K 31/7068* (2013.01); *A61K 33/243* (2019.01); *A61K 45/06* (2013.01); *A61P 35/00* (2018.01)

(58) Field of Classification Search
CPC .............. A61K 2300/00; A61K 31/138; A61K 31/166; A61K 31/167; A61K 31/4045; A61K 31/4196; A61K 31/436; A61K 31/437; A61K 31/4375; A61K 31/4406; A61K 31/4439; A61K 31/4545; A61K 31/4745; A61K 31/502; A61K 31/517; A61K 31/519; A61K 31/52; A61K 31/5377; A61K 31/551; A61K 31/555; A61K 31/567; A61K 31/575; A61K 31/635; A61K 31/675; A61K 31/7048; A61K 31/7068; A61K 33/24; A61K 31/282; A61K 31/337; A61K 31/506; A61K 31/704; A61K 31/706; A61K 33/243; A61K 45/06; A61P 35/00
USPC .................................................. 514/449, 49
See application file for complete search history.

(56) References Cited

U.S. PATENT DOCUMENTS

| | | |
|---|---|---|
| 8,410,888 B2 | 4/2013 | Kuntz et al. |
| 8,536,179 B2 | 9/2013 | Miller et al. |

(Continued)

FOREIGN PATENT DOCUMENTS

| | | |
|---|---|---|
| WO | WO 2011/140324 A1 | 11/2011 |
| WO | WO 2012/034132 A2 | 3/2012 |

(Continued)

OTHER PUBLICATIONS

Weil et al.(Curr Probl Cancer. Jan.-Feb. 2011; 35(1): 7-50.doi: 10.1016/j.currproblcancer.2010.12.002,).*

(Continued)

*Primary Examiner* — Sahar Javanmard
(74) *Attorney, Agent, or Firm* — Dechert LLP; Danielle M. Paglia; Nicholas J. Pace

(57) ABSTRACT

The disclosure relates to a method for treatment of cancer comprising administering to a subject in need thereof a first agent in a therapeutically effective amount and a second agent in a therapeutically effective amount. Preferably, the first agent comprises an EZH2 inhibitor, e.g., tazemetostat or a pharmaceutically acceptable salt thereof. In certain embodiments, the methods of the disclosure are used to treat breast cancer, ovarian cancer, or both.

20 Claims, 2 Drawing Sheets

(51) Int. Cl.

| | | |
|---|---|---|
| *A61K 31/502* | (2006.01) | |
| *A61K 31/506* | (2006.01) | |
| *A61K 31/517* | (2006.01) | |
| *A61K 31/519* | (2006.01) | |
| *A61K 31/52* | (2006.01) | |
| *A61K 31/551* | (2006.01) | |
| *A61K 31/555* | (2006.01) | |
| *A61K 31/567* | (2006.01) | |
| *A61K 31/575* | (2006.01) | |
| *A61K 31/635* | (2006.01) | |
| *A61K 31/675* | (2006.01) | |
| *A61K 31/704* | (2006.01) | |
| *A61K 31/7048* | (2006.01) | |
| *A61K 31/706* | (2006.01) | |
| *A61K 31/7068* | (2006.01) | |
| *A61K 33/243* | (2019.01) | |
| *A61K 45/06* | (2006.01) | |
| *A61P 35/00* | (2006.01) | |

(56) References Cited

U.S. PATENT DOCUMENTS

| | | | |
|---|---|---|---|
| 8,765,732 B2 | 7/2014 | Kuntz et al. | |
| 8,895,245 B2 | 11/2014 | Copeland et al. | |
| 9,090,562 B2 | 7/2015 | Kuntz et al. | |
| 9,446,064 B2 * | 9/2016 | Klaus | A61K 31/7076 |
| 9,469,646 B2 | 10/2016 | Albrecht et al. | |
| 9,688,665 B2 * | 6/2017 | Knutson | A61K 31/5377 |
| 2003/0175736 A1 | 9/2003 | Chinnaiyan et al. | |
| 2011/0064664 A1 * | 3/2011 | Lopez-Berestein | A61K 45/06 424/9.1 |
| 2012/0264734 A1 * | 10/2012 | Kuntz | A61K 31/4433 514/210.18 |
| 2013/0040906 A1 * | 2/2013 | Kuntz | C12Q 1/48 514/46 |
| 2014/0107122 A1 * | 4/2014 | Kuntz | A61P 35/00 514/235.5 |
| 2014/0128393 A1 | 5/2014 | Knutson et al. | |
| 2014/0323421 A1 * | 10/2014 | Klaus | A61K 31/7076 514/34 |
| 2015/0099747 A1 * | 4/2015 | Ma | A61K 31/496 514/235.5 |
| 2015/0368229 A1 * | 12/2015 | Albrecht | C07D 401/12 514/275 |
| 2016/0045531 A1 * | 2/2016 | Klaus | A61K 31/704 514/34 |
| 2017/0080010 A1 * | 3/2017 | Klaus | A61K 31/7076 |
| 2017/0232030 A1 * | 8/2017 | Klaus | A61K 45/06 424/649 |

FOREIGN PATENT DOCUMENTS

| | | |
|---|---|---|
| WO | WO 2012/118812 A2 | 9/2012 |
| WO | WO 2012/142504 A1 | 10/2012 |
| WO | WO 2012/142513 A1 | 10/2012 |
| WO | WO 2013/120104 A2 | 8/2013 |
| WO | WO 2013/155317 A1 | 10/2013 |
| WO | WO 2013/155464 A1 | 10/2013 |
| WO | WO 2014/062720 A2 | 4/2014 |
| WO | WO 2014/062732 A1 | 4/2014 |
| WO | WO 2014/062733 A2 | 4/2014 |
| WO | WO 2014/100646 A1 | 6/2014 |
| WO | WO 2014/100665 A1 | 6/2014 |
| WO | WO 2014/124418 A1 | 8/2014 |
| WO | WO 2014/144747 A1 | 9/2014 |
| WO | WO 2014/153030 A2 | 9/2014 |
| WO | WO 2014/172044 A1 | 10/2014 |
| WO | WO 2015/010049 A1 | 1/2015 |
| WO | WO 2015/010078 A2 | 1/2015 |
| WO | WO 2015/057859 A1 | 4/2015 |
| WO | WO 2015/058125 A1 | 4/2015 |
| WO | WO 2015/085325 A1 | 6/2015 |
| WO | WO 2015/128837 A1 | 9/2015 |
| WO | WO 2015/143012 A1 | 9/2015 |
| WO | WO 2015/193768 A1 | 12/2015 |
| WO | WO 2015/195848 A1 | 12/2015 |
| WO | WO 2015/200650 A9 | 12/2015 |
| WO | WO 2016/061507 A1 | 4/2016 |
| WO | WO 2016/081523 A1 | 5/2016 |
| WO | WO 2016/172199 A1 | 10/2016 |
| WO | WO 2016/201328 A1 | 12/2016 |
| WO | WO 2017/035234 A1 | 3/2017 |
| WO | WO 2017/053930 A2 | 3/2017 |
| WO | WO 2017/062495 A2 | 4/2017 |
| WO | WO 2017/079757 A1 | 5/2017 |
| WO | WO 2017/100362 A2 | 6/2017 |

OTHER PUBLICATIONS

Panagiotis A. Konstantinopoulos et al. vol. 133, Issue 3, Jun. 2014, pp. 599-606, Gynecologic Oncology; Suberoylanilide hydroxamic acid (SAHA) enhances olaparib activity by targeting homologous recombination DNA repair in ovarian cancer).*

Hu, S. et al. (Oct. 15, 2010) "Overexpression of EZH2 contributes to acquired cisplatin resistance in ovarian cancer cells in vitro and in vivo", Cancer Biology & Therapy, vol. 10, No. 8, pp. 788-795.

McGuire III, W.P. et al. (Dec. 1, 2003) "Primary ovarian cancer chemotherapy: current standards of care", British Journal of Cancer, vol. 89, Suppl. 3, pp. S3-S8.

Peng, Dongjun et al. (Nov. 12, 2015) "Epigenetic silencing of TH1-type chemokines shapes tumour immunity and immunotherapy", Nature, vol. 527, No. 7577, pp. 249-253, including "Methods" and "Extended Data", 11 pages.

Chen, H. et al. (1996) "Cloning of a Human Homolog of the *Drosophila* Enhancer of zeste Gene (EZH2) That Maps to Chromosome 21q22.2" *Genomics*, 38:30-37.

Fiskus et al. (2009) "Combined epigenetic therapy with the histone methyltransferase EZH2 inhibitor 3-deazaneplanocin A and the histone deacetylase inhibitor panobinostat against human AML cells" *Blood*, 114(13):2733-2743.

Garapaty-Rao, S. et al. (Nov. 2013) "Identification of EZH2 and EZH1 Small Molecule Inhibitors with Selective Impact on Diffuse Large B Cell Lymphoma Cell Growth" *Chem Biol*, 20:1329-1339.

Genbank Accession No. CAB02546 (Apr. 18, 2005) "histone H3 [*Homo sapiens*]" National Center for Biotechnology Information (NCBI) [online]. Retrieved from: http://www.ncbi.nlm.nih.gov/protein/CAB02546; retreived on Jul. 23, 2012, 2 pages.

Genbank Accession No. NM_004456 (Jun. 26, 2012) "*Homo sapiens* enhancer of zeste homolog 2 (*Drosophila*) (EZH2), transcript variant 1, mRNA" National Center for Biotechnology Information (NCBI) [online]. Retrieved from: http://www.ncbi.nlm.nih.gov/nuccore/NM_04456; retreived on Jul. 23, 2012, 6 pages.

Genbank Accession No. NM_152998 (Jun. 26, 2012) "*Homo sapiens* enhancer of zeste homolog 2 (*Drosophila*) (EZH2), transcript variant 2, mRNA" National Center for Biotechnology Information (NCBI) [online]. Retrieved from: http://www.ncbi.nlm.nih.gov/nuccore/NM_152998; retreived on Jul. 23, 2012, 5 pages.

Genbank Accession No. NM_004447 (Jun. 26, 2012) "*Homo sapiens* epidermal growth factor receptor pathway substrate 8 (EPS8), mRNA" National Center for Biotechnology Information (NCBI) [online]. Retrieved from: http://www.ncbi.nlm.nih.gov/nuccore/NM_004447; retreived on Jul. 23, 2012, 5 pages.

Genbank Accession No. NP_694543 (Jun. 26, 2012) "histone-lysine N-methyltransferase EZH2 isoform b [*Homo sapiens*]" National Center for Biotechnology Information (NCBI) [online]. Retrieved from: http://www.ncbi.nlm.nih.gov/protein/NP_694543; retreived on Jul. 23, 2012, 3 pages.

Helming, K.C. et al. (Sep. 8, 2014) "Vulnerabilities of mutant SWI/SNF complexes in cancer" *Cancer Cell*, 26:309-317.

Jelinic, P. et al. (2014) "Recurrent SMARCA4 mutations in small cell carcinoma of the ovary" *Nat Genet*, 46:424-426. HHS Public Access Author Manuscript, retrieved from the Internet: https://www.ncbi.nlm.nih.gov/pmc/articles/PMC5699446/pdf/nihms920036.pdf, 10 pages.

(56) References Cited

OTHER PUBLICATIONS

Karnezis, A.N. et al. (2016) "Dual loss of the SWI/SNF complex ATPases SMARCA4/BRG1 and SMARCA2/BRM is highly sensitive and specific for small cell carcinoma of the ovary, hypercalcaemic type" *J Pathol*, 238:389-400.

Kleer, C.G. et al. (Sep. 3, 20030) "EZH2 is a marker of aggressive breast cancer and promotes neoplastic transformation of breast epithelial cells" *Proc Natl Acad Sci USA*, 100(20):11606-11611.

Knutson, S.K. et al. (Nov. 2012.) "A Selective Inhibitor of EZH2 Blocks H3K27 Methylation and Kills Mutant Lymphoma Cells" *Nat Chem Biol*, 8:890-896.

Knutson, S.K. et al. (May 7, 2013) "Durable tumor regression in genetically altered malignant rhabdoid tumors by inhibition of methyltransferase EZH2" *PNAS*, 110(19):7922-7927.

Kupryjanczyk, J. et al. (2013) "Ovarian small cell carcinoma of hypercalcemic type—evidence of germline origin and SMARCA4 gene inactivation. A pilot study" *Pol J Pathol*, 64:238-246.

Qi, W. et al. (2012) "Selective inhibition of Ezh2 by a small molecule inhibitor blocks tumor cells proliferation" *Proc Natl Acad Sci USA*, vol. 109, No. 52, pp. 21360-21365.

Ramos, P. et al. (2014) "Small cell carcinoma of the ovary, hypercalcemic type, displays frequent inactivating germline and somatic mutations in SMARCA4" *Nat Genet*, 46: 427-429. NIH Public Access Author Manuscript, retrieved from the Internet: https://www.ncbi.nlm.nih.gov/pmc/articles/PMC4332808/, 9 pages.

UNIPROTKB/SWISS-PROT Accession No. Q15910 (Mar. 21, 2012) "EZH2 Human" [online]. Retrieved from the Internet: http://www.uniprot.org/uniprot/Q15910.txt?version=113; retrieved on Jul. 23, 2012, 10 pages.

Varambally, S. et al. (2002) "The Polycomb Group Protein EZH2 Is Involved in Progression of Prostate Cancer" *Nature*, 419:624-629.

Witkowski, L. et al. (May 2014) "Germline and somatic SMARCA4 mutations characterize small cell carcinoma of the ovary, hypercalcemic type" *Nat Genet*, 46(5):438-443.

Dietrich, C.S. et al. (Jan. 1, 2010) "Suberoylanilide hydroxamic acid (SAHA) potentiates paclitaxel-induced apoptosis in ovarian cancer cell lines" *Gynecologic Oncology*, 116(1):126-130.

Gharpure, K.M. et al. (Jul. 1, 2014) "Metronomic Docetaxel in PRINT Nanoparticles and EZH2 Silencing Have Syntergistic Antitumor Effect in Ovarian Cancer" *Molecular Cancer Therapeutics*, 13(7):1750-1757.

Hibino, S. et al. (May 1, 2014) "Inhibitors of enhancer of zeste homolog 2 (EZH2) activate tumor-suppressor microRNAs in human cancer cells" *Oncogenesis*, 3(5):e104, 10 pages.

Konstantinopoulos, P.A. et al. (Jun. 1, 2014) "Suberoylanilide hydroxamic acid (SAHA) enhances olaparib activity by targeting homologous recombination DNA repair in ovarian cancer" *Gynecologic Oncology*, 133(3):599-606.

\* cited by examiner

COMBINATION THERAPY FOR TREATING CANCER

RELATED APPLICATIONS

This application is a U.S. National Phase application, filed under 35 U.S.C. § 371, of International Application No. PCT/US2017/015352, filed on Jan. 27, 2017, which claims the benefit of and priority to U.S. Provisional Application No. 62/289,050, filed Jan. 29, 2016, the contents of each of which are hereby incorporated by reference in their entireties.

FIELD OF THE DISCLOSURE

This disclosure relates to compositions comprising inhibitors of human histone methyltransferase EZH2, the catalytic subunit of the PRC2 complex which catalyzes the mono- through tri-methylation of lysine 27 on histone H3 (H3-K27), and one or more other therapeutic agents, particularly anticancer agents, and methods of combination therapy for treating cancer.

BACKGROUND

Combination-therapy treatments for cancer have become more common, in part due to the perceived advantage of attacking the disease via multiple avenues. Although many effective combination-therapy treatments have been identified over the past few decades; in view of the continuing high number of deaths each year resulting from cancer, a continuing need exists to identify effective therapeutic regimens for use in anticancer treatment.

SUMMARY

The disclosure is based upon the discovery that EZH2 histone methyltransferase inhibitors and other anti-cancer agents can be used in combination to treat certain tumors with superior results than those achieved by treating tumors with EZH2 histone methyltransferase inhibitors and the anti-cancer agents alone. Accordingly, the disclosure provides a composition comprising an EZH2 histone methyltransferase inhibitor and one or more other therapeutic agents, and methods for their use to treat diseases the course of which can be influenced by modulating the methylation status of histones or other proteins, e.g., cancer. In certain preferred embodiments, the disclosure provides a composition comprising the EZH2 histone methyltransferase inhibitor tazemetostat and a second anti-cancer agent. In certain preferred embodiments, the disclosure provides a composition comprising the EZH2 histone methyltransferase inhibitor tazemetostat and a second anti-cancer agent for the treatment of breast and/or ovarian cancer.

The disclosure provides a method for treatment of cancer comprising administering to a subject in need thereof (a) a first agent in a therapeutically effective amount, wherein the first agent comprises an EZH2 inhibitor, and (b) a second agent in a therapeutically effective amount. In a further embodiment, the disclosure provides a method for treatment of cancer comprising administering to a subject in need thereof (a) a first agent in a therapeutically effective amount, wherein the first agent comprises tazemetostat or a pharmaceutically acceptable salt thereof, and (b) a second agent in a therapeutically effective amount. In certain to embodiments the first agent and/or the second agent may comprise a pharmaceutically-acceptable carrier. The pharmaceutically-acceptable carrier may be the same for the first and second agents or may be distinct between the first and second agents.

According to the methods of the disclosure, the therapeutically effective amount of the EZH2 inhibitor may be between about 100 mg to about 1600 mg, inclusive of the endpoints. In certain embodiments, the therapeutically effective amount of the EZH2 inhibitor may be about 100 mg, 200 mg, 400 mg, 800 mg, or about 1600 mg. In certain embodiments, the therapeutically effective amount of the EZH2 inhibitor may be about 800 mg.

According to the methods of the disclosure, the therapeutically effective amount of tazemetostat or a pharmaceutically acceptable salt thereof may be between about 100 mg to about 1600 mg, inclusive of the endpoints. In certain embodiments, the therapeutically effective amount of tazemetostat or a pharmaceutically acceptable salt thereof may be about 100 mg, 200 mg, 400 mg, 800 mg, or about 1600 mg. In certain embodiments, the therapeutically effective amount of tazemetostat or a pharmaceutically acceptable salt thereof may be about 800 mg.

According to the methods of the disclosure, the therapeutically effective amount of the EZH2 inhibitor may be administered twice per day (BID).

According to the methods of the disclosure, the therapeutically effective amount of tazemetostat or a pharmaceutically acceptable salt thereof may be administered twice per day (BID).

According to the methods of the disclosure, the therapeutically effective amount of the EZH2 inhibitor may be administered orally. For example, the therapeutically effective amount of tazemetostat or a pharmaceutically acceptable salt thereof may be administered as a capsule or tablet.

According to the methods of the disclosure, the therapeutically effective amount of tazemetostat or a pharmaceutically acceptable salt thereof may be administered orally. For example, the therapeutically effective amount of tazemetostat or a pharmaceutically acceptable salt thereof may be administered as a capsule or tablet.

Methods of the disclosure may include treating ovarian cancer, breast cancer, or both.

In certain embodiments of the methods of the disclosure, and particularly those embodiments in which the cancer is ovarian cancer, the second agent may form a DNA adduct. Exemplary second agents that may form a DNA adduct include, but are not limited to, carboplatin and cisplatin.

In certain embodiments of the methods of the disclosure, and particularly those embodiments in which the cancer is ovarian cancer, the second agent may bind a microtubule. Exemplary second agents that may bind a microtubule include, but are not limited to, paclitaxel and docetaxel.

In certain embodiments of the methods of the disclosure, and particularly those embodiments in which the cancer is ovarian cancer, the second agent may be an antimetabolite. Exemplary second agents that may be an antimetabolite include, but are not limited to, gemcitabine. In certain aspects of these embodiments, the antimetabolite may not include methotrexate.

In certain embodiments of the methods of the disclosure, and particularly those embodiments in which the cancer is ovarian cancer, the second agent may intercalate DNA. Exemplary second agents that may intercalate DNA include, but are not limited to, topotecan and doxorubicin.

In certain embodiments of the methods of the disclosure, and particularly those embodiments in which the cancer is ovarian cancer, the second agent may be an alkylating agent.

Exemplary second agents that may be an alkylating agent include, but are not limited to, mafosfamide.

In certain embodiments of the methods of the disclosure, and particularly those embodiments in which the cancer is ovarian cancer, the second agent may be an AKT inhibitor. Exemplary second agents that may be an AKT inhibitor include, but are not limited to, MK2206 and AZD5363.

In certain embodiments of the methods of the disclosure, and particularly those embodiments in which the cancer is ovarian cancer, the second agent may be a BCL2 inhibitor. Exemplary second agents that may be a BCL2 inhibitor include, but are not limited to, ABT199.

In certain embodiments of the methods of the disclosure, and particularly those embodiments in which the cancer is ovarian cancer, the second agent may be a BRAF inhibitor. Exemplary second agents that may be a BRAF inhibitor include, but are not limited to, vemurafenib.

In certain embodiments of the methods of the disclosure, and particularly those embodiments in which the cancer is ovarian cancer, the second agent may be a bromodomain inhibitor. Exemplary second agents that may be a bromodomain inhibitor include, but are not limited to, JQ1.

In certain embodiments of the methods of the disclosure, and particularly those embodiments in which the cancer is ovarian cancer, the second agent may be a CHK1/2 inhibitor. Exemplary second agents that may be a CHK1/2 inhibitor include, but are not limited to, LY2606318.

In certain embodiments of the methods of the disclosure, and particularly those embodiments in which the cancer is ovarian cancer, the second agent may be a DNMT inhibitor. Exemplary second agents that may be a DNMT inhibitor include, but are not limited to, decitabine and azacitidine.

In certain embodiments of the methods of the disclosure, and particularly those embodiments in which the cancer is ovarian cancer, the second agent may be an EGFR inhibitor. Exemplary second agents that may be an EGFR inhibitor include, but are not limited to, erlotinib and lapatinib.

In certain embodiments of the methods of the disclosure, and particularly those embodiments in which the cancer is ovarian cancer, the second agent may be an EGFR inhibitor and an ERBB2 inhibitor. Exemplary second agents that may be an EGFR inhibitor and an ERBB2 inhibitor include, but are not limited to lapatinib.

In certain embodiments of the methods of the disclosure, and particularly those embodiments in which the cancer is ovarian cancer, the second agent may be an HDAC inhibitor. Exemplary second agents that may be an HDAC inhibitor include, but are not limited to, vorinostat, panobinostat, mocetinostat, entinostat and romidepsin.

In certain embodiments of the methods of the disclosure, and particularly those embodiments in which the cancer is ovarian cancer, the second agent may be a MEK1/2 inhibitor. Exemplary second agents that may be a MEK1/2 inhibitor include, but are not limited to, trametinib.

In certain embodiments of the methods of the disclosure, and particularly those embodiments in which the cancer is ovarian cancer, the second agent may be an mTOR inhibitor. Exemplary second agents that may be an mTOR inhibitor include, but are not limited to, rapamycin.

In certain embodiments of the methods of the disclosure, and particularly those embodiments in which the cancer is ovarian cancer, the second agent may be a pan AKT inhibitor. Exemplary second agents that may be a pan AKT inhibitor include, but are not limited to, GSK690693.

In certain embodiments of the methods of the disclosure, and particularly those embodiments in which the cancer is ovarian cancer, the second agent may be a PARP inhibitor.

Exemplary second agents that may be a PARP inhibitor include, but are not limited to, olaparib.

In certain embodiments of the methods of the disclosure, and particularly those embodiments in which the cancer is ovarian cancer, the second agent may be a PI3 Kinase inhibitor. Exemplary second agents that may be a PI3 Kinase inhibitor include, but are not limited to, BYL719, BKM120 and pictilisib.

In certain embodiments of the methods of the disclosure, and particularly those embodiments in which the cancer is ovarian cancer, the second agent may be a VEGF inhibitor. Exemplary second agents that may be a VEGF inhibitor include, but are not limited to, AZD2171.

In certain embodiments of the methods of the disclosure, and particularly those embodiments in which the cancer is ovarian cancer, the second agent may be a Wee1 inhibitor. Exemplary second agents that may be a Wee1 inhibitor include, but are not limited to, AXD2171.

In certain embodiments of the methods of the disclosure, and particularly those embodiments in which the cancer is breast cancer, the second agent may be a MEK inhibitor. Exemplary second agents that may be a MEK inhibitor include, but are not limited to, trametinib.

In certain embodiments of the methods of the disclosure, and particularly those embodiments in which the cancer is breast cancer, the second agent may be a SRC Kinase inhibitor. Exemplary second agents that may be a SRC Kinase inhibitor include, but are not limited to, a BCR and/or an ABL SRC kinase inhibitor. Exemplary second agents that may be a SRC Kinase inhibitor include, but are not limited to, dasatinib.

In certain embodiments of the methods of the disclosure, and particularly those embodiments in which the cancer is breast cancer, the second agent may be an Aurora A and VEGR dual inhibitor. Exemplary second agents that may be an Aurora A and VEGR dual inhibitor include, but are not limited to, ENMD-2076.

In certain embodiments of the methods of the disclosure, and particularly those embodiments in which the cancer is breast cancer, the second agent may be an mTOR inhibitor. Exemplary second agents that may be an mTOR inhibitor include, but are not limited to, everolimus.

In certain embodiments of the methods of the disclosure, and particularly those embodiments in which the cancer is breast cancer, the second agent may be a CDK inhibitor. Exemplary second agents that may be a CDK inhibitor include, but are not limited to, dinaciclib.

In certain embodiments of the methods of the disclosure, and particularly those embodiments in which the cancer is breast cancer, the second agent may be a microtubule inhibitor. Exemplary second agents that may be a microtubule inhibitor include, but are not limited to, paclitaxel.

In certain embodiments of the methods of the disclosure, and particularly those embodiments in which the cancer is breast cancer, the second agent may be an anthracycline topoisomerase inhibitor. Exemplary second agents that may be an anthracycline topoisomerase inhibitor include, but are not limited to, epirubicin.

In certain embodiments of the methods of the disclosure, and particularly those embodiments in which the cancer is breast cancer, the second agent may be an antiprogesterone and an antiglucocorticoid. Exemplary second agents that may be an antiprogesterone and an antiglucocorticoid include, but are not limited to, mifepristone.

In certain embodiments of the methods of the disclosure, and particularly those embodiments in which the cancer is breast cancer, the second agent may be a PARP inhibitor.

Exemplary second agents that may be a PARP inhibitor include, but are not limited to, iniparib and olaparib.

In certain embodiments of the methods of the disclosure, and particularly those embodiments in which the cancer is breast cancer, the second agent may be an AKT inhibitor. Exemplary second agents that may be an AKT inhibitor include, but are not limited to, MK2206.

In certain embodiments of the methods of the disclosure, and particularly those embodiments in which the cancer is breast cancer, the second agent may be an alkylating agent. Exemplary second agents that may be an alkylating agent include, but are not limited to, mafosfamide.

In certain embodiments of the methods of the disclosure, and particularly those embodiments in which the cancer is breast cancer, the second agent may be an estrogen agonist. Exemplary second agents that may be an estrogen agonist include, but are not limited to, tamoxifen citrate.

In certain embodiments of the methods of the disclosure, and particularly those embodiments in which the cancer is breast cancer, the second agent may be an aromatase inhibitor. Exemplary second agents that may be an aromatase inhibitor include, but are not limited to, anastozole and letrozole.

In certain embodiments of the methods of the disclosure, and particularly those embodiments in which the cancer is breast cancer, the second agent may be an EGFR inhibitor and an ERBB2/HER2 inhibitor. Exemplary second agents that may be an EGFR inhibitor and an ERBB2/HER2 inhibitor include, but are not limited to, lapatinib.

In certain embodiments of the methods of the disclosure, and particularly those embodiments in which the cancer is breast cancer, the second agent may induce hypomethylation. Exemplary second agents that may induce hypomethylation include, but are not limited to, azacitidine, decitabine and SGI1027.

In certain embodiments of the methods of the disclosure, and particularly those embodiments in which the cancer is breast cancer, the second agent may be a topoisomerase inhibitor. Exemplary second agents that may be a topoisomerase inhibitor include, but are not limited to, etoposide.

In certain embodiments of the methods of the disclosure, and particularly those embodiments in which the cancer is breast cancer, the second agent may be a nucleoside metabolic inhibitor. Exemplary second agents that may be a nucleoside metabolic inhibitor include, but are not limited to, gemcitabine.

In certain embodiments of the methods of the disclosure, and particularly those embodiments in which the cancer is breast cancer, the second agent may be a platinum-based DNA crosslinking agent. Exemplary second agents that may be a platinum-based DNA crosslinking agent include, but are not limited to, cisplatin.

In certain embodiments of the methods of the disclosure, and particularly those embodiments in which the cancer is breast cancer, the second agent may be a bromodomain inhibitor. Exemplary second agents that may be a bromodomain inhibitor include, but are not limited to, JQ1.

In certain embodiments of the methods of the disclosure, and particularly those embodiments in which the cancer is breast cancer, the second agent may be a PI3 Kinase and a p110α/β/δ/υ inhibitor. Exemplary second agents that may be a PI3 Kinase and p110α/β/δ/υ inhibitor include, but are not limited to, BKM120.

Second anti-cancer agents of the disclosure may be administered at a dosage of 0.01 mg/kg per day to about 1000 mg/kg per day.

According to the methods of the disclosure, the therapeutically effective amount of tazemetostat or a pharmaceutically acceptable salt thereof and the second agent may be administered simultaneously. Alternatively, the therapeutically effective amount of tazemetostat or a pharmaceutically acceptable salt thereof and the second agent may be administered sequentially. In certain embodiments, the tazemetostat or a pharmaceutically acceptable salt thereof may be administered prior to the second agent. In certain embodiments, the second agent may be administered prior to the tazemetostat or a pharmaceutically acceptable salt thereof.

In certain embodiments of the methods of the disclosure, the first agent may comprise an EZH2 inhibitor, e.g. a compound of Formula (VIa) below.

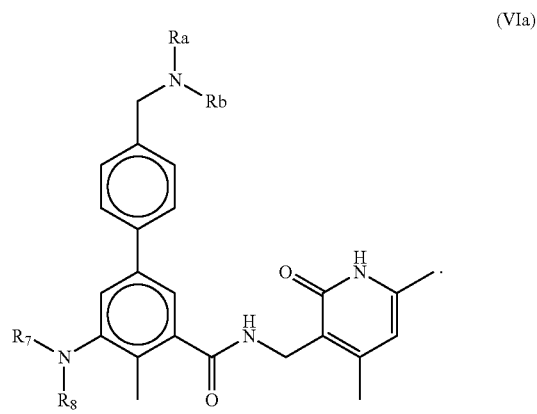

(VIa)

According to the methods of the disclosure, compounds of Formula (VIa) can include one or more of the following features:

Each of $R^a$ and $R^b$ independently is H or $C_1$-$C_6$ alkyl.

$R^a$ and $R_b$, together with the N atom to which they are attached, is a 4 to 7-membered heterocycloalkyl ring having 0 or 1 additional heteroatom, the $C_1$-$C_6$ alkyl and the 4 to 12-membered (e.g., 4 to 7-membered) heterocycloalkyl ring being optionally substituted with one or more -$Q_3$-$T_3$.

$Q_3$ is a bond or unsubstituted or substituted $C_1$-$C_3$ alkyl linker.

$T_3$ is H, halo, 4 to 7-membered heterocycloalkyl, $C_1$-$C_3$ alkyl, $OR_d$, $COOR_d$, —$S(O)_2R_d$, or —$NR_dR_e$, each of $R_d$ and $R_e$ independently being H or $C_1$-$C_6$ alkyl.

$R_7$ is $C_1$-$C_6$ alkyl, $C_3$-$C_8$ cycloalkyl or 4 to 12-membered (e.g., 4 to 7-membered) heterocycloalkyl, each optionally substituted with one or more -$Q_5$-$T_5$. For example, $R_7$ is not H.

$R_7$ is 4 to 7-membered heterocycloalkyl optionally substituted with one or more -$Q_5$-$T_5$.

$R_7$ is piperidinyl, tetrahydropyran, cyclopentyl, or cyclohexyl, each optionally substituted with one -$Q_5$-$T_5$.

$T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 12-membered (e.g., 4 to 7-membered) heterocycloalkyl.

$Q_5$ is a bond and $T_5$ is $C_1$-$C_6$ alkyl, $C_3$-$C_8$ cycloalkyl, or 4 to 12-membered (e.g., 4 to 7-membered) heterocycloalkyl.

$Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.

$Q_5$ is $C_1$-$C_3$ alkyl linker and $T_5$ is H or $C_6$-$C_{10}$ aryl.

$Q_5$ is $C_1$-$C_3$ alkyl linker and $T_5$ is $C_3$-$C_8$ cycloalkyl, 4 to 7-membered heterocycloalkyl, or $S(O)_qR_q$.

$R_7$ is cyclopentyl or cyclohexyl, each optionally substituted with one $-Q_5-T_5$.

$Q_5$ is NHC(O) and $T_5$ is $C_1-C_6$ alkyl or $C_1-C_6$ alkoxy.

$R_7$ is isopropyl.

Each of $R_2$ and $R_4$ independently is H or $C_1-C_6$ alkyl optionally substituted with amino, mono-$C_1-C_6$ alkylamino, di-$C_1-C_6$ alkylamino, or $C_6-C_{10}$ aryl.

$R_8$ is H, methyl, or ethyl.

$R_8$ is methyl.

$R_8$ is ethyl.

$R_8$ is 4 to 7-heterocycloalkyl, e.g., tetrahydropyran.

In certain preferred embodiments of the methods of the disclosure, the compound of Formula (VIa) is tazemetostat (also known as Compound 44, Compound A, EPZ-6438, and E7438) having the following formula:

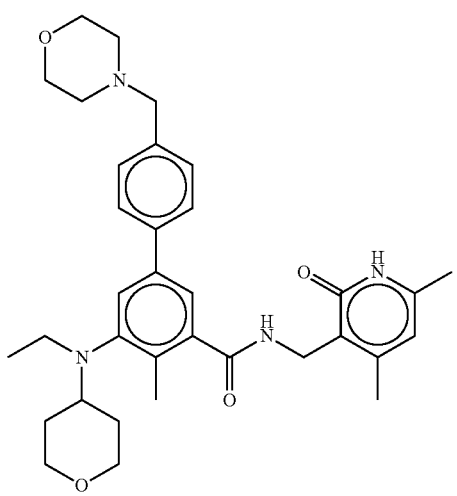

(A)

or a pharmaceutically acceptable salt or solvate thereof.

In certain embodiments of the methods of the disclosure, the EZH2 inhibitor is Compound B having the following formula:

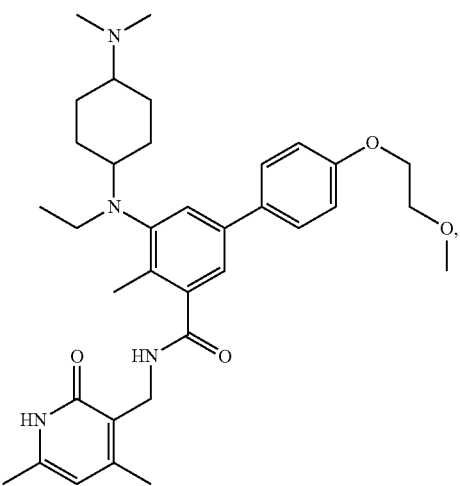

(B)

stereoisomers thereof, or pharmaceutically acceptable salts or solvates thereof.

In certain embodiments of the methods of the disclosure, the EZH2 inhibitor is Compound C (also known as EPZ011989) having the following formula:

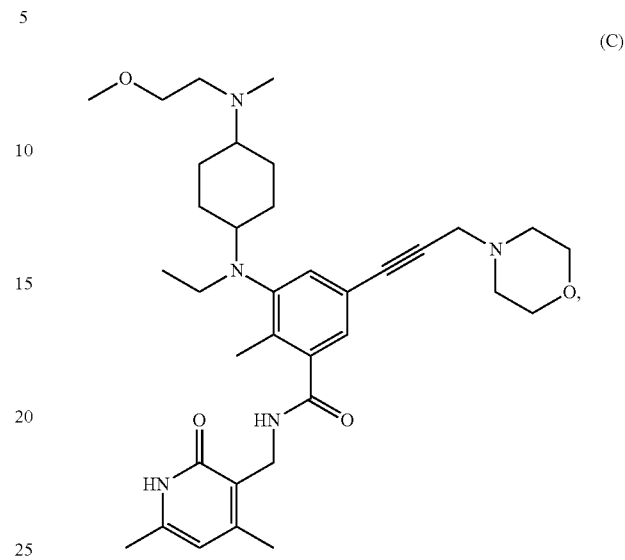

(C)

stereoisomers thereof, or pharmaceutically acceptable salts or solvates thereof.

In certain embodiments of the methods of the disclosure, the EZH2 inhibitor is Compound D having the following formula:

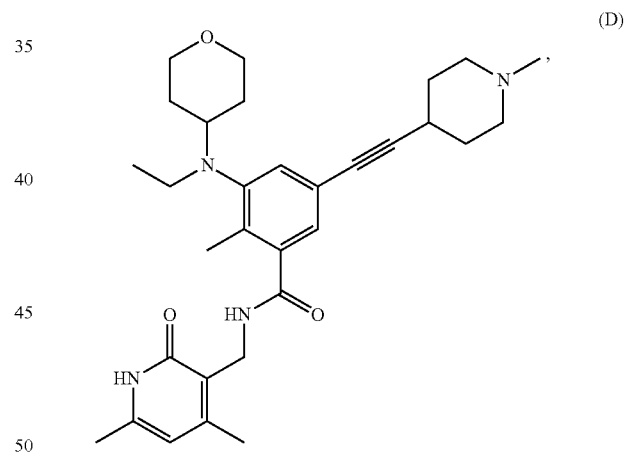

(D)

stereoisomers thereof, or pharmaceutically acceptable salts or solvates thereof.

Therapeutic agents of the disclosure (including a first and/or a second agent) may be administered by any appropriate route including, but not limited to, oral routes, intravenous routes, intramuscular routes, and direct absorption through mucous membrane tissues. The therapeutic agents can be administered by the same route or by different routes.

The methods of combination therapy featured in the disclosure may result in a synergistic effect, wherein the effect of a combination of therapeutic agents (e.g. tazemetostat and a second anti-cancer agent) is greater than the sum of the effects resulting from administration of any of the therapeutic agents as single agents. A synergistic effect may also be an effect that cannot be achieved by administration of any of the therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

Subjects of the disclosure have cancer, including, but not limited to, breast cancer, ovarian cancer or both. Subjects of the disclosure may be of any species; however, subjects are preferably human. Subjects of the disclosure may be any age; however, subjects are preferably post-adolescent. Subjects may have cancer characterized by any stage, including, but not limited to, stage 0, I, II, III, and IV. The subject's breast and/or ovarian cancer may be a primary or secondary tumor. The subject's cancer may be metastatic. The subject's breast and/or ovarian cancer may have metastasized to the breast and/or ovary from another primary location.

Subjects of the disclosure may express a wild type EZH2.

Subjects of the disclosure may express a mutant EZH2. For example, a mutant EZH2 comprises one or more mutations, wherein the mutation is a substitution, a point mutation, a nonsense mutation, a missense mutation, a deletion, or an insertion. A mutant EZH2 of the disclosure may comprise a mutation in the substrate pocket domain. A mutant EZH2 may have a substitution at amino acid Y641. Preferably, the mutant EZH2 has one of the following mutations: substitution of phenylalanine (F) for the wild type residue tyrosine (Y) at amino acid position 641 (Y641F); a substitution of histidine (H) for the wild type residue tyrosine (Y) at amino acid position 641 (Y641H); a substitution of asparagine (N) for the wild type residue tyrosine (Y) at amino acid position 641 (Y641N); a substitution of serine (S) for the wild type residue tyrosine (Y) at amino acid position 641 (Y641S); and a substitution of cysteine (C) for the wild type residue tyrosine (Y) at amino acid position 641 (Y641C).

Other mutations of EZH2 may include, but are not limited to: a substitution of glycine (G) for the wild type residue alanine (A) at amino acid position 677 (A677G); a substitution of valine (V) for the wild type residue alanine (A) at amino acid position 687 (A687V); a substitution of methionine (M) for the wild type residue valine (V) at amino acid position 674 (V674M); a substitution of histidine (H) for the wild type residue arginine (R) at amino acid position 685 (R685H); a substitution of cysteine (C) for the wild type residue arginine (R) at amino acid position 685 (R685C); a substitution of serine (S) for the wild type residue asparagine (N) at amino acid position 322 (N322S), a substitution of glutamine (Q) for the wild type residue arginine (R) at amino acid position 288 (R288Q), a substitution of isoleucine (I) for the wild type residue threonine (T) at amino acid position 573 (T573I), a substitution of glutamic acid (E) for the wild type residue aspartic acid (D) at amino acid position 664 (D664E), a substitution of glutamine (Q) for the wild type residue arginine (R) at amino acid position 458 (R458Q), a substitution of lysine (K) for the wild type residue glutamic acid (E) at amino acid position 249 (E249K), a substitution of cysteine (C) for the wild type residue arginine (R) at amino acid position 684 (R684C), a substitution of histidine (H) for the wild type residue arginine (R) at amino acid position 628 (R628H), a substitution of histidine (H) for the wild type residue glutamine (Q) at amino acid position 501 (Q501H), a substitution of asparagine (N) for the wild type residue aspartic acid (D) at amino acid position 192 (D192N), a substitution of valine (V) for the wild type residue aspartic acid (D) at amino acid position 664 (D664V), a substitution of leucine (L) for the wild type residue valine (V) at amino acid position 704 (V704L), a substitution of serine (S) for the wild type residue proline (P) at amino acid position 132 (P132S), a substitution of lysine (K) for the wild type residue glutamic acid (E) at amino acid position 669 (E669K), a substitution of threonine (T) for the wild type residue alanine (A) at amino acid position 255 (A255T), a substitution of valine (V) for the wild type residue glutamic acid (E) at amino acid position 726 (E726V), a substitution of tyrosine (Y) for the wild type residue cysteine (C) at amino acid position 571 (C571Y), a substitution of cysteine (C) for the wild type residue phenylalanine (F) at amino acid position 145 (F145C), a substitution of threonine (T) for the wild type residue asparagine (N) at amino acid position 693 (N693T), a substitution of serine (S) for the wild type residue phenylalanine (F) at amino acid position 145 (F145S), a substitution of histidine (H) for the wild type residue glutamine (Q) at amino acid position 109 (Q109H), a substitution of cysteine (C) for the wild type residue phenylalanine (F) at amino acid position 622 (F622C), a substitution of arginine (R) for the wild type residue glycine (G) at amino acid position 135 (G135R), a substitution of glutamine (Q) for the wild type residue arginine (R) at amino acid position 168 (R168Q), a substitution of arginine (R) for the wild type residue glycine (G) at amino acid position 159 (G159R), a substitution of cysteine (C) for the wild type residue arginine (R) at amino acid position 310 (R310C), a substitution of histidine (H) for the wild type residue arginine (R) at amino acid position 561 (R561H), a substitution of histidine (H) for the wild type residue arginine (R) at amino acid position 634 (R634H), a substitution of arginine (R) for the wild type residue glycine (G) at amino acid position 660 (G660R), a substitution of cysteine (C) for the wild type residue tyrosine (Y) at amino acid position 181 (Y181C), a substitution of arginine (R) for the wild type residue histidine (H) at amino acid position 297 (H297R), a substitution of serine (S) for the wild type residue cysteine (C) at amino acid position 612 (C612S), a substitution of tyrosine (Y) for the wild type residue histidine (H) at amino acid position 694 (H694Y), a substitution of alanine (A) for the wild type residue aspartic acid (D) at amino acid position 664 (D664A), a substitution of threonine (T) for the wild type residue isoleucine (I) at amino acid position 150 (I150T), a substitution of arginine (R) for the wild type residue isoleucine (I) at amino acid position 264 (I264R), a substitution of leucine (L) for the wild type residue proline (P) at amino acid position 636 (P636L), a substitution of threonine (T) for the wild type residue isoleucine (I) at amino acid position 713 (I713T), a substitution of proline (P) for the wild type residue glutamine (Q) at amino acid position 501 (Q501P), a substitution of glutamine (Q) for the wild type residue lysine (K) at amino acid position 243 (K243Q), a substitution of aspartic acid (D) for the wild type residue glutamic acid (E) at amino acid position 130 (E130D), a substitution of glycine (G) for the wild type residue arginine (R) at amino acid position 509 (R509G), a substitution of histidine (H) for the wild type residue arginine (R) at amino acid position 566 (R566H), a substitution of histidine (H) for the wild type residue aspartic acid (D) at amino acid position 677 (D677H), a substitution of asparagine (N) for the wild type residue lysine (K) at amino acid position 466 (K466N), a substitution of histidine (H) for the wild type residue arginine (R) at amino acid position 78 (R78H), a substitution of methionine (M) for the wild type residue lysine (K) at amino acid position 1 (K6M), a substitution of leucine (L) for the wild type residue serine (S) at amino acid position 538 (S538L), a substitution of glutamine (Q) for the wild type residue leucine (L) at amino acid position 149 (L149Q), a substitution of valine (V) for the wild type residue leucine (L) at amino acid position 252 (L252V), a substitution of valine (V) for the wild type residue leucine (L) at amino acid position 674 (L674V), a substitution of valine (V) for the wild type residue alanine (A) at amino acid position 656 (A656V), a substitution of aspartic acid (D) for the wild type residue alanine (A) at amino acid position 731 (Y731D), a substitution of threonine (T) for the wild type residue alanine (A) at amino acid position 345 (A345T), a substitution of aspartic acid (D) for the wild type residue alanine (A) at amino acid position 244 (Y244D), a substitution of tryptophan (W) for the wild type residue cysteine (C) at amino acid position 576 (C576W), a substitution of lysine (K) for the wild type residue asparagine (N) at amino acid position 640 (N640K), a substitution of lysine (K) for the wild type residue asparagine (N) at amino acid position 675 (N675K), a substitution of tyrosine (Y) for the wild type residue aspartic acid (D) at amino acid position 579 (D579Y), a substitution of isoleucine (I) for the wild type residue asparagine (N) at amino acid position 693 (N693I), and a substitution of lysine (K) for the wild type residue asparagine (N) at amino acid position 693 (N693K).

Other mutations of EZH2 can include: a frameshift at amino acid position 730, 391, 461, 441, 235, 254, 564, 662, 715, 405, 685, 64, 73, 656, 718, 374, 592, 505, 730, or 363 or the corresponding nucleotide position of the nucleic acid sequence; a deletion of glutamic acid (E) and leucine (L) at amino acid positions 148 and 149 or a nonsense mutation at amino acid position 733, 25, 317, 62, 553, 328, 58, 207, 123, 63, 137, or 60.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the disclosure will be apparent from the following detailed description and claims.

BRIEF DESCRIPTIONS OF FIGURES

DETAILED DESCRIPTION

Figure 1:
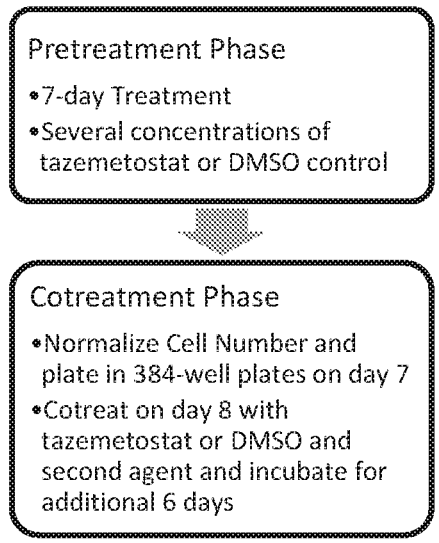
FIG. 1 is a schematic diagram depicting the experimental procedure of Example 1.

The disclosure provides a combination therapy for the treatment of cancer comprising an EZH2 inhibitor and a second anti-cancer agent. In some embodiments, the EZH2 inhibitor is a compound provided herein. In some embodiments, the EZH2 inhibitor is tazemetostat. In some embodiments, the combination of the EZH2 inhibitor and the second anti-cancer agent demonstrate synergy.

As described in Example 1, breast cancer cell lines were contacted with tazemetostat at 10 μM with a second agent. The degree of synergy and/or antagonism of each combination in breast cancer cells is shown in Table A.

As described in Example 2, ovarian cancer cell lines were contacted with tazemetostat at 10 μM with a second agent. The degree of synergy and/or antagonism of each combination in ovarian cancer cells is shown in Table B.

TABLE A

In vitro combination studies in breast cancer cell lines

| Component | Modality | ZR-75-1 | MCF-7 | MDA-MB-175VII | EFM-19 | BT474 | HCC1395 | MDA-MB-361 | MDA-MB-453 | HCC1569 | MDA-MB-231 | MDA-MB-468 | SUM52PE | SUM159PT | HCC1143 | HCC38 | MDA-MB-157 |
|---|---|---|---|---|---|---|---|---|---|---|---|---|---|---|---|---|---|
| HER2 Status | | +/+ | +/+ | +/+ | +/+ | +/+ | +/− | +/− | −/− | −/− | −/− | −/− | −/− | −/− | −/− | −/− | −/− |
| ER/PR Status | | + | + | + | + | + | − | − | − | − | − | − | − | − | − | − | + |
| Trametinib | MEK inhibitor | B | A | | | | | | A | | | C | | | | | C |
| Idelalisib | PI3K delta inhibitor | | | | X | | | | | | | | | | C | | X |
| BKM120 | PI3K p110α/β/δ/γ inhibitor | X | X | | | X | X | X | X | | X | X | X | X | X | X | |
| Dasatinib | BCR/Abl SRC Kinase | | | C | | | | | | C | C | B | B | B | B | C | |
| ENMD-2076 | Aurora A and VEGFR dual inhibitor | | | C | | | | | A | | | | C | | | | |
| Everolimus | mTOR inhibitor | | | C | | | | | | | | C | | C | C | | C |
| Dinaciclib | CDK inhibitor | | | | | | | | | | | | | | | | |
| Paclitaxel | Microtubule inhibitor | C | | | | | | | | | | | | | | | |
| Epirubicin | Topoisomerase inhibitor | | | | | | | | | | | C | | C | C | | |
| Etoposide | Topoisomerase inhibitor | | | | | | | | | | | | | | | | |
| Mifepristone | Antiprogesterone and Anti-glucocorticoid | | | | | | | | | | | | | | | | |
| Iniparib (BSI 201) | Parp Inhibitor | | | | | | | | | | | | | C/B | C | | |
| Olaparib | Parp Inhibitor | | | | | | | | | C | | C | | | | | |
| MK2206 | AKT inhibitor | | C | | | | | | | | | | | | | | |
| Mafosfamide | Alkylating agent | | | | | | | | | | | | | | | | |
| Gemcitabine | Nucleoside metabolic inhibitor | | | | | | | | | | | C | | C | | | |
| Cisplatin | Platinum/cross links DNA | A | | | | | | | | | | | | | | | |
| Tamoxifen Citrate | Estrogen Agonist | | B | | | | X | | | | | | | A | | | |
| Anastozole | Aromatase Inhibitor | | | | | | | | | | | | | | | | |

TABLE A-continued

In vitro combination studies in breast cancer cell lines

| | | Cell Line | | | | | | | | | | | | | | |
|---|---|---|---|---|---|---|---|---|---|---|---|---|---|---|---|---|
| | | HCC1806 | DU4475 | SUM149PT | HCC202 | SK-BR-3 | MDA-MB-436 | BT549 | HCC70 | HCC1187 | HCC1937 | SUM1315MO2 | HCC1954 | CAMA-1 | BT-20 | HCC1419 |
| | ER/PR Status | -/- | -/- | -/- | -/- | -/- | -/- | -/- | -/- | -/- | -/- | -/- | -/- | +/- | -/- | -/- |
| | HER2 Status | - | + | - | + | + | - | - | - | - | + | + | + | + | - | + |
| Letrozole | Aromatase Inhibitor | | | | | | | | | | | | | | | |
| Lapatinib | EGFR/HER2 inhibitor | | | | | | | | | | | | A | | | |
| Azacitadine | DNA hypomethylation | C | | | | | | | | | C | C | | | C | |
| Decitabine | DNA hypomethylation | C | | | | A | | B | | | C | C | C | B | | |
| SGI1027 | DNA hypomethylation | X | | | B | | | | X | X | X | X | X | X | | X |
| JQI | Bromodomain inhibitor | X | | X | X | | X | X | | X | X | X | X | C | | C |
| Methotrexate | Anti-folate | X | X | X | X | X | X | X | X | X | X | X | X | X | X | X |
| Tazemetostat sensitivity at 10 μM (%) | | A 50 | A 10 | A 20 | A 0 | A 25 | 10 | A 40 | A 20 | A 0 | A 30 | A 50 | A 50 | A 0 | A 20 | A 0 |
| Trametinib | MEK inhibitor | | | | | | C | | C | | | | | B | C | |
| Idelalisib | PI3K delta inhibitor | X | X | X | X | X | X | X | X | X | X | X | X | X | X | X |
| BKM120 | PI3K p110α/β/δ/γ inhibitor | | A | | | | | | B | | | | | | C | C |
| Dasatinib | BCR/Abl SRC Kinase | | B | | | | | | B | | | | | | | |
| ENMD-2076 | Aurora A and VEGFR dual inhibitor | | | | | | | A | | | | | | | | |
| Everolimus | mTOR inhibitor | | | | | | | | | | | | | A | | C |
| Dinaciclib | CDK inhibitor | | | | | | | | | | | | | | | |
| Paclitaxel | Microtubule inhibitor | | B | | | | | | | C | | | | | | C |
| Epirubicin | Topoisomerase inhibitor | | | C | | | | | | | | | | | | |

Legend:
- A — Synergy > 4× IC$_{50}$ shift
- B — Synergy > 2× IC$_{50}$ shift
- C — No Effect
- (blank) — Antagonism
- X — Not Tested TABLE A-continued In vitro combination studies in breast cancer cell lines

| Drug | Class | 1 | 2 | 3 | 4 | 5 | 6 | 7 | 8 | 9 | 10 |
|---|---|---|---|---|---|---|---|---|---|---|---|
| Etoposide | Topoisomerase inhibitor | | | | C | | | | | | C |
| Mifepristone | Antiprogesterone and Antiglucocorticoid | C | | | | | | | | | |
| Iniparib (BSI 201) | Parp Inhibitor | | | | | | | | | C | C |
| Olaparib | Parp Inhibitor | | B | | | | | | | | |
| MK2206 | AKT inhibitor | | | | C | | | | | | C X C |
| Mafosfamide | Alkylating agent | | | | | | | | | X | |
| Gemcitabine | Nucleoside metabolic inhibitor | | | | | | | | | | |
| Cisplatin | Platinum/cross links DNA | | | | | C | C | | | | |
| Tamoxifen Citrate | Estrogen Agonist | | | | | | | | | | |
| Anastozole | Aromatase Inhibitor | | | X | X | X | | | | | A |
| Letrozole | Aromatase Inhibitor | | | A | C | C | | | | | |
| Lapatinib | EGFR/HER2 inhibitor | | | | | | | | | | |
| Azacitadine | DNA hypomethylation | | C | | C | | C | | | | |
| Decitabine | DNA hypomethylation | | | | A | | B | | | | |
| SGH1027 | DNA hypomethylation | X | A | X | X | X | | X | X | C | |
| JQI | Bromodomain inhibitor | X | X | X | X | | | X | | | C |
| Methotrexate | Anti-folate | A | A | A | A | A | A | A | A | A | C |
| | | 40 | 35 | 30 | 70 | 40 | 35 | 20 | 35 | 0 | 0 |
| Tazemetostat sensitivity at 10 μM (%) | | | | 0 | 10 | | | | | 30 | 0 |

Synergy > 4× IC$_{50}$ shift — A
Synergy > 2× IC$_{50}$ shift — B
No Effect — C
Antagonism — X
Not Tested

TABLE B

In vitro combination studies in ovarian cancer cell lines

| | | Cell Type | | | | | | |
|---|---|---|---|---|---|---|---|---|
| | | Clear cell | | | | Non-Clear Cell | | |
| | | Cell subtype | | | | | | |
| | | ARID1A | | NON-ARID1A | | p53 | | |
| | | Cell Line | | | | | | |
| | | OVMANA | OVISE | TOV21G | ES-2 | COV362 | OVSAHO | KURAMOCHI |
| | | Annotation | | | | | | |
| | | Clear | Clear | Clear | Clear | Endometrioid | Serous | NS |
| | | Grade | | | | | | |
| | | MID-LOW | MID-LOW | LOW | HIGH-MID | HIGH | HIGH | HIGH |
| | | Mutations | | | | | | |
| Drugs | Modality | PI3K, ARID1A, BRCA2 | ARID1A | PI3K, PTEN, BRAF, ARID1A | p53, BRAF, CREBBP | p53, BRCA1, RB1 (amp MYC) | p53 (del BRACA2, RB1) | p53, BRCA2 (amp MYC, KRAS), MLL |
| Carboplatin | DNA Adduct Forming | | | X | | | X | |
| Cisplatin | DNA Adduct Forming | | | | | | | |
| Paclitaxel | Binds Microtubules | | | | C | | | |
| Docetaxel | Binds Microtubules | | | X | C | | | |
| Gemcitabine | Antimetabolite | | | X | | | X | |
| Topotecan | DNA intercalation | | | | | | | C |
| Doxorubicin | DNA intercalation | C | | | C | | | |
| Mafosfamide | Alkylating agent | | | X | | | X | |
| MK2206 | AKT inhibitor | | | X | | | X | B |
| AZD5363 | AKT inhibitor | | | | | | X | |
| Methotrexate | Antimetabolite | A | A | | A | A | A | A |
| ABT199 | BCL2 inhibitor | X | | X | | | X | |
| Vemurafenib | BRAF inhibitor | | | X | C | | X | |
| JQ1 | Bromodomain inhibitor | | | C | C | | X | |
| LY2606318 | CHK1/2 inhibitor | | | | | C | | C |
| Decitabine | DNMT inhibitor | | | X | | | X | |
| Azacitidine | DNMT inhibitor | | | X | | | X | |
| Lapatinib | EGFR inhibitor and ERBB2/HER2 | B | | | | | X | C |
| Erlotinib | EGFR inhibitor | C | | X | | | X | |
| Vorinostat | HDAC inhibitor | C | B | | | | C | C |
| Panobinostat | HDAC inhibitor | C | C | C | | C | C | C |
| Mocetinostat | HDAC inhibitor | C | | | X | C | X | C |
| Entinostat | HDAC inhibitor | C | | | X | | X | B |
| Romidepsin | HDAC inhibitor | C | C | C | X | C | X | X |
| Trametinib | MEK1/2 inhibitor | | | | C | | | |
| Rapamycin | mTOR inhibitor | | | X | | | X | |
| GSK690693 | Pan AKT inhibitor | | | | | | | C |
| Olaparib | PARP inhibitor | | | X | | | X | |

TABLE B-continued

In vitro combination studies in ovarian cancer cell lines

| | | | | | | | | |
|---|---|---|---|---|---|---|---|---|
| BYL719 | PI3K inhibitor | | C | | | | | |
| BKM120 | PI3K inhibitor | | C | | | | | C |
| Pictilisib | PI3K inhibitor | C | | | | | | |
| Imatinib | v-Abl, cKit, PDGFR PI3K inhibitor | | | X | A | | X | |
| AZD2171 | VEGF inhibitor | | | | | | X | C |
| MK1775 | Wee2 PI3K inhibitor | | | | | | | C |
| Tazemetostat % inhibition at 20 μM | | 20 | 0 | 40 | 0 | 0 | 0 | 20 |
| Synergy > 4× IC$_{50}$ shift | | B | | | | | | |
| Synergy > 2× IC$_{50}$ shift | | C | | | | | | |
| No Effect | | | | | | | | |
| Antagonism | | A | | | | | | |
| Not Tested | | X | | | | | | |

| | | Cell Type Non-Clear Cell | | | | | | |
|---|---|---|---|---|---|---|---|---|
| | | Cell subtype | | | | | | |
| | | p53 | | | | | | |
| | | JH)S-4 | TYK-NU | CAOV-3 | OVCAR-3 | COV504 | OV-90 | RMUGS* |
| | | Annotation | | | | | | |
| | | Serous | NS | NS | NS | Serous | Serous | Mucinous |
| | | Grade | | | | | | |
| | | | HIGH-MID | HIGH-MID | MID | | MID | |
| | | Mutation | | | | | | |
| Drugs | Modality | p53 | p53 | p53 | p53, CCNE1 | p53, MLL3 | p53 | p53 |
| Carboplatin | DNA Adduct Forming | X | | | | | | |
| Cisplatin | DNA Adduct Forming | C | | | | | | C |
| Paclitaxel | Binds Microtubules | C | A | C | | | | C |
| Docetaxel | Binds Microtubules | C | | | | | | C |
| Gemcitabine | Antimetabolite | X | | | C | | B | |
| Topotecan | DNA intercalation | C | | | C | C | B | |
| Doxorubicin | DNA intercalation | C | | | B | C | B | |
| Mafosfamide | Alkylating agent | X | X | | | | X | C |
| MK2206 | AKT inhibitor | X | X | | | | X | |
| AZD5363 | AKT inhibitor | X | | | | | | |
| Methotrexate | Antimetabolite | A | A | A | A | A | A | |
| ABT199 | BCL2 inhibitor | X | X | | | | X | |
| Vemurafenib | BRAF inhibitor | X | X | | | | X | |
| JQ1 | Bromodomain inhibitor | X | | B | | C | C | |
| LY2606318 | CHK1/2 inhibitor | | | A | | B | | |
| Decitabine | DNMT inhibitor | X | X | | | | X | |
| Azacitidine | DNMT inhibitor | X | | | | C | C | |
| Lapatinib | EGFR inhibitor and ERBB2/HER2 | X | | | | C | | |
| Erlotinib | EGFR inhibitor | X | | | | | | B |
| Vorinostat | HDAC inhibitor | C | A | C | | C | | C |
| Panobinostat | HDAC inhibitor | C | | C | | B | C | |
| Mocetinostat | HDAC inhibitor | X | X | | | | C | |
| Entinostat | HDAC inhibitor | X | X | | C | C | C | C |
| Romidepsin | HDAC inhibitor | X | X | C | | C | X | C |
| Trametinib | MEK1/2 inhibitor | C | | B | | B | | C |
| Rapamycin | mTOR inhibitor | X | X | | | | X | |

TABLE B-continued

In vitro combination studies in ovarian cancer cell lines

| Drugs | Modality | | | | | | | |
|---|---|---|---|---|---|---|---|---|
| GSK690693 | Pan AKT inhibitor | | | | | | | C |
| Olaparib | PARP inhibitor | X | X | | | | X | |
| BYL719 | PI3K inhibitor | | | C | | B | | |
| BKM120 | PI3K inhibitor | C | | | | C | | |
| Pictilisib | PI3K inhibitor | | | C | | | | |
| Imatinib | v-Abl, cKit, PDGFR PI3K inhibitor | X | | | | | | |
| AZD2171 | VEGF inhibitor | X | | | | B | | C |
| MK1775 | Wee2 PI3K inhibitor | C | | C | | C | | B |
| Tazemetostat % inhibition at 20 μM | | −20 | 0 | 0 | 0 | 30 | 15 | −20 |

Synergy > 4× $IC_{50}$ shift
Synergy > 2× $IC_{50}$ shift
No Effect
Antagonism
Not Tested

| | | Cell Type Non-Clear Cell Cell subtype | | | | | | |
|---|---|---|---|---|---|---|---|---|
| | | p53 | NON-p53 | | | | | |
| | | TOV112D | COV644* | SNU840 | OAW42 | COV434 | SKOV3 | A2780 |
| | | | | | Annotation | | | |
| | | Mucinous | Mucinous | Other | Serous | Other | NS | Clear |
| | | | | | Grade | | | |
| | | HYPER-MUT | MID | MID-LOW | MID-LOW | LOW | LOW | |
| | | | | | Mutation | | | |
| Drugs | Modality | p53 | EP300 | PI3K, MLL3 | PI3K, ARID1A | ARID1A | PI3K, ARID1A (amp KRAS), EP300 | PI3K, PTEN, BRAF, ARID1A |
| Carboplatin | DNA Adduct Forming | | | | | | | B |
| Cisplatin | DNA Adduct Forming | C | | | | | C | B |
| Paclitaxel | Binds Microtubules | | C | | B | | C | C |
| Docetaxel | Binds Microtubules | C | C | | C | | B | X |
| Gemcitabine | Antimetabolite | | | | | | C | B |
| Topotecan | DNA intercalation | | | B | | | C | B |
| Doxorubicin | DNA intercalation | C | C | | | | B | B |
| Mafosfamide | Alkylating agent | | | | | X | | B |
| MK2206 | AKT inhibitor | | | B | | | | B |
| AZD5363 | AKT inhibitor | X | | | | | | B |
| Methotrexate | Antimetabolite | A | A | A | A | A | | A |
| ABT199 | BCL2 inhibitor | C | | | | X | | C |
| Vemurafenib | BRAF inhibitor | | | | | X | | |
| JQ1 | Bromodomain inhibitor | C | | | | | B | B |
| LY2606318 | CHK1/2 inhibitor | C | | C | | | C | B |
| Decitabine | DNMT inhibitor | C | | | | X | | |
| Azacitidine | DNMT inhibitor | C | | | | | | C |
| Lapatinib | EGFR inhibitor and ERBB2/HER2 | C | B | B | | | | |
| Erlotinib | EGFR inhibitor | B | | | | | | |
| Vorinostat | HDAC inhibitor | C | C | | | | B | B |
| Panobinostat | HDAC inhibitor | C | C | C | | | B | B |
| Mocetinostat | HDAC inhibitor | C | X | X | | C | B | X |
| Entinostat | HDAC inhibitor | C | X | X | | C | C | X |
| Romidepsin | HDAC inhibitor | C | X | X | C | C | C | X |

TABLE B-continued

In vitro combination studies in ovarian cancer cell lines

| | | | | | | | | |
|---|---|---|---|---|---|---|---|---|
| Trametinib | MEK1/2 inhibitor | | | B | | | C | B |
| Rapamycin | mTOR inhibitor | X | | | | X | | |
| GSK690693 | Pan AKT inhibitor | | | B | B | | B | C |
| Olaparib | PARP inhibitor | | | | | X | | B |
| BYL719 | PI3K inhibitor | C | C | B | | | C | B |
| BKM120 | PI3K inhibitor | C | C | | | C | C | C |
| Pictilisib | PI3K inhibitor | X | C | C | | | | C |
| Imatinib | v-Abl, cKit, PDGFR PI3K inhibitor | | | | | | | |
| AZD2171 | VEGF inhibitor | | C | | | | | C |
| MK1775 | Wee2 PI3K inhibitor | C | B | | | | C | B |
| Tazemetostat % inhibition at 20 μM | | 20 | 10 | 25 | 15 | 50 | 15 | 35 |
| Synergy > 4× IC$_{50}$ shift | | | | | | | | |
| Synergy > 2× IC$_{50}$ shift | | | | | | | | |
| No Effect | | | | | | | | |
| Antagonism | | | | | | | | |
| Not Tested | | | | | | | | |

EZH2

EZH2 is a histone methyltransferase that is the catalytic subunit of the PRC2 complex which catalyzes the mono- through tri-methylation of lysine 27 on histone H3 (H3-K27). Histone H3-K27 trimethylation is a mechanism for suppressing transcription of specific genes that are proximal to the site of histone modification. This trimethylation is known to be a cancer marker with altered expression in cancer, such as prostate cancer (see, e.g., U.S. Patent Application Publication No. 2003/0175736; incorporated herein by reference in its entirety). Other studies provided evidence for a functional link between dysregulated EZH2 expression, transcriptional repression, and neoplastic transformation. Varambally et al. (2002) *Nature* 419(6907):624-9 Kleer et al. (2003) *Proc Natl Acad Sci USA* 100(20):11606-11.

Human EZH2 nucleic acids and polypeptides have previously been described. See, e.g., Chen et al. (1996) *Genomics* 38:30-7 [746 amino acids]; Swiss-Prot Accession No. Q15910 [746 amino acids]; GenBank Accession Nos. NM_004456 and NP_004447 (isoform a [751 amino acids]); and GenBank Accession Nos. NM_152998 and NP_694543 (isoform b [707 amino acids]), each of which is incorporated herein by reference in its entirety.

Also for purposes of this application, a Y641 mutant of human EZH2, and, equivalently, a Y641 mutant of EZH2, is to be understood to refer to a human EZH2 in which the amino acid residue corresponding to Y641 of wild-type human EZH2 is substituted by an amino acid residue other than tyrosine.

In one embodiment the amino acid sequence of a Y641 mutant of EZH2 differs from the amino acid sequence of wild-type human EZH2 only by substitution of a single amino acid residue corresponding to Y641 of wild-type human EZH2 by an amino acid residue other than tyrosine.

In one embodiment the amino acid sequence of a Y641 mutant of EZH2 differs from the amino acid sequence of wild-type human EZH2 only by substitution of phenylalanine (F) for the single amino acid residue corresponding to Y641 of wild-type human EZH2. The Y641 mutant of EZH2 according to this embodiment is referred to herein as a Y641F mutant or, equivalently, Y641F.

In one embodiment the amino acid sequence of a Y641 mutant of EZH2 differs from the amino acid sequence of wild-type human EZH2 only by substitution of histidine (H) for the single amino acid residue corresponding to Y641 of wild-type human EZH2. The Y641 mutant of EZH2 according to this embodiment is referred to herein as a Y641H mutant or, equivalently, Y641H.

In one embodiment the amino acid sequence of a Y641 mutant of EZH2 differs from the amino acid sequence of wild-type human EZH2 only by substitution of asparagine (N) for the single amino acid residue corresponding to Y641 of wild-type human EZH2. The Y641 mutant of EZH2 according to this embodiment is referred to herein as a Y641N mutant or, equivalently, Y641N.

In one embodiment the amino acid sequence of a Y641 mutant of EZH2 differs from the amino acid sequence of wild-type human EZH2 only by substitution of serine (S) for the single amino acid residue corresponding to Y641 of wild-type human EZH2. The Y641 mutant of EZH2 according to this embodiment is referred to herein as a Y641S mutant or, equivalently, Y641S.

In one embodiment the amino acid sequence of a Y641 mutant of EZH2 differs from the amino acid sequence of wild-type human EZH2 only by substitution of cysteine (C) for the single amino acid residue corresponding to Y641 of wild-type human EZH2. The Y641 mutant of EZH2 according to this embodiment is referred to herein as a Y641C mutant or, equivalently, Y641C.

In one embodiment the amino acid sequence of a A677 mutant of EZH2 differs from the amino acid sequence of wild-type human EZH2 only by substitution of a non-alanine amino acid, preferably glycine (G) for the single amino acid residue corresponding to A677 of wild-type human EZH2. The A677 mutant of EZH2 according to this embodiment is referred to herein as an A677 mutant, and preferably an A677G mutant or, equivalently, A677G.

In one embodiment the amino acid sequence of a A687 mutant of EZH2 differs from the amino acid sequence of wild-type human EZH2 only by substitution of a non-alanine amino acid, preferably valine (V) for the single amino acid residue corresponding to A687 of wild-type human EZH2. The A687 mutant of EZH2 according to this embodiment is referred to herein as an A687 mutant and preferably an A687V mutant or, equivalently, A687V.

In one embodiment the amino acid sequence of a R685 mutant of EZH2 differs from the amino acid sequence of wild-type human EZH2 only by substitution of a non-arginine amino acid, preferably histidine (H) or cysteine (C) for the single amino acid residue corresponding to R685 of wild-type human EZH2. The R685 mutant of EZH2 according to this embodiment is referred to herein as an R685 mutant and preferably an R685C mutant or an R685H mutant or, equivalently, R685H or R685C.

Cells heterozygous for EZH2 would be expected to display a malignant phenotype due to the efficient formation of H3-K27me1 by the WT enzyme and the efficient, subsequent transition of this progenitor species to H3-K27me2, and, especially, H3-K27me3, by the mutant enzyme form(s).

Previous results point to dependency on enzymatic coupling between enzymes that perform H3-K27 mono-methylation and certain mutant forms of EZH2 for pathogenesis in follicular lymphoma and diffuse large B-cell lymphoma. For example, cells expressing Y641 mutant EZH2 may be more sensitive to small molecule EZH2 inhibitors than cells expressing WT EZH2. Specifically, cells expressing Y641 mutant EZH2 show reduced growing, dividing or proliferation, or even undergo apoptosis or necrosis after the treatment of EZH2 inhibitors. In contrast, cells expressing WT EZH2 are not responsive to the anti-proliferative effect of the EZH2 inhibitors (U.S. patent application Ser. No. 13/230,703 (now U.S. Pat. 8,895,245); incorporated herein by reference in its entirety.)

An aspect of the disclosure is a method for treating or alleviating a symptom of cancer or precancerous condition in a subject by administering to a subject expressing either a wild type or a mutant EZH2 a therapeutically effective amount of an EZH2 inhibitor as described herein, e.g., a compound of Formulae (I)-(VIa) (preferably tazemetostat) in combination with a second anti-cancer agent suitable to be administered together simultaneously, sequentially, or in alternation.

Another aspect of the disclosure is a method for inhibiting in a subject conversion of H3-K27 to trimethylated H3-K27. The inhibition can involve inhibiting in a subject conversion of unmethylated H3-K27 to monomethylated H3-K27, conversion of monomethylated H3-K27 to dimethylated H3-K27, conversion of dimethylated H3-K27 to trimethylated H3-K27, or any combination thereof, including, for example, conversion of monomethylated H3-K27 to dimethylated H3-K27 and conversion of dimethylated H3-K27 to trimethylated H3-K27. As used herein, unmethylated H3-K27 refers to histone H3 with no methyl group covalently linked to the amino group of lysine 27. As used herein, monomethylated H3-K27 refers to histone H3 with a single methyl group covalently linked to the amino group of lysine 27. Monomethylated H3-K27 is also referred to herein as H3-K27me1. As used herein, dimethylated H3-K27 refers to histone H3 with two methyl groups covalently linked to the amino group of lysine 27. Dimethylated H3-K27 is also referred to herein as H3-K27me2. As used herein, trimethylated H3-K27 refers to histone H3 with three methyl groups covalently linked to the amino group of lysine 27. Trimethylated H3-K27 is also referred to herein as H3-K27me3.

Histone H3 is a 136 amino acid long protein, the sequence of which is known. See, for example, GenBank Accession No. CAB02546, the content of which is incorporated herein by reference. As disclosed further herein, in addition to full-length histone H3, peptide fragments of histone H3 comprising the lysine residue corresponding to K27 of full-length histone H3 can be used as substrate for EZH2 (and likewise for mutant forms of EZH2) to assess conversion of H3-K27m1 to H3-K27m2 and conversion of H3-K27m2 to H3-K27m3. In one embodiment, such peptide fragment corresponds to amino acid residues 21-44 of histone H3.

EZH2 Inhibitors

EZH2 inhibitors of the disclosure include compounds of Formulae (I)-(VIa). Other compounds of Formulae (I)-(VIa) suitable for the methods of the disclosure are described in U.S. Publication 20120264734, the contents of which are hereby incorporated by reference in their entireties.

An EZH2 inhibitor of the disclosure may have the following Formula I:

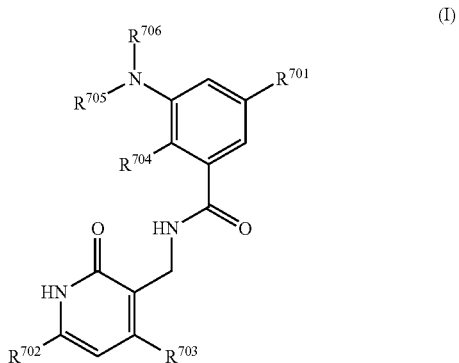

or a pharmaceutically acceptable salt thereof; wherein
$R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O-$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$ independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$ independently is $C_{1-4}$ alkyl;

$R^{706}$ is cyclohexyl substituted by N($C_{1-4}$ alkyl)$_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}$ alkyl$)_2$ wherein one of the $C_{1-4}$ alkyl is unsubstituted and the other is substituted with methoxy.

For example, $R^{706}$ is

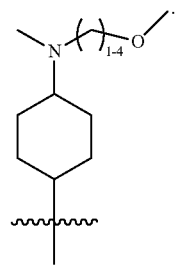

An EZH2 inhibitor of the disclosure may have the following Formula II:

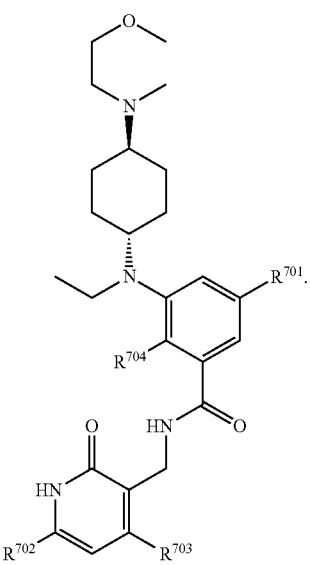

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

An EZH2 inhibitor of the disclosure may have the following Formula III:

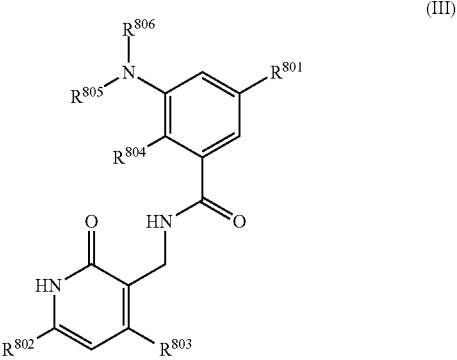

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$ independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$ independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$ and $Q_2$ independently is a bond or methyl linker, and each of $T_x$ and $T_2$ independently is tetrahydropyranyl, piperidinyl substituted by 1, 2, or 3 $C_{1-4}$ alkyl groups, or cyclohexyl substituted by $N(C_{1-4}$ alkyl$)_2$ wherein one or both of the $C_{1-4}$ alkyl is optionally substituted with $C_{1-6}$ alkoxy;

For example, $R^{806}$ is cyclohexyl substituted by $N(C_{1-4}$ alkyl$)_2$ or $R^{806}$ is tetrahydropyranyl.

For example, $R^{806}$ is

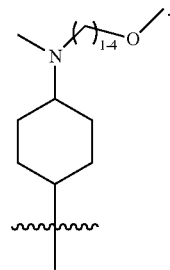

For example, $R^{801}$ is phenyl or 5- or 6-membered heteroaryl substituted with O—$C_{1-6}$ alkyl-$R_x$, or $R^{801}$ is phenyl substituted with $CH_2$-tetrahydropyranyl.

An EZH2 inhibitor of the disclosure may have the following Formula IVa or IVb:

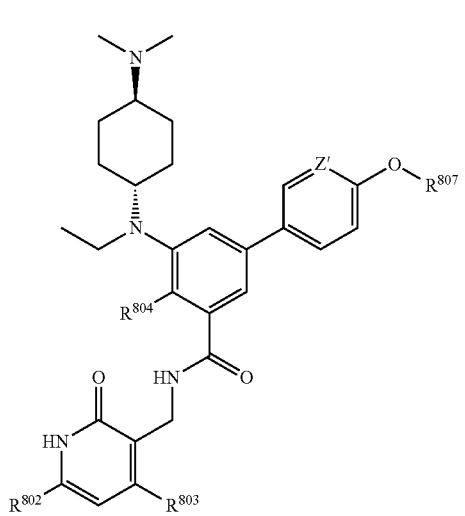

(IVa)

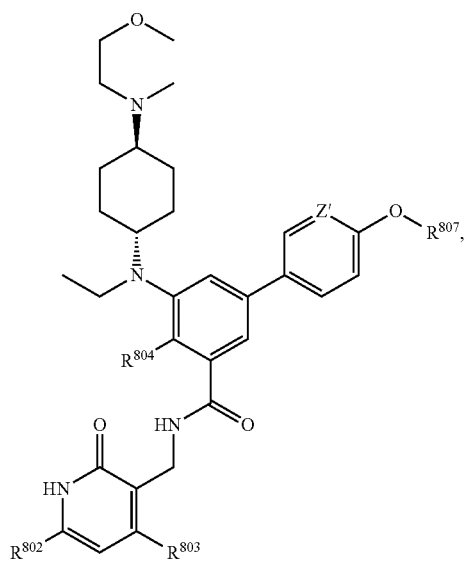

(IVb)

wherein Z' is CH or N, and $R^{807}$ is $C_{2-3}$ alkyl-$R_x$.

For example, $R^{807}$ is —$CH_2CH_2OH$, —$CH_2CH_2OCH_3$, or —$CH_2CH_2OCH_2CH_2OCH_3$.

For example, $R^{802}$ is methyl or isopropyl and $R^{803}$ is methyl or methoxy.

For example, $R^{804}$ is methyl.

An EZH2 inhibitor of the disclosure may have the following Formula (V):

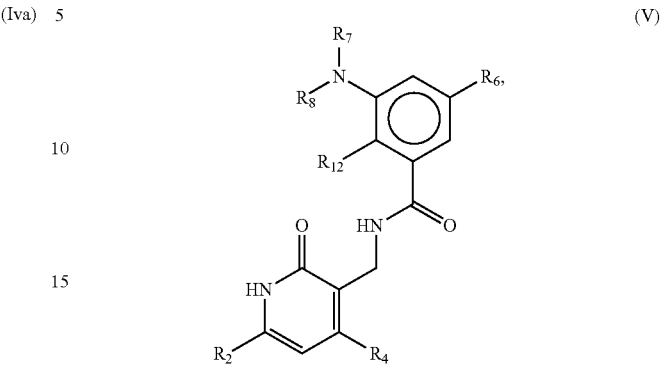

(V)

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R^a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R^a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_a$, $COOR_a$, —$S(O)_2R_d$, —$NR_dR_e$, and —$C(O)NR_dR_e$, each of $R^d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$ or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, C$_3$-C$_8$ cycloalkyl, C$_6$-C$_{10}$ aryl, 4 to 12-membered heterocycloalkyl, or 5- or 6-membered heteroaryl, and each of R$_{S4}$ and R$_{S5}$ is optionally substituted with one or more -Q$_5$-T$_5$, wherein Q$_5$ is a bond, C(O), C(O)NR$_k$, NR$_k$C(O), S(O)$_2$, or C$_1$-C$_3$ alkyl linker, R$_k$ being H or C$_1$-C$_6$ alkyl, and T$_5$ is H, halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, 5- or 6-membered heteroaryl, or S(O)$_q$R$_q$ in which q is 0, 1, or 2 and R$_q$ is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 12-membered heterocycloalkyl, or 5- or 6-membered heteroaryl, and T$_5$ is optionally substituted with one or more substituents selected from the group consisting of halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl except when T$_5$ is H, halo, hydroxyl, or cyano; or -Q$_5$-T$_5$ is oxo; and R$_8$ is H, halo, hydroxyl, COOH, cyano, R$_{S6}$, OR$_{S6}$, or COOR$_{S6}$, in which R$_{S6}$ is C$_1$-C$_6$ alkyl, C$_2$-C$_6$ alkenyl, C$_2$-C$_6$ alkynyl, C$_3$-C$_8$ cycloalkyl, 4 to 12-membered heterocycloalkyl, amino, mono-C$_1$-C$_6$ alkylamino, or di-C$_1$-C$_6$ alkylamino, and R$_{S6}$ is optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, and di-C$_1$-C$_6$ alkylamino; or R$_7$ and R$_8$, together with the N atom to which they are attached, form a 4 to 11-membered heterocycloalkyl ring having 0 to 2 additional heteroatoms, and the 4 to 11-membered heterocycloalkyl ring formed by R$_7$ and R$_8$ is optionally substituted with one or more -Q$_6$-T$_6$, wherein Q$_6$ is a bond, C(O), C(O)NR$_m$, NR$_m$C(O), S(O)$_2$, or C$_1$-C$_3$ alkyl linker, R$_m$ being H or C$_1$-C$_6$ alkyl, and T$_6$ is H, halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, 5- or 6-membered heteroaryl, or S(O)$_p$R$_p$ in which p is 0, 1, or 2 and R$_p$ is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 12-membered heterocycloalkyl, or 5- or 6-membered heteroaryl, and T$_6$ is optionally substituted with one or more substituents selected from the group consisting of halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl except when T$_6$ is H, halo, hydroxyl, or cyano; or -Q$_6$-T$_6$ is oxo.

For example, R$_6$ is C$_6$-C$_{10}$ aryl or 5- or 6-membered heteroaryl, each of which is optionally, independently substituted with one or more -Q$_2$-T$_2$, wherein Q$_2$ is a bond or C$_1$-C$_3$ alkyl linker, and T$_2$ is H, halo, cyano, —OR$_a$, —NR$_a$R$_b$, —(NR$_a$R$_b$R$_c$)$^+$A$^-$, —C(O)NR$_a$R$_b$, —NR$_a$C(O)R$_a$, —S(O)$_2$R$_a$, or R$_{S2}$, in which each of R$^a$ and R$_b$, independently is H or R$_{S3}$, each of R$_{S2}$ and R$_{S3}$, independently, is C$_1$-C$_6$ alkyl, or R$^a$ and R$_b$, together with the N atom to which they are attached, form a 4 to 7-membered heterocycloalkyl ring having 0 or 1 additional heteroatom, and each of R$_{S2}$, R$_{S3}$, and the 4 to 7-membered heterocycloalkyl ring formed by R$^a$ and R$_b$, is optionally, independently substituted with one or more -Q$_3$-T$_3$, wherein Q$_3$ is a bond or C$_1$-C$_3$ alkyl linker and T$_3$ is selected from the group consisting of halo, C$_1$-C$_6$ alkyl, 4 to 7-membered heterocycloalkyl, OR$_a$, —S(O)$_2$R$_d$, and —NR$_d$R$_e$, each of R$^d$ and R$_e$ independently being H or C$_1$-C$_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S.

An EZH2 inhibitor of the disclosure may have the following Formula (VIa):

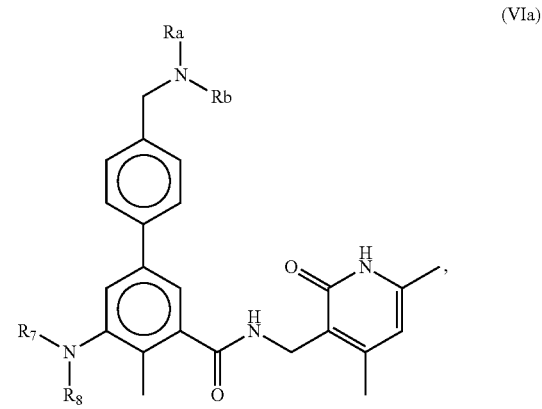

(VIa)

or a pharmaceutically acceptable salts or esters thereof, wherein R$_7$, R$_8$, R$_a$, and R$^b$ are defined herein.

The compounds of Formula (VIa) can include one or more of the following features:

For example, each of R$^a$ and R$^b$ independently is H or C$_1$-C$_6$ alkyl optionally substituted with one or more -Q$_3$-T$_3$.

For example, one of R$^a$ and R$^b$ is H.

For example, R$^a$ and R$_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more -Q$_3$-T$_3$.

For example, R$^a$ and R$_b$, together with the N atom to which they are attached, form azetidinyl, pyrrolidinyl, imidazolidinyl, pyrazolidinyl, oxazolidinyl, isoxazolidinyl, triazolidinyl, tetrahydrofuranyl, piperidinyl, 1,2,3,6-tetrahydropyridinyl, piperazinyl, or morpholinyl, and the ring is optionally substituted with one or more -Q$_3$-T$_3$.

For example, one or more -Q$_3$-T$_3$ are oxo.

For example, Q$_3$ is a bond or unsubstituted or substituted C$_1$-C$_3$ alkyl linker.

For example, T$_3$ is H, halo, 4 to 7-membered heterocycloalkyl, C$_1$-C$_3$ alkyl, OR$_d$, COOR$_d$, —S(O)$_2$R$_d$, or —NR$_d$R$_e$.

For example, each of R$_d$ and R$_e$ independently being H or C$_1$-C$_6$ alkyl.

For example, R$_7$ is C3-C8 cycloalkyl or 4 to 7-membered heterocycloalkyl, each optionally substituted with one or more -Q$_5$-T$_5$.

For example, R$_7$ is piperidinyl, tetrahydropyran, tetrahydro-2H-thiopyranyl, cyclopentyl, cyclohexyl, pyrrolidinyl, or cycloheptyl, each optionally substituted with one or more -Q$_5$-T$_5$.

For example, R$_7$ is cyclopentyl cyclohexyl or tetrahydro-2H-thiopyranyl, each of which is optionally substituted with one or more -Q$_5$-T$_5$.

For example, $Q_5$ is NHC(O) and $T_5$ is $C_1$-$C_6$ alkyl or $C_1$-$C_6$ alkoxy, each For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, di-$C_1$-$C_6$ alkylamino.

For example, $Q_5$ is CO, S(O)$_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

For example, $R_8$ is H, methyl, or ethyl.

In one embodiment, the compound of the disclosure is tazemetostat (also referred to as Compound 44 or Compound A):

(A)

or a pharmaceutically acceptable salt thereof.

In some embodiments, a compound of the disclosure is:

(B)

(C)

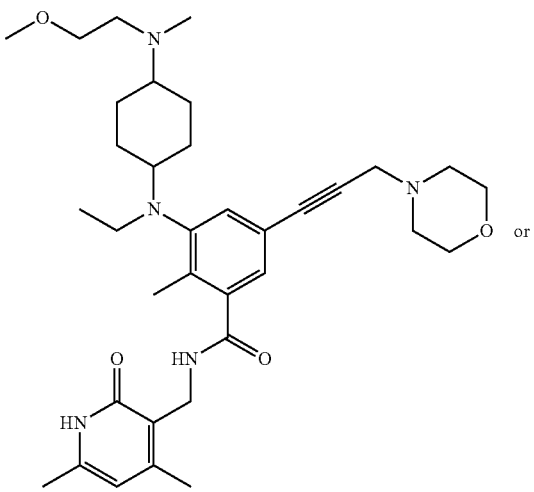

(D)

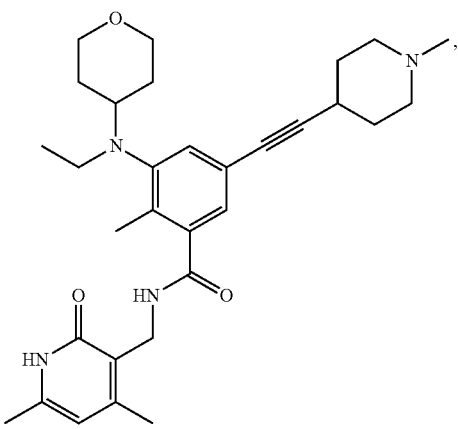

(E)

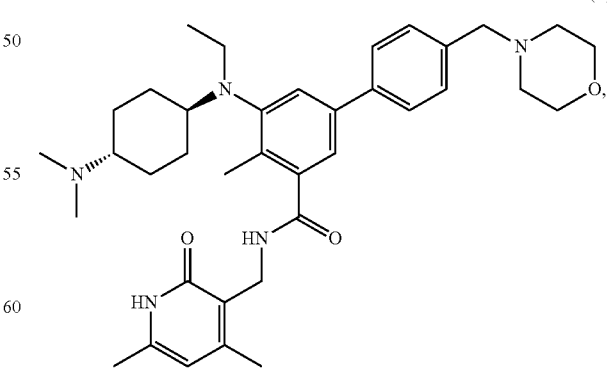

stereoisomers thereof or pharmaceutically acceptable salts and solvates thereof.

In certain embodiments, a compound that can be used in any methods presented here is Compound F:

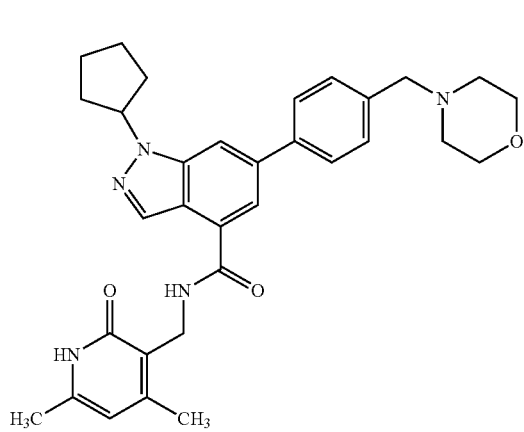

(F)

or pharmaceutically acceptable salts thereof.

In some embodiments, a compound (e.g., EZH2 inhibitor) that can be used in any methods presented here is GSK-126 having the following formula:

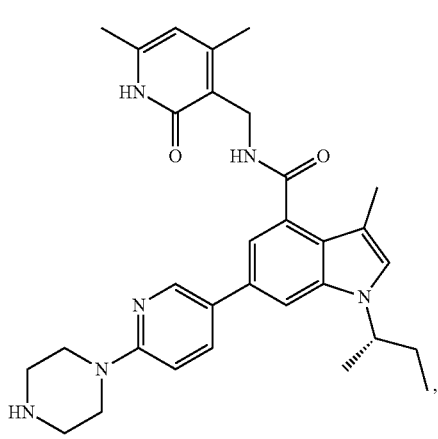 [SMILES: CC[C@H](C)n1cc(C)c2c(C(=O)NCc3c(C)cc(C)[nH]c3=O)cc(-c3ccc(N4CCNCC4)nc3)cc21]

stereoisomers thereof, or pharmaceutically acceptable salts or solvates thereof.

In certain embodiments, a compound that can be used in any methods presented here is Compound G:

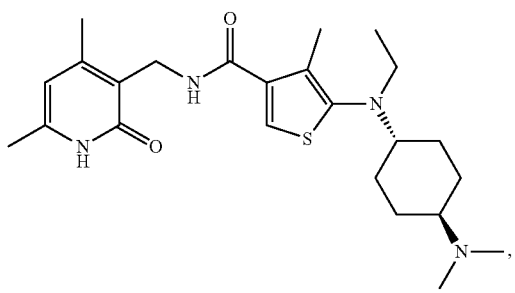

(G)

or stereoisomers thereof or pharmaceutically acceptable salts and solvates thereof.

In certain embodiments, a compound (e.g., EZH2 inhibitor) that can be used in any methods presented here is any of Compounds Ga-Gc:

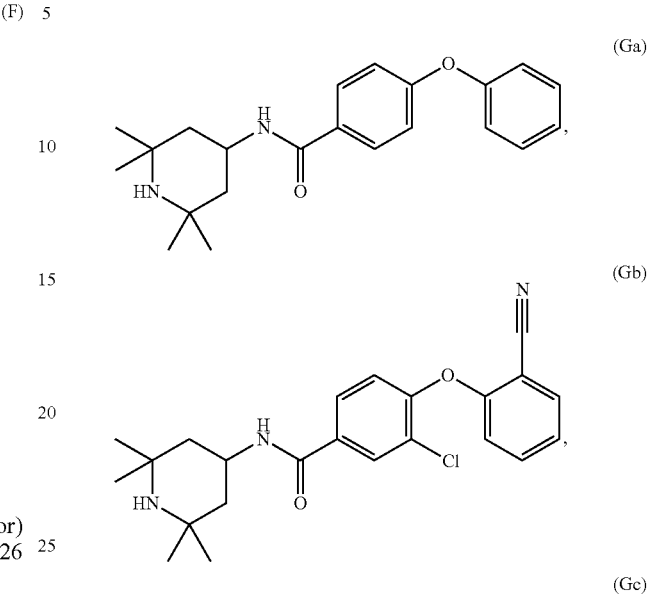

or a stereoisomer, pharmaceutically acceptable salt or solvate thereof.

EZH2 inhibitors of the disclosure may comprise, consist essentially of or consist of CPI-1205 or GSK343.

Additional suitable EZH2 inhibitors will be apparent to those skilled in the art. In some embodiments of the strategies, treatment modalities, methods, combinations, and compositions provided herein, the EZH2 inhibitor is an EZH2 inhibitor described in U.S Pat. No. 8,536,179 (describing GSK-126 among other compounds and corresponding to WO 2011/140324), the entire contents of each of which are incorporated herein by reference.

In some embodiments of the strategies, treatment modalities, methods, combinations, and compositions provided herein, the EZH2 inhibitor is an EZH2 inhibitor described in PCT/US2014/015706, published as WO 2014/124418, in PCT/US2013/025639, published as WO 2013/120104, and in U.S. Ser. No. 14/839,273, published as US 2015/0368229, the entire contents of each of which are incorporated herein by reference.

In one embodiment, the compound of the disclosure may be the compound itself, i.e., the free base or "naked" molecule. In another embodiment, the compound may be a salt thereof, e.g., a mono-HCl or tri-HCl salt, mono-HBr or tri-HBr salt of the naked molecule.

Representative compounds of Formula VIa of the disclosure include compounds listed in Table 1.
In Table 1, each occurrence of
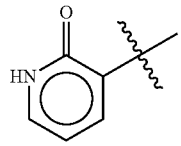
should be construed as
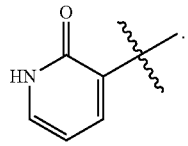
TABLE 1
| Compound Number | Structure | MS (M + 1)+ |
|---|---|---|
| 1 | 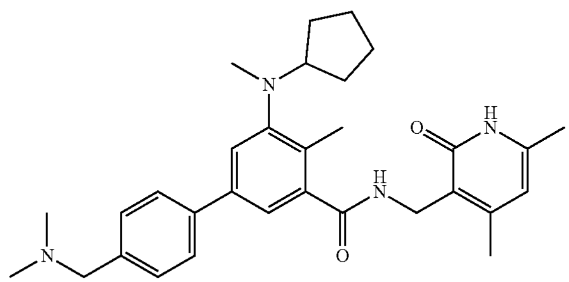 | 501.39 |
| 2 | 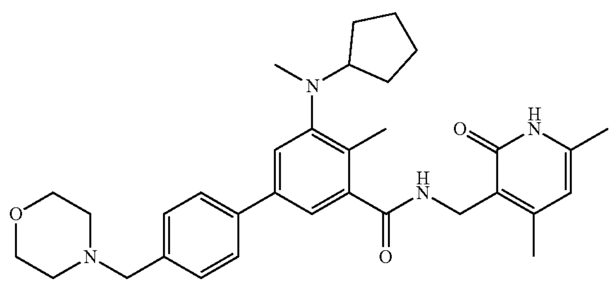 [SMILES: Cc1cc(C)c(CNC(=O)c2cc(-c3ccc(CN4CCOCC4)cc3)cc(N(C)C3CCCC3)c2C)c(=O)[nH]1] | 543.22 |
| 3 | 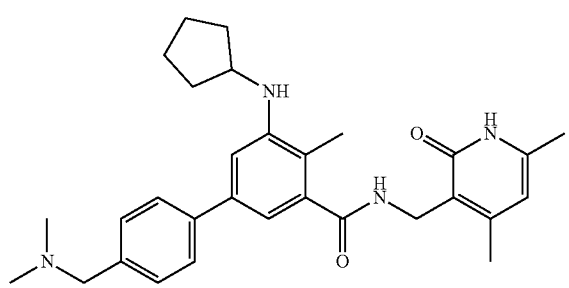 | 486.21 |
| 4 | 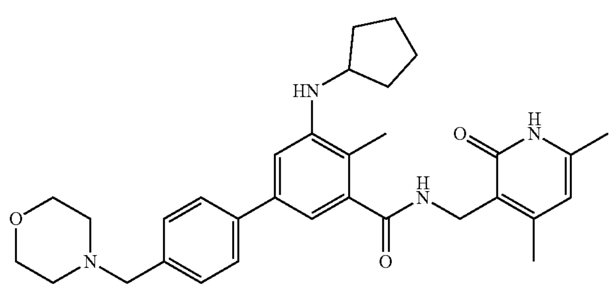 [SMILES: Cc1cc(C)c(CNC(=O)c2cc(-c3ccc(CN4CCOCC4)cc3)cc(NC3CCCC3)c2C)c(=O)[nH]1] | 529.30 |

TABLE 1-continued

| Compound Number | Structure | MS (M + 1)+ |
|---|---|---|
| 11 | 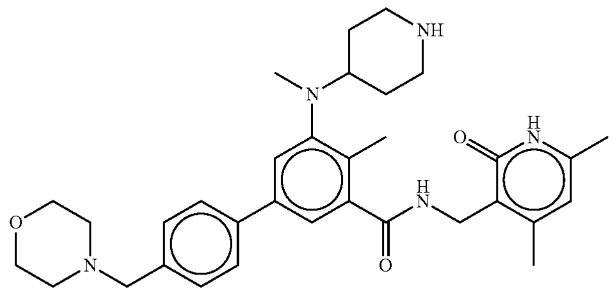 | 558.45 |
| 12 | 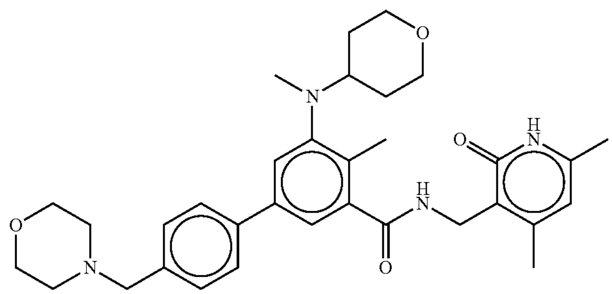 | 559.35 |
| 13 | 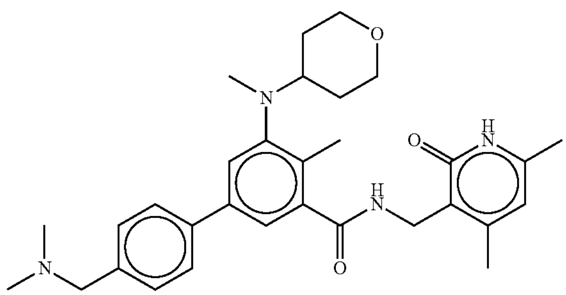 | 517.3 |
| 14 | 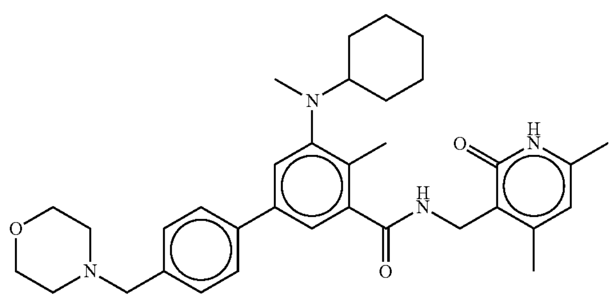 | 557.4 |
| 16 | 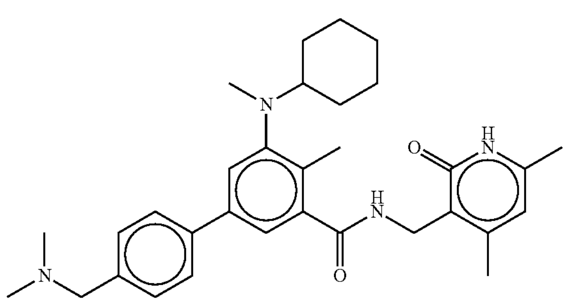 | 515.4 |

TABLE 1-continued

| Compound Number | Structure | MS (M + 1)+ |
|---|---|---|
| 20 | 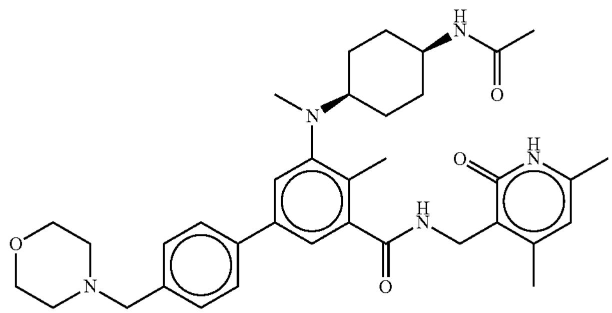 | 614.4 |
| 21 | 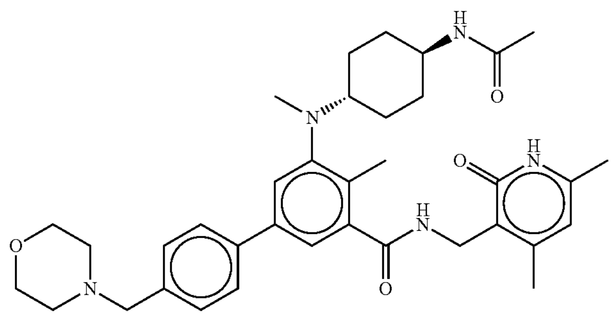 | 614.4 |
| 27 | 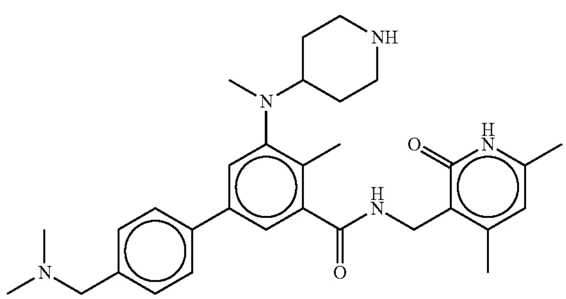 | 516.35 |
| 36 | 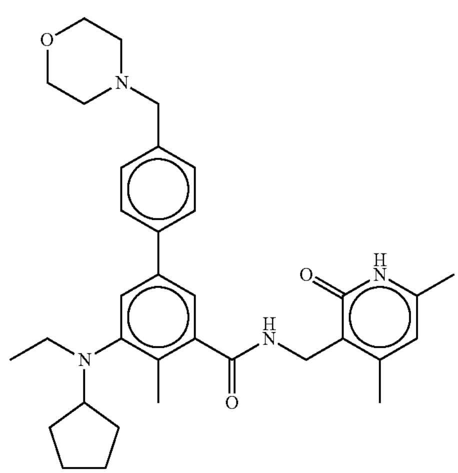 | 557.35 |

TABLE 1-continued

| Compound Number | Structure | MS (M + 1)+ |
|---|---|---|
| 39 | 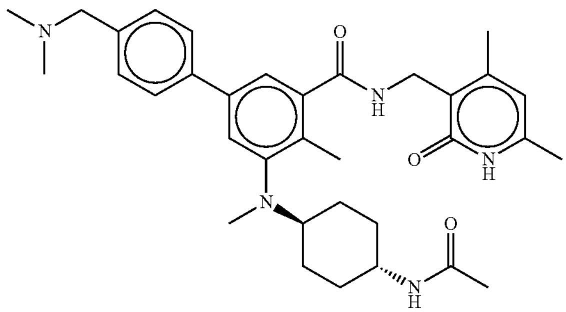 | 572.35 |
| 40 | 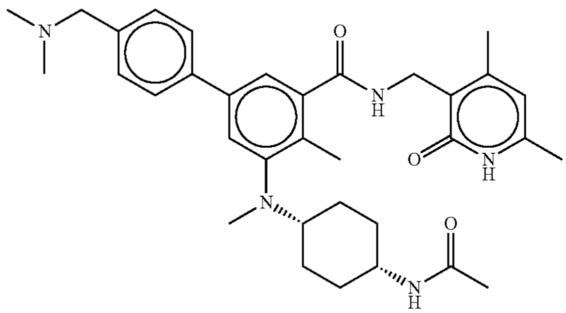 | 572.35 |
| 42 | 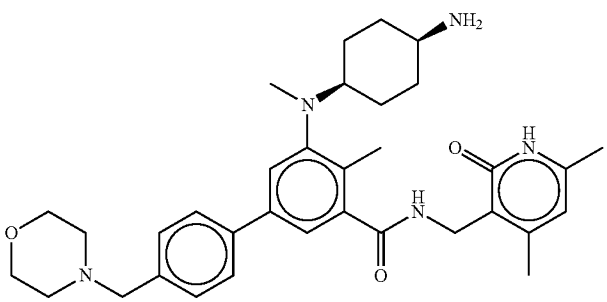 | 572.4 |
| 43 | 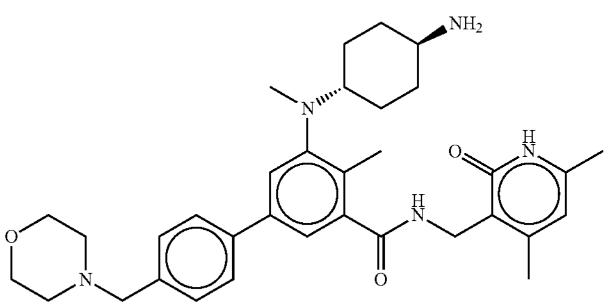 | 572.6 |

TABLE 1-continued

| Compound Number | Structure | MS (M + 1)+ |
|---|---|---|
| 44 | 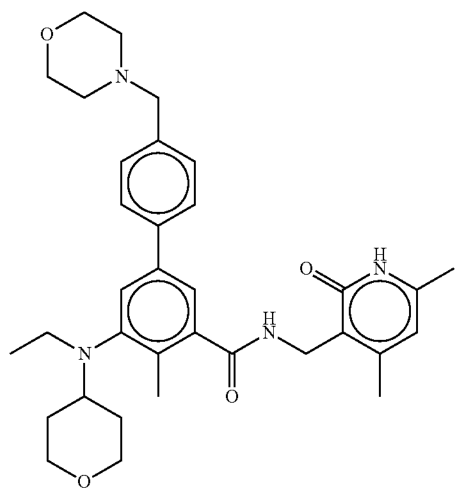 | 573.40 |
| 47 | 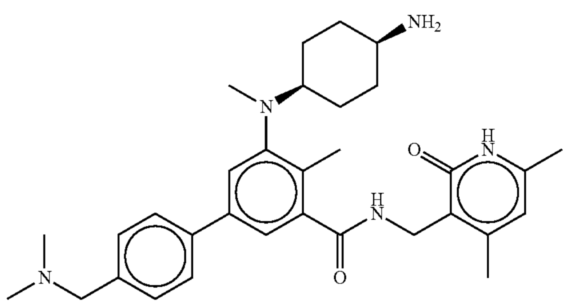 | 530.35 |
| 59 | 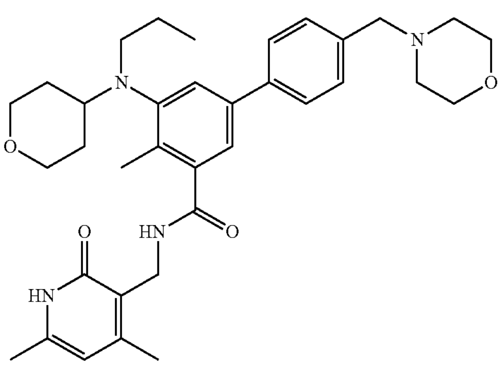 [SMILES: CCCN(c1cc(-c2ccc(CN3CCOCC3)cc2)cc(C(=O)NCc2c(C)cc(C)[nH]c2=O)c1C)C1CCOCC1] | 587.40 |
| 60 | 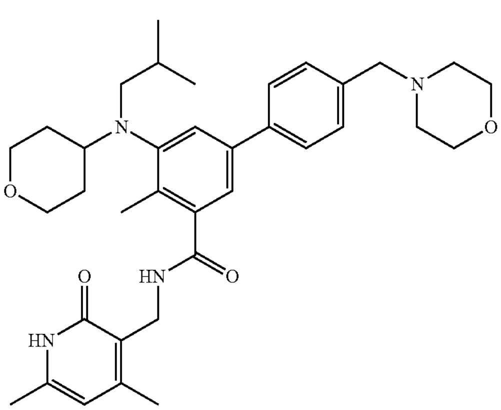 [SMILES: Cc1cc(C)c(CNC(=O)c2cc(-c3ccc(CN4CCOCC4)cc3)cc(N(CC(C)C)C3CCOCC3)c2C)c(=O)[nH]1] | 601.30 |

TABLE 1-continued

| Compound Number | Structure | MS (M + 1)+ |
|---|---|---|
| 61 | 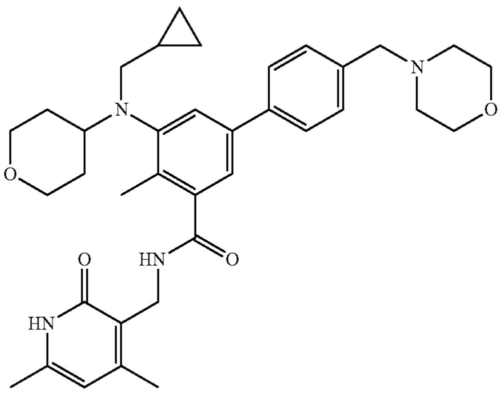 [SMILES: Cc1cc(C)c(CNC(=O)c2cc(-c3ccc(CN4CCOCC4)cc3)cc(N(CC3CC3)C3CCOCC3)c2C)c(=O)[nH]1] | 599.35 |
| 62 | 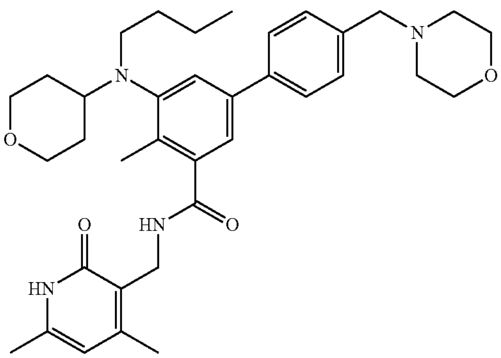 [SMILES: CCCCN(c1cc(-c2ccc(CN3CCOCC3)cc2)cc(C(=O)NCc2c(C)cc(C)[nH]c2=O)c1C)C1CCOCC1] | 601.35 |
| 63 | 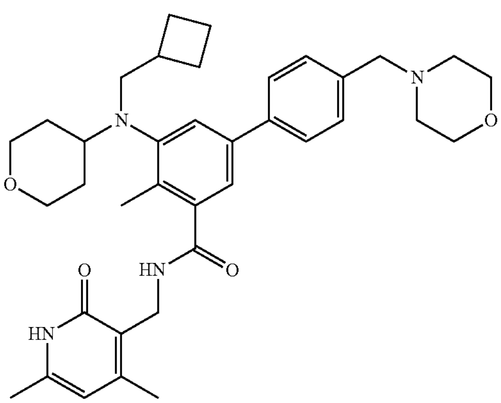 [SMILES: Cc1cc(C)c(CNC(=O)c2cc(-c3ccc(CN4CCOCC4)cc3)cc(N(CC3CCC3)C3CCOCC3)c2C)c(=O)[nH]1] | 613.35 |
| 65 | 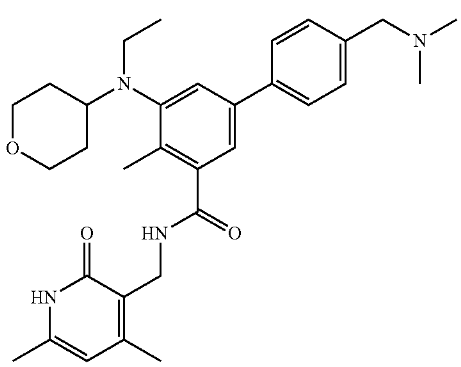 [SMILES: CCN(c1cc(-c2ccc(CN(C)C)cc2)cc(C(=O)NCc2c(C)cc(C)[nH]c2=O)c1C)C1CCOCC1] | 531.30 |

TABLE 1-continued

| Compound Number | Structure | MS (M + 1)+ |
|---|---|---|
| 66 | 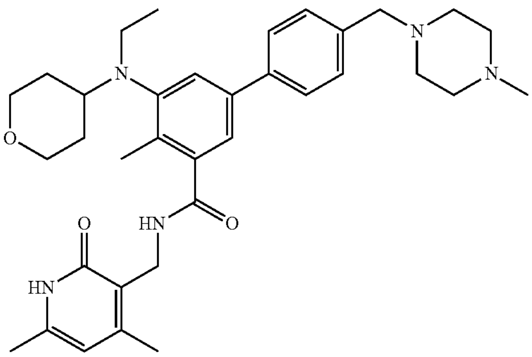 [SMILES: CCN(c1cc(-c2ccc(CN3CCN(C)CC3)cc2)cc(C(=O)NCc2c(C)cc(C)[nH]c2=O)c1C)C1CCOCC1] | 586.40 |
| 67 | 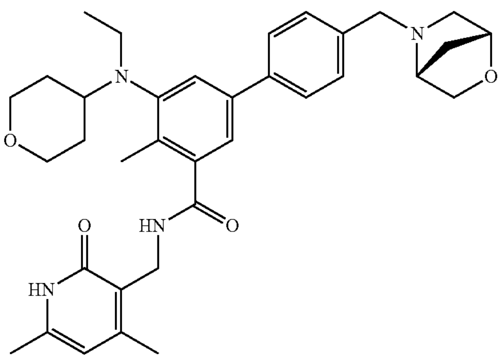 [SMILES: CCN(c1cc(-c2ccc(CN3C[C@H]4C[C@@H]3CO4)cc2)cc(C(=O)NCc2c(C)cc(C)[nH]c2=O)c1C)C1CCOCC1] | 585.25 |
| 68 | 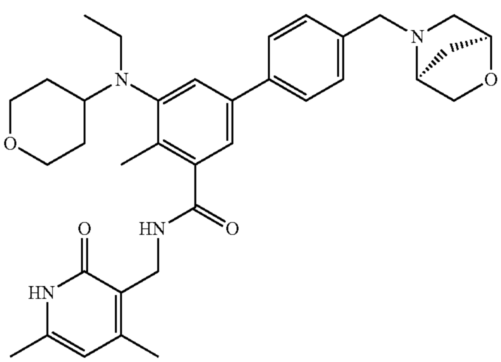 [SMILES: CCN(c1cc(-c2ccc(CN3C[C@@H]4C[C@H]3CO4)cc2)cc(C(=O)NCc2c(C)cc(C)[nH]c2=O)c1C)C1CCOCC1] | 585.35 |
| 69 | 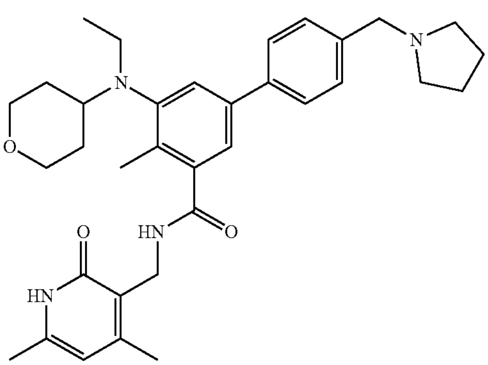 [SMILES: CCN(c1cc(-c2ccc(CN3CCCC3)cc2)cc(C(=O)NCc2c(C)cc(C)[nH]c2=O)c1C)C1CCOCC1] | 557.25 |

TABLE 1-continued
| Compound Number | Structure | MS (M + 1)+ |
|---|---|---|
| 70 | 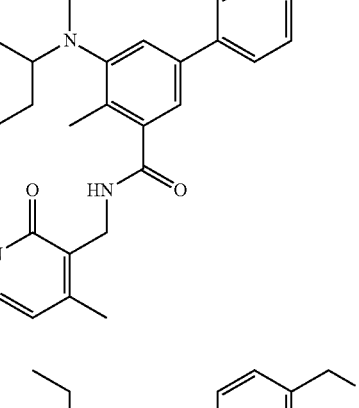 | 573.40 |
| 71 | 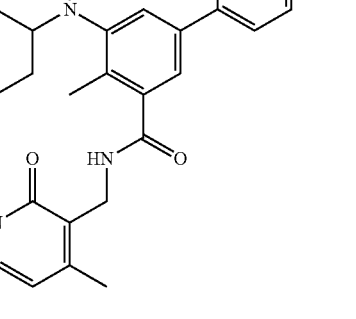 | 573.40 |
| 72 | 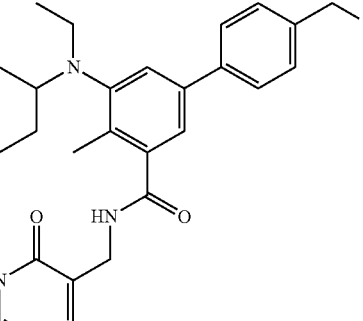 | 575.35 |
| 73 | 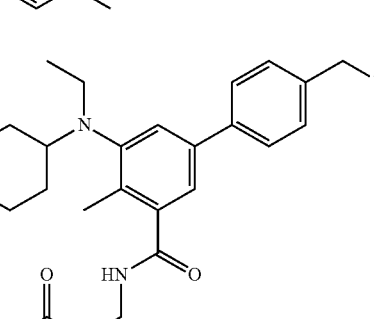 | 572.10 |

TABLE 1-continued

| Compound Number | Structure | MS (M + 1)+ |
|---|---|---|
| 74 | 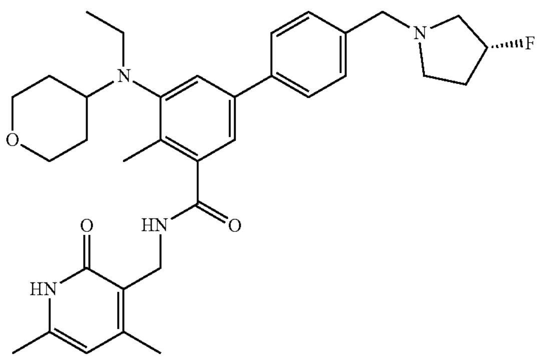 [SMILES: CCN(c1cc(-c2ccc(CN3CC[C@@H](F)C3)cc2)cc(C(=O)NCc2c(C)cc(C)[nH]c2=O)c1C)C1CCOCC1] | 575.35 |
| 75 | 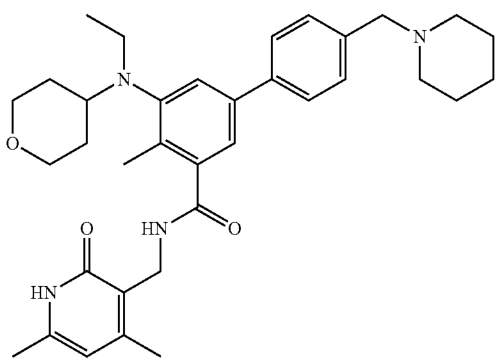 [SMILES: CCN(c1cc(-c2ccc(CN3CCCCC3)cc2)cc(C(=O)NCc2c(C)cc(C)[nH]c2=O)c1C)C1CCOCC1] | 571.25 |
| 76 | 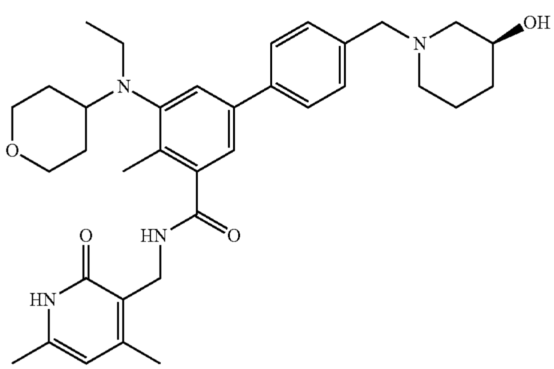 [SMILES: CCN(c1cc(-c2ccc(CN3CCC[C@H](O)C3)cc2)cc(C(=O)NCc2c(C)cc(C)[nH]c2=O)c1C)C1CCOCC1] | 587.40 |
| 77 | 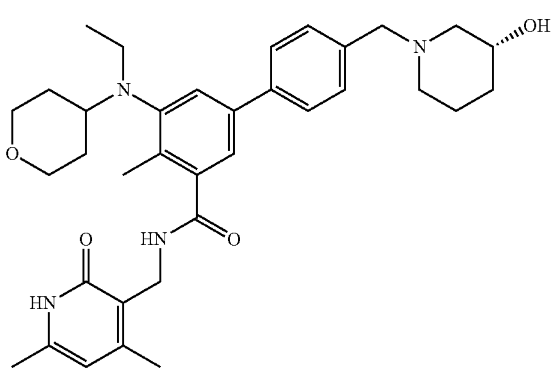 [SMILES: CCN(c1cc(-c2ccc(CN3CCC[C@@H](O)C3)cc2)cc(C(=O)NCc2c(C)cc(C)[nH]c2=O)c1C)C1CCOCC1] | 587.45 |

TABLE 1-continued

| Compound Number | Structure | MS (M + 1)+ |
|---|---|---|
| 78 | 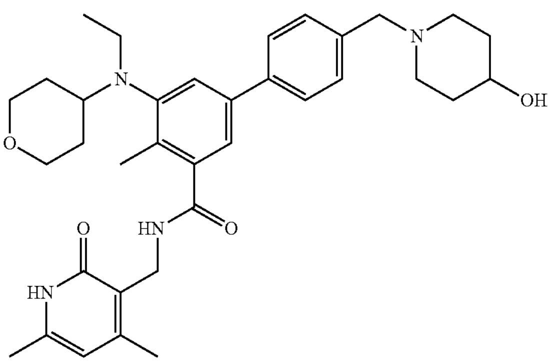 [SMILES: CCN(c1cc(-c2ccc(CN3CCC(O)CC3)cc2)cc(C(=O)NCc2c(C)cc(C)[nH]c2=O)c1C)C1CCOCC1] | 587.20 |
| 79 | 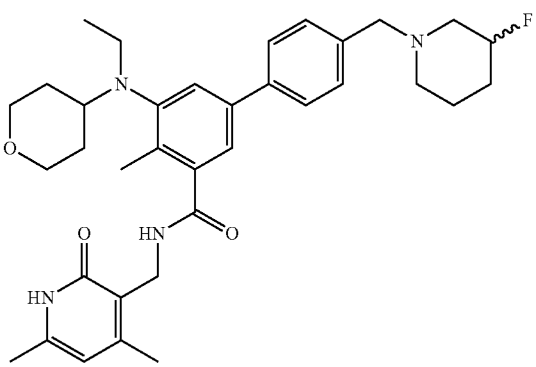 [SMILES: CCN(c1cc(-c2ccc(CN3CCCC(F)C3)cc2)cc(C(=O)NCc2c(C)cc(C)[nH]c2=O)c1C)C1CCOCC1] | 589.35 |
| 80 | 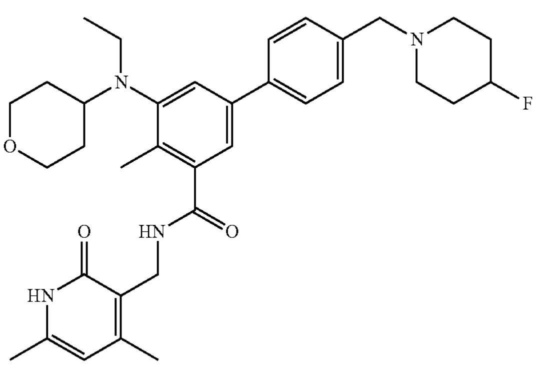 [SMILES: CCN(c1cc(-c2ccc(CN3CCC(F)CC3)cc2)cc(C(=O)NCc2c(C)cc(C)[nH]c2=O)c1C)C1CCOCC1] | 589.30 |
| 81 | 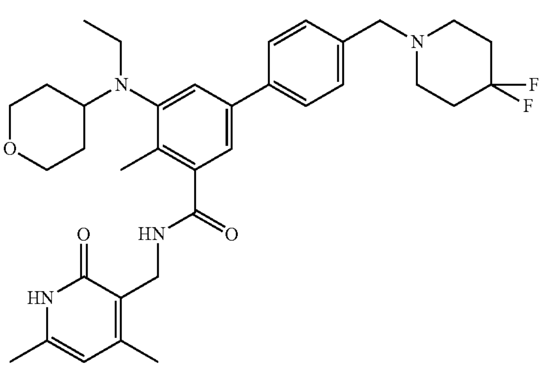 [SMILES: CCN(c1cc(-c2ccc(CN3CCC(F)(F)CC3)cc2)cc(C(=O)NCc2c(C)cc(C)[nH]c2=O)c1C)C1CCOCC1] | 607.35 |

TABLE 1-continued

| Compound Number | Structure | MS (M + 1)+ |
|---|---|---|
| 82 | 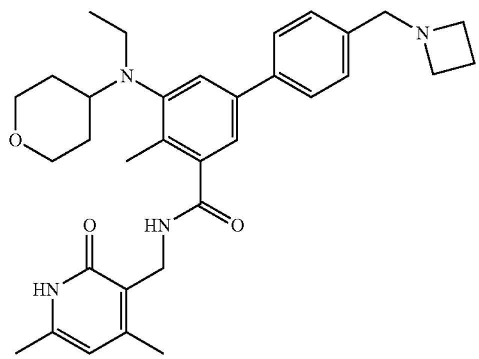 [SMILES: CCN(c1cc(-c2ccc(CN3CCC3)cc2)cc(C(=O)NCc2c(C)cc(C)[nH]c2=O)c1C)C1CCOCC1] | 543.40 |
| 83 | 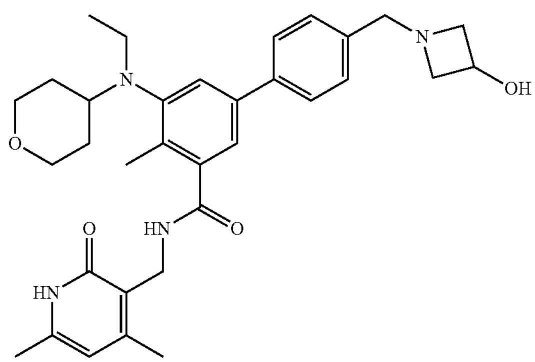 [SMILES: CCN(c1cc(-c2ccc(CN3CC(O)C3)cc2)cc(C(=O)NCc2c(C)cc(C)[nH]c2=O)c1C)C1CCOCC1] | 559.80 |
| 84 | 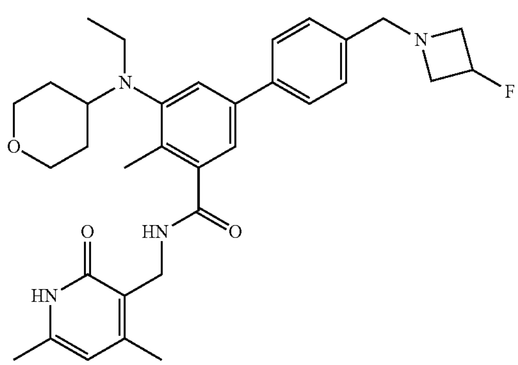 [SMILES: CCN(c1cc(-c2ccc(CN3CC(F)C3)cc2)cc(C(=O)NCc2c(C)cc(C)[nH]c2=O)c1C)C1CCOCC1] | 561.25 |
| 85 | 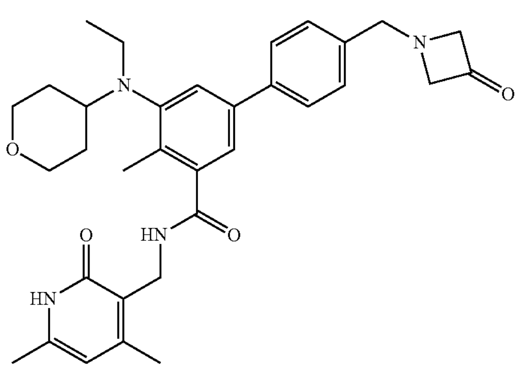 [SMILES: CCN(c1cc(-c2ccc(CN3CC(=O)C3)cc2)cc(C(=O)NCc2c(C)cc(C)[nH]c2=O)c1C)C1CCOCC1] | |

TABLE 1-continued

| Compound Number | Structure | MS (M + 1)+ |
|---|---|---|
| 86 | 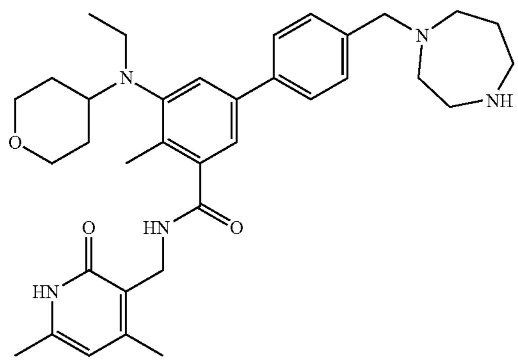 [SMILES: CCN(c1cc(-c2ccc(CN3CCCNCC3)cc2)cc(C(=O)NCc2c(C)cc(C)[nH]c2=O)c1C)C1CCOCC1] | 585.37 |
| 87 | 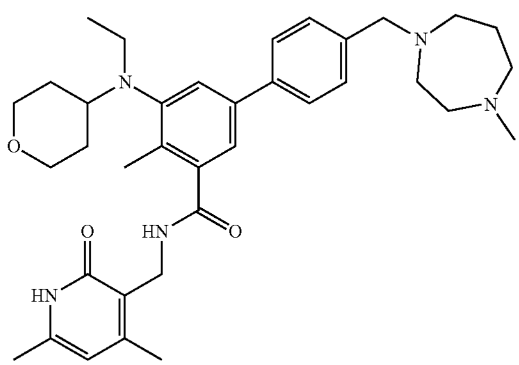 [SMILES: CCN(c1cc(-c2ccc(CN3CCCN(C)CC3)cc2)cc(C(=O)NCc2c(C)cc(C)[nH]c2=O)c1C)C1CCOCC1] | 600.30 |
| 88 | 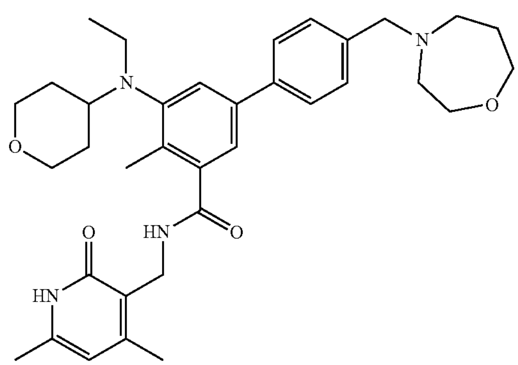 [SMILES: CCN(c1cc(-c2ccc(CN3CCCOCC3)cc2)cc(C(=O)NCc2c(C)cc(C)[nH]c2=O)c1C)C1CCOCC1] | 587.40 |
| 89 | 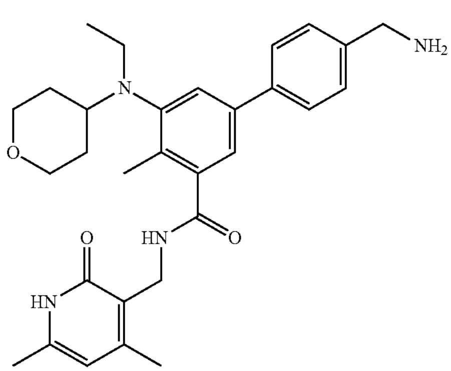 [SMILES: CCN(c1cc(-c2ccc(CN)cc2)cc(C(=O)NCc2c(C)cc(C)[nH]c2=O)c1C)C1CCOCC1] | 503.40 |

TABLE 1-continued

| Compound Number | Structure | MS (M + 1)+ |
|---|---|---|
| 90 | 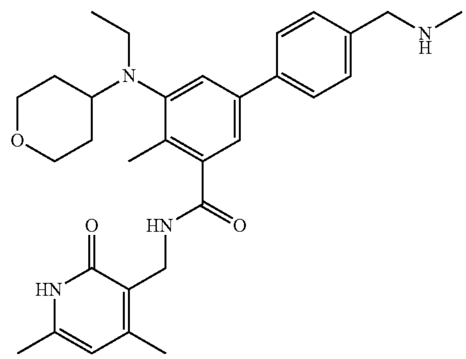 [SMILES: CCN(c1cc(-c2ccc(CNC)cc2)cc(C(=O)NCc2c(C)cc(C)[nH]c2=O)c1C)C1CCOCC1] | 517.30 |
| 91 | 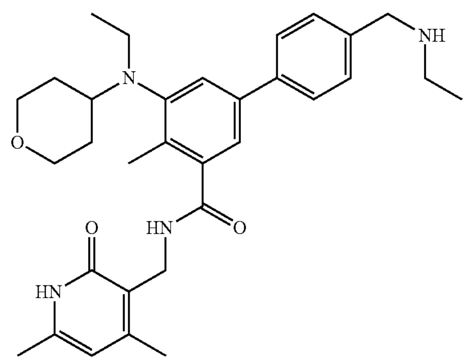 [SMILES: CCNCc1ccc(-c2cc(C(=O)NCc3c(C)cc(C)[nH]c3=O)c(C)c(N(CC)C3CCOCC3)c2)cc1] | 531.35 |
| 92 | 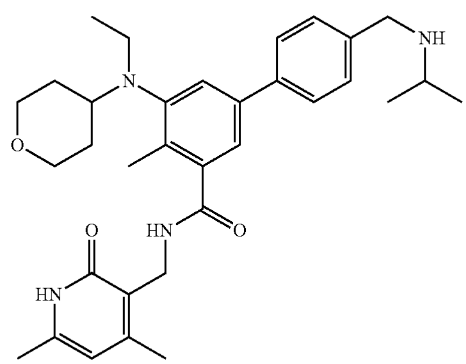 [SMILES: CCN(c1cc(-c2ccc(CNC(C)C)cc2)cc(C(=O)NCc2c(C)cc(C)[nH]c2=O)c1C)C1CCOCC1] | 545.40 |
| 93 | 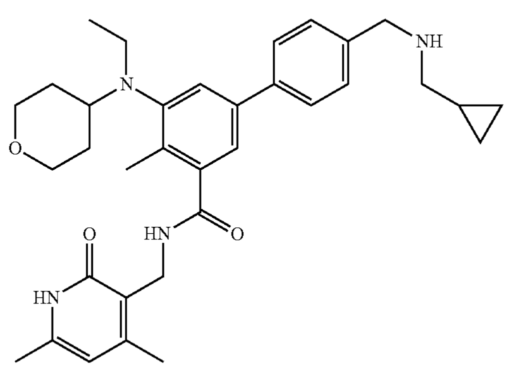 [SMILES: CCN(c1cc(-c2ccc(CNCC3CC3)cc2)cc(C(=O)NCc2c(C)cc(C)[nH]c2=O)c1C)C1CCOCC1] | 557.35 |

TABLE 1-continued

| Compound Number | Structure | MS (M + 1)+ |
|---|---|---|
| 94 | 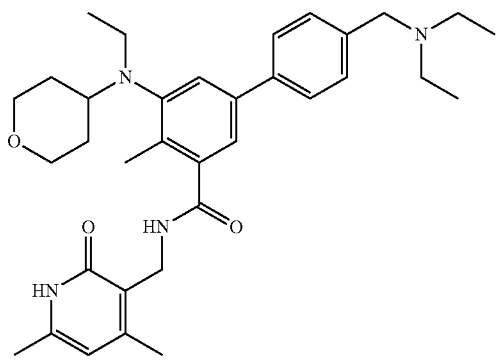 [SMILES: CCN(CC)Cc1ccc(-c2cc(C(=O)NCc3c(C)cc(C)[nH]c3=O)c(C)c(N(CC)C3CCOCC3)c2)cc1] | 559.20 |
| 95 | 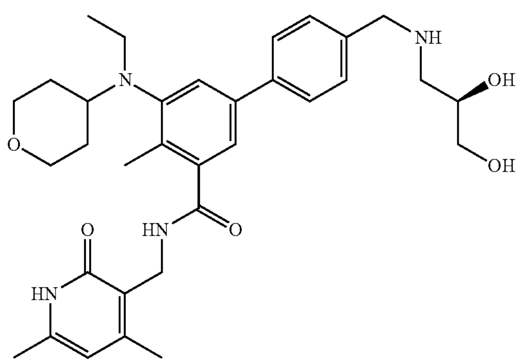 [SMILES: CCN(c1cc(-c2ccc(CNC[C@@H](O)CO)cc2)cc(C(=O)NCc2c(C)cc(C)[nH]c2=O)c1C)C1CCOCC1] | 599.35 (M + Na) |
| 96 | 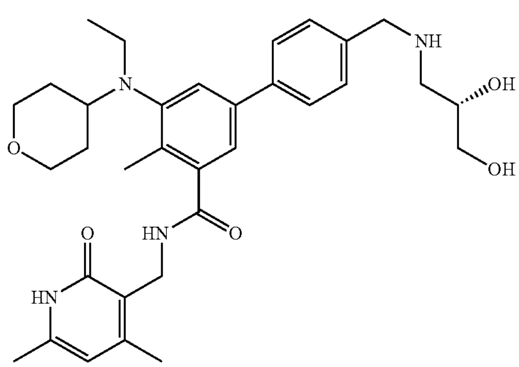 [SMILES: CCN(c1cc(-c2ccc(CNC[C@H](O)CO)cc2)cc(C(=O)NCc2c(C)cc(C)[nH]c2=O)c1C)C1CCOCC1] | 577.25 |
| 97 | 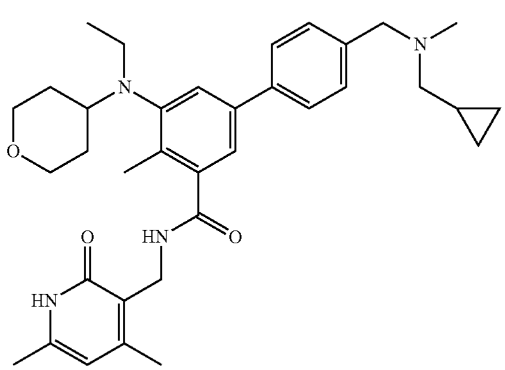 [SMILES: CCN(c1cc(-c2ccc(CN(C)CC3CC3)cc2)cc(C(=O)NCc2c(C)cc(C)[nH]c2=O)c1C)C1CCOCC1] | 571.40 |

TABLE 1-continued

| Compound Number | Structure | MS (M + 1)+ |
|---|---|---|
| 98 | 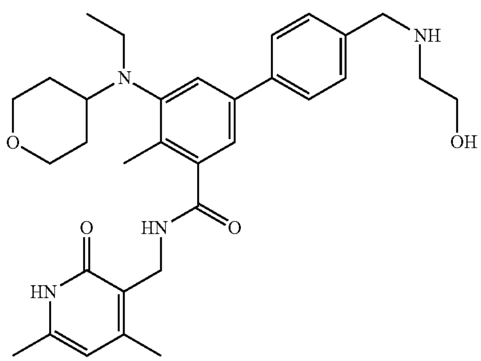 [SMILES: CCN(c1cc(-c2ccc(CNCCO)cc2)cc(C(=O)NCc2c(C)cc(C)[nH]c2=O)c1C)C1CCOCC1] | 547.35 |
| 99 | 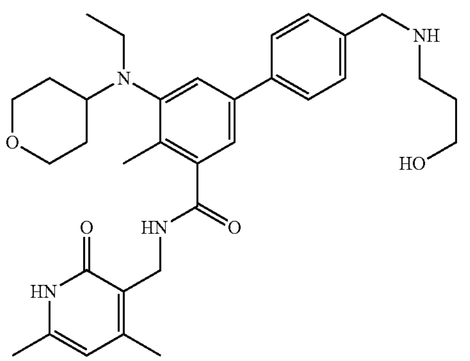 [SMILES: CCN(c1cc(-c2ccc(CNCCCO)cc2)cc(C(=O)NCc2c(C)cc(C)[nH]c2=O)c1C)C1CCOCC1] | 561.30 |
| 100 | 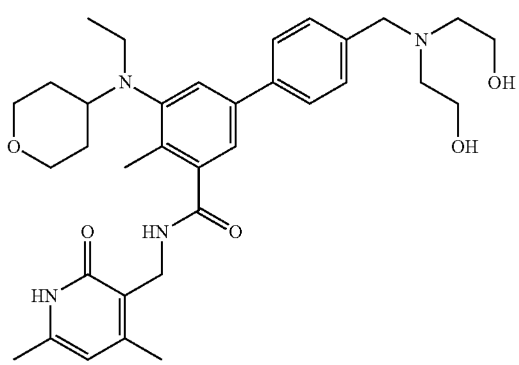 [SMILES: CCN(c1cc(-c2ccc(CN(CCO)CCO)cc2)cc(C(=O)NCc2c(C)cc(C)[nH]c2=O)c1C)C1CCOCC1] | 591.25 |
| 101 | 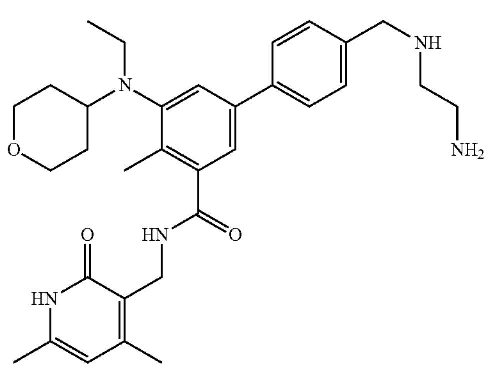 [SMILES: CCN(c1cc(-c2ccc(CNCCN)cc2)cc(C(=O)NCc2c(C)cc(C)[nH]c2=O)c1C)C1CCOCC1] | 546.35 |

TABLE 1-continued

| Compound Number | Structure | MS (M + 1)+ |
|---|---|---|
| 102 | 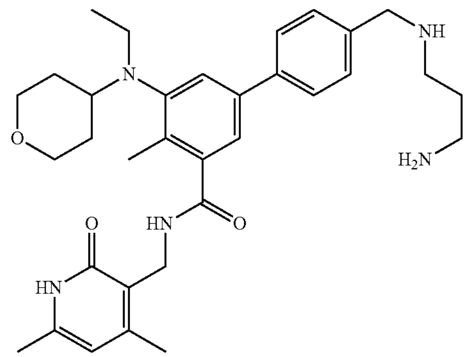 [SMILES: CCN(c1cc(-c2ccc(CNCCCN)cc2)cc(C(=O)NCc2c(C)cc(C)[nH]c2=O)c1C)C1CCOCC1] | 560.20 |
| 103 | 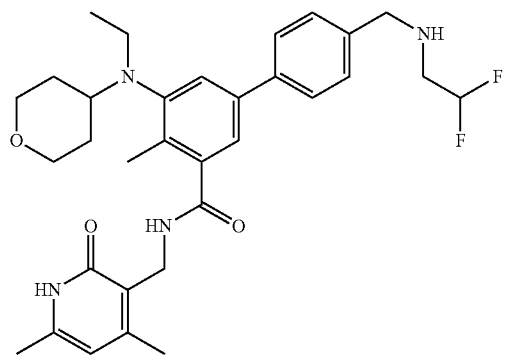 [SMILES: CCN(c1cc(-c2ccc(CNCC(F)F)cc2)cc(C(=O)NCc2c(C)cc(C)[nH]c2=O)c1C)C1CCOCC1] | 567.30 |
| 104 | 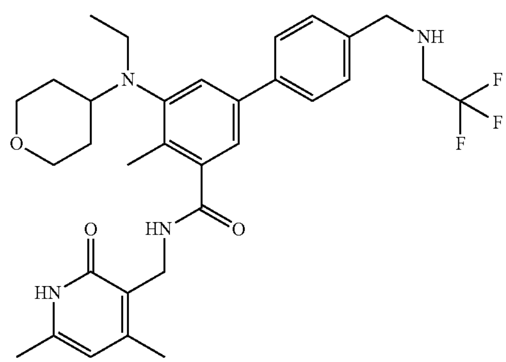 [SMILES: CCN(c1cc(-c2ccc(CNCC(F)(F)F)cc2)cc(C(=O)NCc2c(C)cc(C)[nH]c2=O)c1C)C1CCOCC1] | 585.25 |
| 105 | 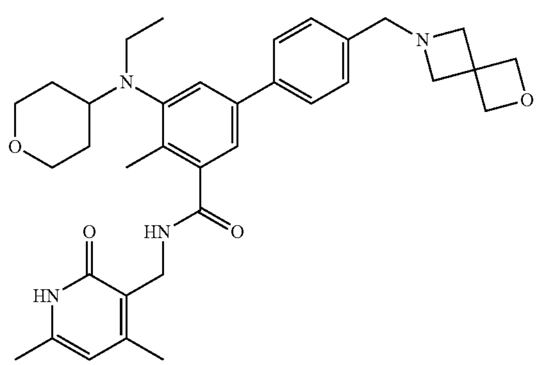 [SMILES: CCN(c1cc(-c2ccc(CN3CC4(COC4)C3)cc2)cc(C(=O)NCc2c(C)cc(C)[nH]c2=O)c1C)C1CCOCC1] | 585.40 |

TABLE 1-continued

| Compound Number | Structure | MS (M + 1)+ |
|---|---|---|
| 107 | 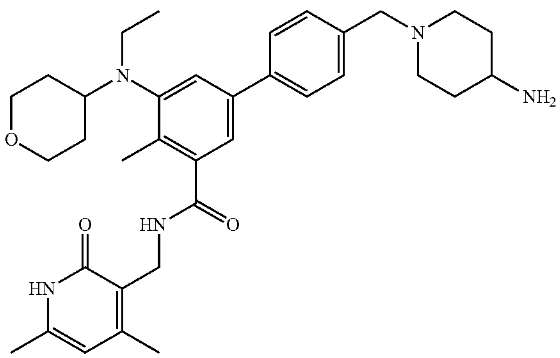 [SMILES: CCN(c1cc(-c2ccc(CN3CCC(N)CC3)cc2)cc(C(=O)NCc2c(C)cc(C)[nH]c2=O)c1C)C1CCOCC1] | |
| 108 | 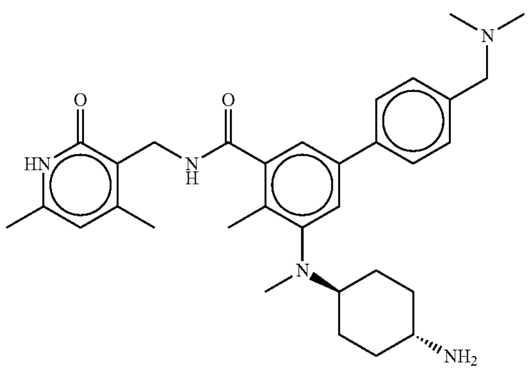 | 530.35 |
| 114 | 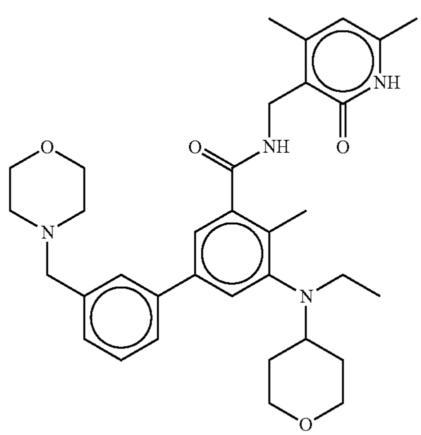 | 573.25 |
| 115 | 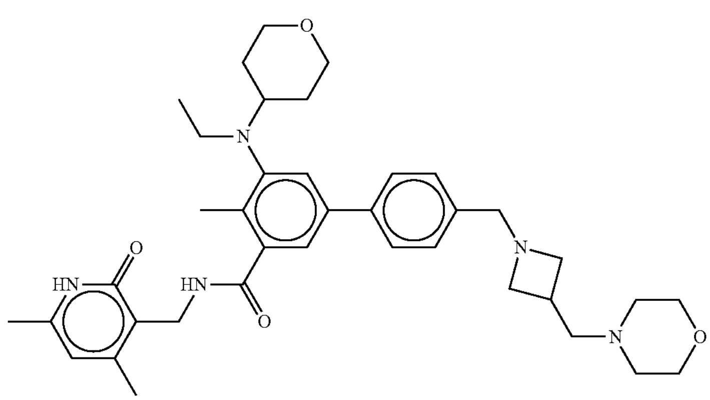 | 642.45 |

TABLE 1-continued

| Compound Number | Structure | MS (M + 1)+ |
|---|---|---|
| 116 | 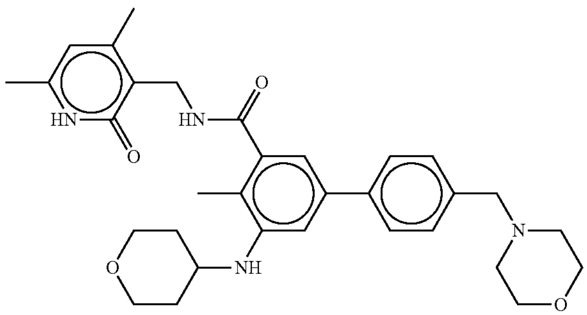 | 545.15 |
| 117 | 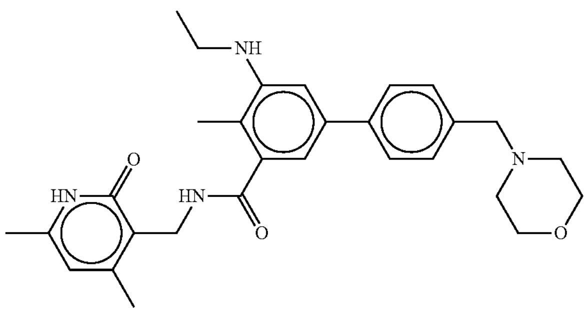 | 489.20 |
| 119 | 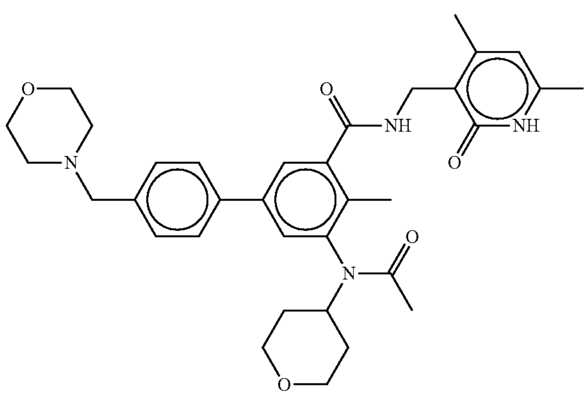 | 609.35 |
| 122 | 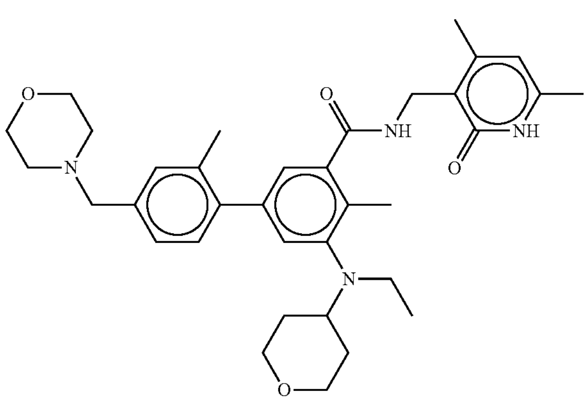 | 587.55 |

TABLE 1-continued

| Compound Number | Structure | MS (M + 1)+ |
|---|---|---|
| 124 | 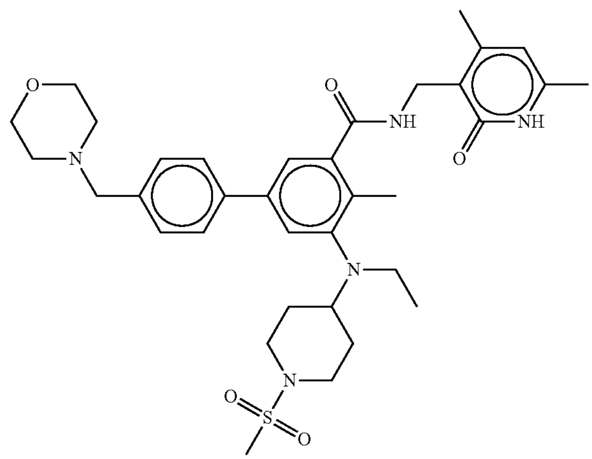 | 650.85 |
| 125 | 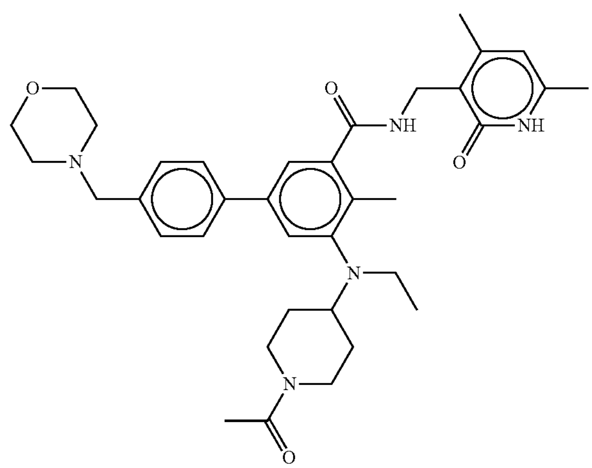 | 614.75 |
| 126 | 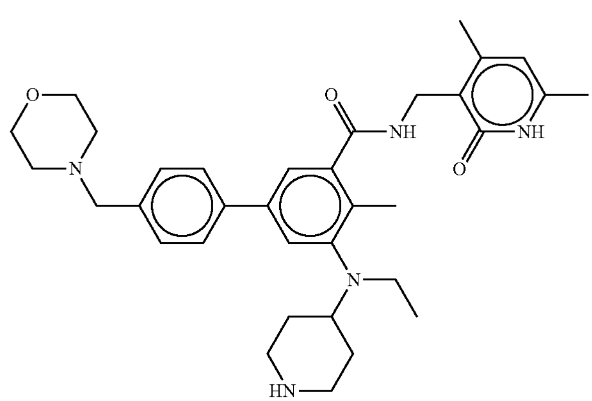 | 572.35 |

TABLE 1-continued

| Compound Number | Structure | MS (M + 1)+ |
|---|---|---|
| 127 | 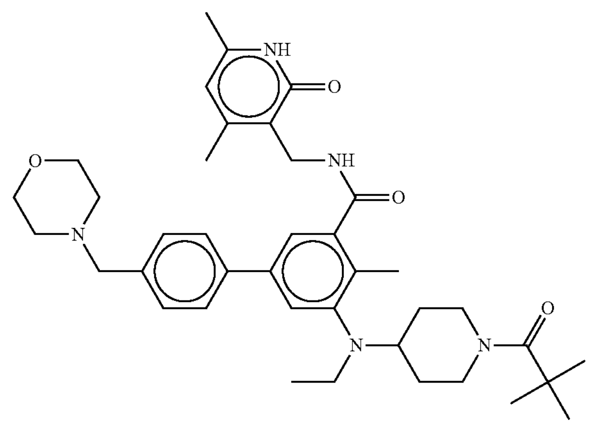 | 656.65 |
| 128 | 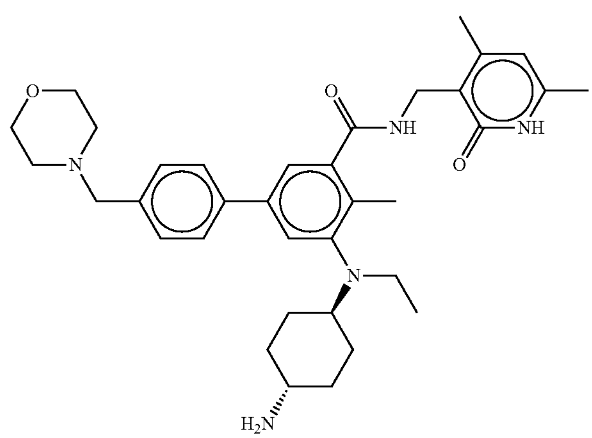 | 586.45 |
| 129 | 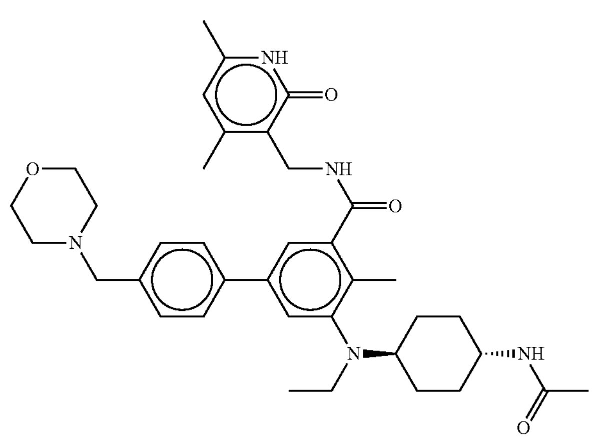 | 628.35 |

TABLE 1-continued

| Compound Number | Structure | MS (M + 1)+ |
|---|---|---|
| 130 | 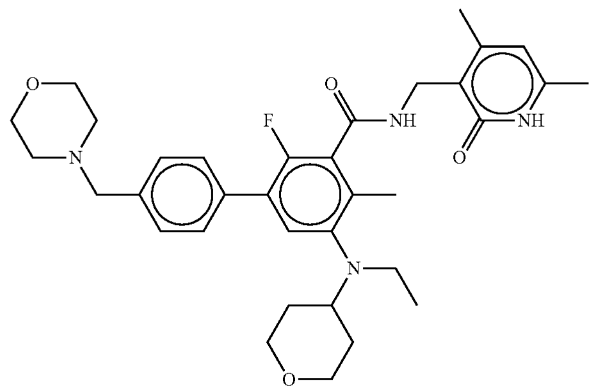 | 591.2 |
| 131 | 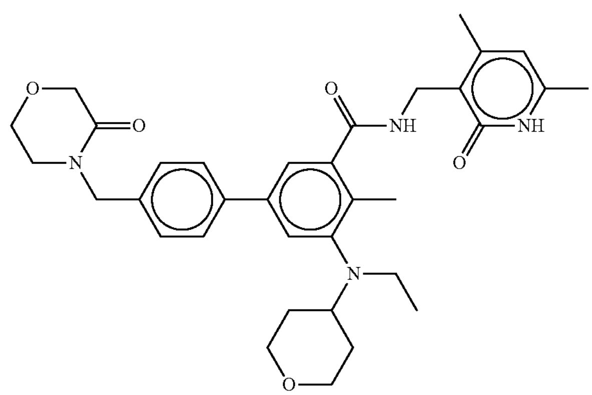 | 587.35 |
| 132 | 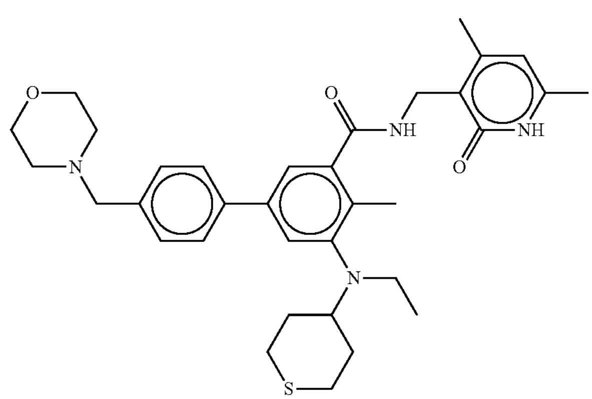 | 589.25 |

TABLE 1-continued

| Compound Number | Structure | MS (M + 1)+ |
|---|---|---|
| 133 | 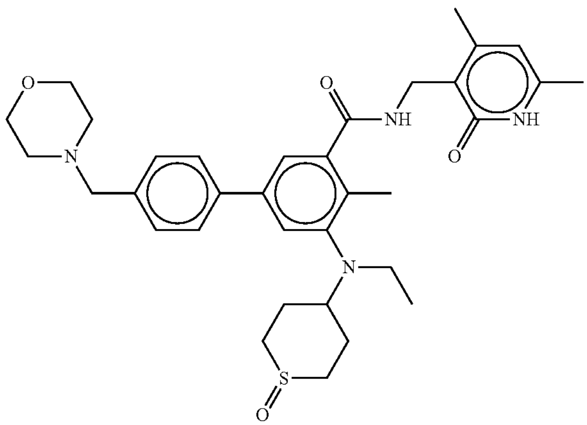 | 605.25 |
| 135 | 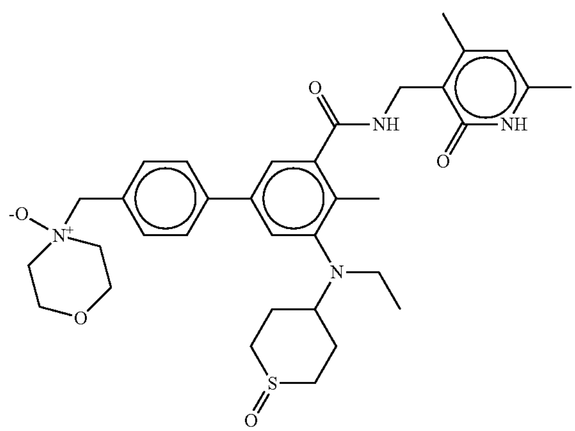 | 621.40 |
| 136 | 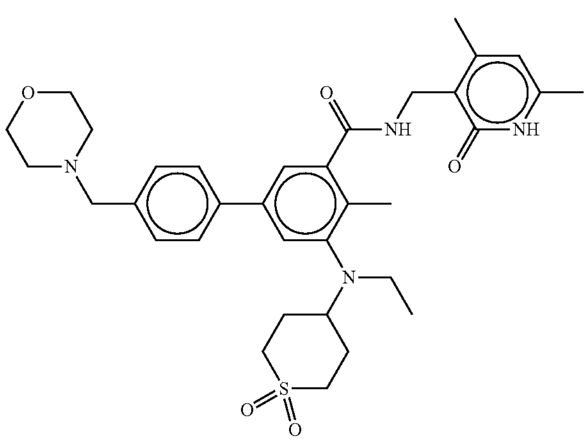 | 621.45 |

TABLE 1-continued

| Compound Number | Structure | MS (M + 1)+ |
|---|---|---|
| 137 | 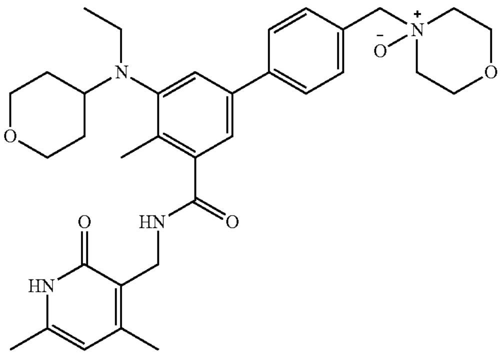 [SMILES: CCN(c1cc(-c2ccc(C[N+]3([O-])CCOCC3)cc2)cc(C(=O)NCc2c(C)cc(C)[nH]c2=O)c1C)C1CCOCC1] | 589.35 |
| 138 | 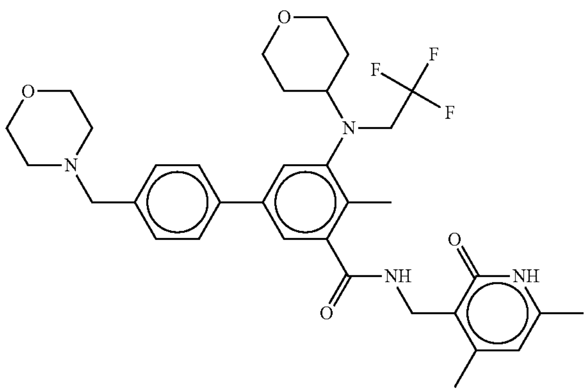 | 627.5 |
| 141 | 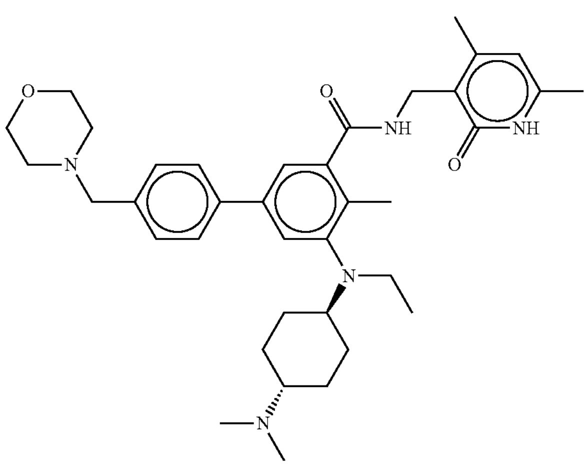 | 614.65 |

TABLE 1-continued

| Compound Number | Structure | MS (M + 1)+ |
|---|---|---|
| 142 | 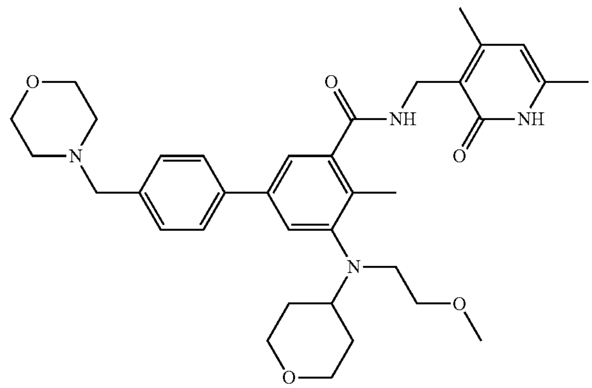 [SMILES: COCCN(c1cc(-c2ccc(CN3CCOCC3)cc2)cc(C(=O)NCc2c(C)cc(C)[nH]c2=O)c1C)C1CCOCC1] | 603.45 |
| 143 | 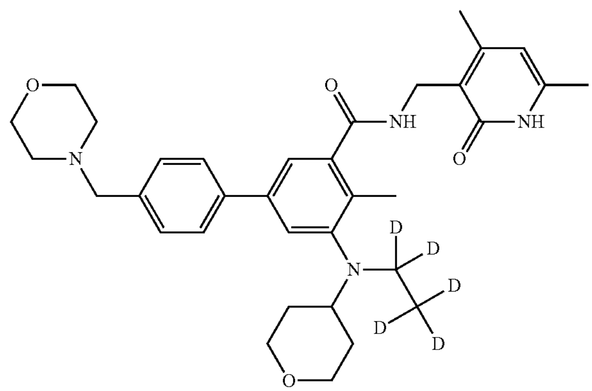 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1] | 578.35 |
| 144 | 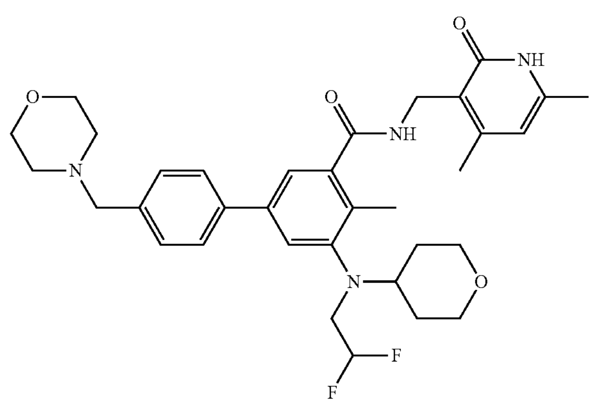 [SMILES: Cc1cc(C)c(CNC(=O)c2cc(-c3ccc(CN4CCOCC4)cc3)cc(N(CC(F)F)C3CCOCC3)c2C)c(=O)[nH]1] | 609.15 |
| 146 | 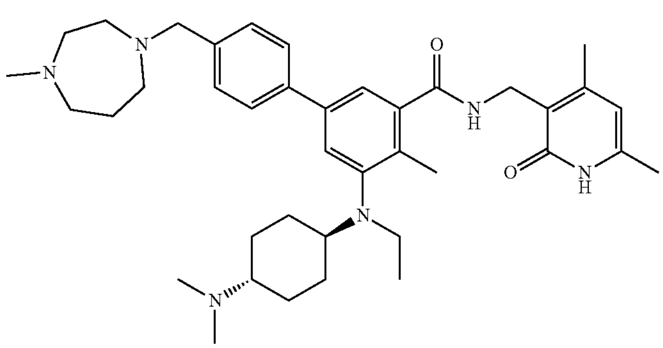 | 641.50 |

TABLE 1-continued

| Compound Number | Structure | MS (M + 1)+ |
|---|---|---|
| 178 | 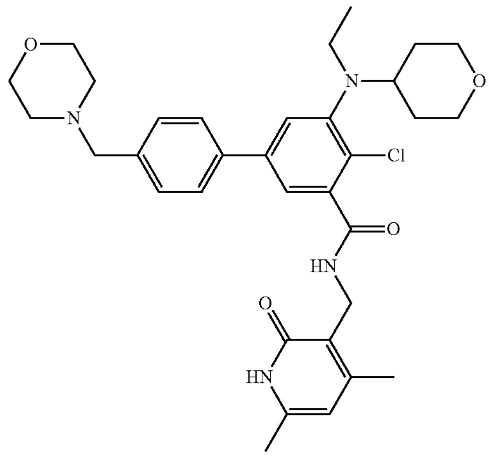 [SMILES: CCN(c1cc(-c2ccc(CN3CCOCC3)cc2)cc(C(=O)NCc2c(C)cc(C)[nH]c2=O)c1Cl)C1CCOCC1] | 593.60 |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono-or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahydrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —NH$_2$. "Alkylamino" includes groups of compounds wherein nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the disclosure may be depicted as different chiral isomers or geometric isomers. It should also be understood that when compounds have chiral isomeric or geometric isomeric forms, all isomeric forms are intended to be included in the scope of the disclosure, and the naming of the compounds does not exclude any isomeric forms.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerization is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

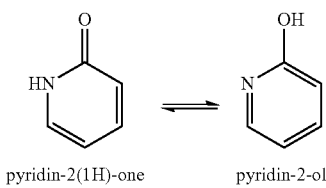 [SMILES: O=c1cccc[nH]1 ; Oc1ccccn1]

pyridin-2(1H)-one          pyridin-2-ol

It is to be understood that the compounds of the disclosure may be depicted as different tautomers. It should also be understood that when compounds have tautomeric forms, all tautomeric forms are intended to be included in the scope of the disclosure, and the naming of the compounds does not exclude any tautomer form.

The compounds of Formulae (I)-(VIa) disclosed herein include the compounds themselves, as well as their salts and their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. In the salt form, it is understood that the ratio of the compound to the cation or anion of the salt can be 1:1, or any ration other than 1:1, e.g., 3:1, 2:1, 1:2, or 1:3.

Additionally, the compounds of the disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Any compound of Formulae (I)-(VIa) of the disclosure, as described herein, may be an EZH2 inhibitor.

In certain aspects of the disclosure an inhibitor of EZH2 "selectively inhibits" histone methyltransferase activity of the mutant EZH2 when it inhibits histone methyltransferase activity of the mutant EZH2 more effectively than it inhibits histone methyltransferase activity of wild-type EZH2. For example, in one embodiment the selective inhibitor has an IC50 for the mutant EZH2 that is at least 40 percent lower than the IC50 for wild-type EZH2. In one embodiment the selective inhibitor has an IC50 for the mutant EZH2 that is at least 50 percent lower than the IC50 for wild-type EZH2. In one embodiment the selective inhibitor has an IC50 for the mutant EZH2 that is at least 60 percent lower than the IC50 for wild-type EZH2. In one embodiment the selective inhibitor has an IC50 for the mutant EZH2 that is at least 70 percent lower than the IC50 for wild-type EZH2. In one embodiment the selective inhibitor has an IC50 for the mutant EZH2 that is at least 80 percent lower than the IC50 for wild-type EZH2. In one embodiment the selective inhibitor has an IC50 for the mutant EZH2 that is at least 90 percent lower than the IC50 for wild-type EZH2.

In one embodiment, the selective inhibitor of a mutant EZH2 exerts essentially no inhibitory effect on wild-type EZH2.

In certain aspects of the disclosure the inhibitor (e.g. compound disclosed herein) inhibits conversion of H3-K27me2 to H3-K27me3. In one embodiment the inhibitor is said to inhibit trimethylation of H3-K27. Since conversion of H3-K27me1 to H3-K27me2 precedes conversion of H3-K27me2 to H3-K27me3, an inhibitor of conversion of H3-K27me1 to H3-K27me2 naturally also inhibits conversion of H3-K27me2 to H3-K27me3, i.e., it inhibits trimethylation of H3-K27. It is also possible to inhibit conversion of H3-K27me2 to H3-K27me3 without inhibition of conversion of H3-K27me1 to H3-K27me2. Inhibition of this type would also result in inhibition of trimethylation of H3-K27, albeit without inhibition of dimethylation of H3-K27.

In one embodiment the inhibitor (e.g. compound disclosed herein) inhibits conversion of H3-K27me1 to H3-K27me2 and the conversion of H3-K27me2 to H3-K27me3. Such inhibitor may directly inhibit the conversion of H3-K27me1 to H3-K27me2 alone. Alternatively, such inhibitor may directly inhibit both the conversion of H3-K27me1 to H3-K27me2 and the conversion of H3-K27me2 to H3-K27me3.

In certain aspects of the disclosure, the EZH2 inhibitor (e.g. compound disclosed herein) inhibits histone methyltransferase activity. Inhibition of histone methyltransferase activity can be detected using any suitable method. The inhibition can be measured, for example, either in terms of rate of histone methyltransferase activity or as product of histone methyltransferase activity.

The inhibition is a measurable inhibition compared to a suitable control. In one embodiment, inhibition is at least 10 percent inhibition compared to a suitable control. That is, the rate of enzymatic activity or the amount of product with the inhibitor is less than or equal to 90 percent of the corresponding rate or amount made without the inhibitor. In various other embodiments, inhibition is at least 20, 25, 30, 40, 50, 60, 70, 75, 80, 90, or 95 percent inhibition compared to a suitable control. In one embodiment, inhibition is at least 99 percent inhibition compared to a suitable control. That is, the rate of enzymatic activity or the amount of product with the inhibitor is less than or equal to 1 percent of the corresponding rate or amount made without the inhibitor.

A composition of the disclosure may comprise a compound of Formulae (I)-(VIa), or a pharmaceutically acceptable salt thereof, and one or more other therapeutic agents, or a pharmaceutically acceptable salt thereof. The disclosure provides for the administration of a compound of Formulae (I)-(VIa) or a pharmaceutically acceptable salt thereof, and one or more therapeutic agents or a pharmaceutically acceptable salt thereof, as a co-formulation or separate formulations, wherein the administration of formulations is simultaneous, sequential, or in alternation. In certain embodiments, the other therapeutic agents can be an agent that is recognized in the art as being useful to treat the disease or condition being treated by the composition of the disclosure. In other embodiment, the other therapeutic agent can be an agent that is not recognized in the art as being useful to treat the disease or condition being treated by the composition of the disclosure. In one aspect, the other therapeutic agents can be an agent that imparts a beneficial attribute to the composition of the disclosure (e.g., an agent that affects the viscosity of the composition). The beneficial attribute to the composition of the disclosure includes, but is not limited to, pharmacokinetic or pharmacodynamic co-action resulting from the combination of a compound of Formulae (I)-(VIa) and one or more other therapeutic agents.

The therapeutic agents set forth below are for illustrative purposes and not intended to be limiting. The disclosure includes at least one other therapeutic agent selected from the lists below. The disclosure can include more than one other therapeutic agent, e.g., two, three, four, or five other therapeutic agents such that the composition of the disclosure can perform its intended function.

In one embodiment, the other therapeutic agent is an anticancer agent. In one embodiment, the anticancer agent is a compound that affects histone modifications, such as an HDAC inhibitor. In certain embodiments, an anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren®, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Tykerb®, Velcade® and Zevalin™); corticosteroids, (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

In another embodiment, the other therapeutic agent is a chemotherapeutic agent (also referred to as an anti-neoplastic agent or anti-proliferative agent), selected from the group including an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0. asp.

Exemplary alkylating agents include, but are not limited to, cyclophosphamide (Cytoxan®; Neosar®); chlorambucil (Leukeran®); melphalan (Alkeran®); carmustine (BiCNU); busulfan (Busulfex®); lomustine (CeeNU®); dacarbazine (DTIC-Dome®); oxaliplatin (Eloxatin); carmustine (Gliadel®); ifosfamide (Ifex®); mechlorethamine (Mustargen); busulfan (Myleran); carboplatin (Paraplatin®); cisplatin (CDDP; Platinol®); temozolomide (Temodar®); thiotepa (Thioplex®); bendamustine (Treanda®); or streptozocin (Zanosar®).

Exemplary antibiotics include, but are not limited to, doxorubicin (Adriamycin®); doxorubicin liposomal (Doxil®); mitoxantrone (Novantrone®); bleomycin (Blenoxane®); daunorubicin (Cerubidine®); daunorubicin liposomal (DaunoXome®); dactinomycin (Cosmegen); epirubicin (Ellence®); idarubicin (Idamycin®); plicamycin (Mithracin®); mitomycin (Mutamycin); pentostatin (Nipent®); or valrubicin (Valstar®).

Exemplary anti-metabolites include, but are not limited to, fluorouracil (Adrucil®); capecitabine (Xeloda); hydroxyurea (Hydrea®); mercaptopurine (Purinethol®); pemetrexed (Alimta); fludarabine (Fludara); nelarabine (Arranon®); cladribine (Cladribine Novaplus®); clofarabine (Clolar®); cytarabine (Cytosar-U®); decitabine (Dacogen®); cytarabine liposomal (DepoCyt®); hydroxyurea (Droxia®); pralatrexate (Folotyn®); floxuridine (FUDR®); gemcitabine (Gemzar®); cladribine (Leustatin®); fludarabine (Oforta®); methotrexate (MTX®; Rheumatrex); methotrexate (Trexall®); thioguanine (Tabloid®); TS-1 or cytarabine (Tarabine PFS®).

Exemplary detoxifying agents include, but are not limited to, amifostine (Ethyol®) or mesna (Mesnex®).

Exemplary interferons include, but are not limited to, interferon alfa-2b (Intron A®) or interferon alfa-2a (Roferon-A®).

Exemplary polyclonal or monoclonal antibodies include, but are not limited to, trastuzumab (Herceptin®); ofatumumab (Arzerra®); bevacizumab (Avastin®); rituximab (Rituxan); cetuximab (Erbitux®); panitumumab (Vectibix®); tositumomaModine131 tositumomab (Bexxar®); alemtuzumab (Campath®); ibritumomab (Zevalin®; In-111®; Y-90® Zevalin®); gemtuzumab (Mylotarg®); eculizumab (Soliris®) ordenosumab.

Exemplary EGFR inhibitors include, but are not limited to, gefitinib (Iressa®); lapatinib (Tykerb®); cetuximab (Erbitux®); erlotinib (Tarceva®); panitumumab (Vectibix®); PKI-166; canertinib (CI-1033®); matuzumab (Emd7200®) or EKB-569.

Exemplary HER2 inhibitors include, but are not limited to, trastuzumab (Herceptin®); lapatinib (Tykerb®) or AC-480.

Histone Deacetylase Inhibitors include, but are not limited to, vorinostat (Zolinza®).

Exemplary hormones include, but are not limited to, tamoxifen (Soltamox®; Nolvadex®); raloxifene (Evista®); megestrol (Megace®); leuprolide (Lupron®; Lupron Depot®; Eligard®; Viadur®); fulvestrant (Faslodex®); letrozole (Femara®); triptorelin (Trelstar LA®; Trelstar Depot®); exemestane (Aromasin®); goserelin (Zoladex®); bicalutamide (Casodex®); anastrozole (Arimidex); fluoxymesterone (Androxy®; Halotestin®); medroxyprogesterone (Provera®; Depo-Provera®); estramustine (Emcyt®); flutamide (Eulexin®); toremifene (Fareston®); degarelix (Firmagon®); nilutamide (Nilandron®); abarelix (Plenaxis®); or testolactone (Teslac®).

Exemplary mitotic inhibitors include, but are not limited to, paclitaxel (Taxol®; Onxol®; Abraxane®); docetaxel (Taxotere®); vincristine (Oncovin®; Vincasar PFS®); vinblastine (Velban®); etoposide (Toposar®; Etopophos®; VePesid®); teniposide (Vumon®); ixabepilone (Ixempra®); nocodazole; epothilone; vinorelbine (Navelbine®); camptothecin (CPT); irinotecan (Camptosar®); topotecan (Hycamtin®); amsacrine or lamellarin D (LAM-D).

Exemplary MTOR inhibitors include, but are not limited to, everolimus (Afinitor®) or temsirolimus (Torisel®); rapamune, ridaforolimus; or AP23573.

Exemplary VEGF/VEGFR inhibitors include, but are not limited to, bevacizumab (Avastin®); sorafenib (Nexavar®); sunitinib (Sutent®); ranibizumab; pegaptanib; or vandetinib.

Exemplary microtubule targeting drugs include, but are not limited to, paclitaxel, docetaxel, vincristine, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen®); isotretinoin (Accutane®; Amnesteem®; Claravis®; Sotret®); tretinoin (Vesanoid®); azacitidine (Vidaza®); bortezomib (Velcade®) asparaginase (Elspar®); levamisole (Ergamisol®); mitotane (Lysodren®); procarbazine (Matulane); pegaspargase (Oncaspar®); denileukin diftitox (Ontak®); porfimer (Photofrin®); aldesleukin (Proleukin®); lenalidomide (Revlimid®); bexarotene (Targretin®); thalidomide (Thalomid®); temsirolimus (Torisel®); arsenic trioxide (Trisenox®); verteporfin (Visudyne®); mimosine (Leucenol®); (1M tegafur-0.4 M 5-chloro-2,4-dihydroxypyrimidine-1 M potassium oxonate), or lovastatin.

In another aspect, the other therapeutic agent is a chemotherapeutic agent or a cytokine such as G-CSF (granulocyte colony stimulating factor).

In yet another aspect, the other therapeutic agents can be standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In another aspect, the other therapeutic agents can be an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BMW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-ß, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Exemplary tyrosine kinase inhibitors include, but are not limited to, erlotinib (Tarceva®); gefitinib (Iressa®); imatinib (Gleevec®); sorafenib (Nexavar®); sunitinib (Sutent®); trastuzumab (Herceptin®); bevacizumab (Avastin®); rituximab (Rituxan®); lapatinib (Tykerb®); cetuximab (Erbitux®); panitumumab (Vectibix®); everolimus (Afinitor®); alemtuzumab (Campath®); gemtuzumab (Mylotarg®); temsirolimus (Torisel®); pazopanib (Votrient®); dasatinib (Sprycel®); nilotinib (Tasigna®); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

More examples of the other therapeutic agents suitable to be used in combination with compounds of Formulae (I)-(VIa) or a pharmaceutically acceptable salt thereof are disclosed in co-pending U.S. Application No. 61/992,881 filed May 13, 2014 and International Application No. PCT/US2014/069167 filed Dec. 8, 2014, the contents of each of which are incorporated herein by reference in their entireties.

The disclosure provides methods for combination therapy in which a composition comprising a compound of Formulae (I)-(VIa) or a pharmaceutically acceptable salt thereof, and one or more other therapeutic agents are administered to a subject in need for treatment of a disease or cancer. The combination therapy can also be administered to cancer cells to inhibit proliferation or induce cell death. In one aspect, a compound of Formulae (I)-(VIa) or a pharmaceutically acceptable salt thereof is administered subsequent to administration of the composition of the disclosure comprising a compound of Formulae (I)-(VIa) or a pharmaceutically acceptable salt thereof, and one or more other therapeutic agents. In one aspect, a compound of Formulae (I)-(VIa) or a pharmaceutically acceptable salt thereof is administered prior to administration of the composition of the disclosure comprising a compound of Formulae (I)-(VIa) or a pharmaceutically acceptable salt thereof, and one or more other therapeutic agents. In one aspect, a compound of Formulae (I)-(VIa) or a pharmaceutically acceptable salt thereof is administered subsequent to administration of one or more therapeutic agents, such that the other therapeutic agents are administered either in a single composition or in two or more compositions, e.g. administered simultaneously, sequentially, or in alternation. In one aspect, a compound of Formulae (I)-(VIa) or a pharmaceutically acceptable salt thereof is administered prior to administration of one or more therapeutic agents, such that the other therapeutic agents are administered either in a single composition or in two or more compositions, e.g. administered simultaneously, sequentially, or in alternation.

In certain embodiments, "combination therapy" is intended to embrace administration of these therapeutic agents in a sequential manner, wherein each therapeutic agent is administered at a different time, as well as administration of these therapeutic agents, or at least two of the therapeutic agents concurrently, or in a substantially simultaneous manner. Simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Therapeutic agents may also be administered in alternation.

In certain aspects of the disclosure, the combination therapies featured in the disclosure can result in a synergistic effect in the treatment of a disease or cancer. A "synergistic effect" is defined as where the efficacy of a combination of therapeutic agents is greater than the sum of the effects of any of the agents given alone. A synergistic effect may also be an effect that cannot be achieved by administration of any of the compounds or other therapeutic agents as single agents. The synergistic effect may include, but is not limited to, an effect of treating cancer by reducing tumor size, inhibiting tumor growth, or increasing survival of the subject. The synergistic effect may also include reducing cancer cell viability, inducing cancer cell death, and inhibiting or delaying cancer cell growth.

In certain aspects of the disclosure "combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In another aspect, a composition of the disclosure, or a pharmaceutically acceptable salt, solvate, analog or derivative thereof, may be administered in combination with radiation therapy. Radiation therapy can also be administered in combination with a composition of the disclosure and another chemotherapeutic agent described herein as part of a multiple agent therapy.

Combination therapy can be achieved by administering two or more agents, e.g., a compound of Formulae (I)-(VIa) and one or more other therapeutic agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The disclosure also provides pharmaceutical compositions comprising a compound of Formulae (I)-(VIa) or pharmaceutically acceptable salts thereof, and one or more other therapeutic agents disclosed herein, mixed with pharmaceutically suitable carriers or excipient(s) at doses to treat or prevent a disease or condition as described herein. In one aspect, the disclosure also provides pharmaceutical compositions comprising any compound of Table I or pharmaceutically acceptable salts thereof, and one or more therapeutic agents, mixed with pharmaceutically suitable carriers or excipient (s) at doses to treat or prevent a disease or condition as described herein. In another aspect, the disclosure also provides pharmaceutical compositions comprising Compound 44

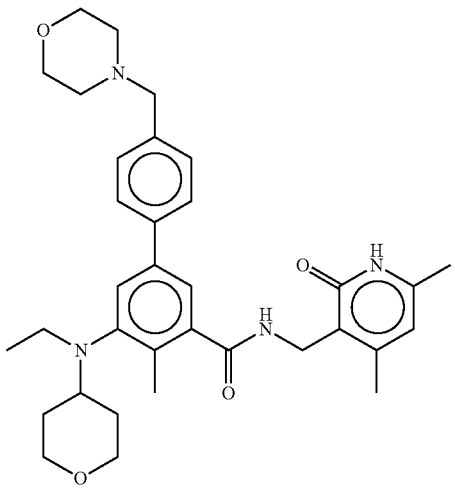

or pharmaceutically acceptable salts thereof, and one or more therapeutic agents, mixed with pharmaceutically suitable carriers or excipient(s) at doses to treat or prevent a disease or condition as described herein. The pharmaceutical compositions of the disclosure can also be administered in combination with other therapeutic agents or therapeutic modalities simultaneously, sequentially, or in alternation.

Mixtures of compositions of the disclosure can also be administered to the patient as a simple mixture or in suitable formulated pharmaceutical compositions. For example, one aspect of the disclosure relates to a pharmaceutical composition comprising a therapeutically effective dose of an EZH2 inhibitor of Formulae (I)-(VIa), or a pharmaceutically acceptable salt, hydrate, enantiomer or stereoisomer thereof; one or more other therapeutic agents, and a pharmaceutically acceptable diluent or carrier.

A "pharmaceutical composition" is a formulation containing the compounds of the disclosure in a form suitable for administration to a subject. A compound of Formulae (I)-(VIa) and one or more other therapeutic agents described herein each can be formulated individually or in multiple pharmaceutical compositions in any combinations of the active ingredients. Accordingly, one or more administration routes can be properly elected based on the dosage form of each pharmaceutical composition. Alternatively, a compound of Formulae (I)-(VIa) and one or more other therapeutic agents described herein can be formulated as one pharmaceutical composition.

In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition of the disclosure can be administered to a subject in many of the well-known methods currently used for chemotherapeutic treatment. For example, for treatment of cancers, a compound of the disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

In certain embodiments the therapeutically effective amount of each pharmaceutical agent used in combination will be lower when used in combination in comparison to monotherapy with each agent alone. Such lower therapeutically effective amount could afford for lower toxicity of the therapeutic regimen.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the EZH2 inhibitors described herein, other therapeutic agents described herein, compositions comprising a compound of Formulae (I)-(VIa) and one or more other therapeutic agents, or the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The composition of the disclosure is capable of further forming salts. The composition of the disclosure is capable of forming more than one salt per molecule, e.g., mono-, di-, tri-. All of these forms are also contemplated within the scope of the claimed disclosure.

As used herein, "pharmaceutically acceptable salts" refer to derivatives of the compounds of the disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), of the same salt.

The composition of the disclosure may also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The composition, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in Remington: the Science and Practice of Pharmacy, 19th edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the disclosure are apparent from the different examples. The provided examples illustrate different components and methodology useful in practicing the disclosure. The examples do not limit the claimed invention. Based on the present disclosure the skilled artisan can identify and employ other components and methodology useful for practicing the disclosure.

As used herein, a "subject in need thereof" is a subject having a disorder in which EZH2-mediated protein methylation plays a part, or a subject having an increased risk of developing such disorder relative to the population at large. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

The subject of the disclosure includes any human subject who has been diagnosed with, has symptoms of, or is at risk of developing a cancer or a precancerous condition. The subject of the disclosure includes any human subject expressing a mutant EZH2. For example, a mutant EZH2 comprises one or more mutations, wherein the mutation is a substitution, a point mutation, a nonsense mutation, a missense mutation, a deletion, or an insertion or any other EZH2 mutation described herein.

A subject in need thereof may have refractory or resistant cancer. "Refractory or resistant cancer" means cancer that does not respond to treatment. The cancer may be resistant at the beginning of treatment or it may become resistant during treatment. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy. In certain embodiments the prior therapy is monotherapy. In certain embodiments the prior therapy is combination therapy.

In some embodiments, a subject in need thereof may have a secondary cancer as a result of a previous therapy. "Secondary cancer" means cancer that arises due to or as a result from previous carcinogenic therapies, such as chemotherapy.

The subject may also exhibit resistance to EZH2 histone methyltransferase inhibitors or any other therapeutic agent.

As used herein, the term "responsiveness" is interchangeable with terms "responsive", "sensitive", and "sensitivity", and it is meant that a subject is showing therapeutic responses when administered a composition of the disclosure, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered a composition of the disclosure, e.g., tumor cells or tumor tissues of the subject undergo apoptosis and/or necrosis, and/or display reduced growing, dividing, or proliferation.

By "sample" it means any biological sample derived from the subject, includes but is not limited to, cells, tissues samples, body fluids (including, but not limited to, mucus, blood, plasma, serum, urine, saliva, and semen), tumor cells, and tumor tissues. Preferably, the sample is selected from bone marrow, peripheral blood cells, blood, plasma and serum. Samples can be provided by the subject under treatment or testing. Alternatively samples can be obtained by the physician according to routine practice in the art.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the disclosure, or a pharmaceutically acceptable salt or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the disclosure, or a pharmaceutically acceptable salt or solvate thereof. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "treating" or "treat" describes the management and care of a patient for the purpose of combating a disease, condition, or disorder and includes the administration of a compound of the disclosure, or a pharmaceutically acceptable salt or solvate thereof, to alleviate the symptoms or complications of a disease, condition or disorder, or to eliminate the disease, condition or disorder.

A composition of the disclosure, or a pharmaceutically acceptable salt or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/ nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer

A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the disclosure may be used to treat a cancer selected from the group consisting of a hematologic cancer of the disclosure or a hematologic cell proliferative disorder of the disclosure. A hematologic cancer of the disclosure can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the disclosure may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung to neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the disclosure may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, malignant growths or lesions of the prostate and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the disclosure may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the disclosure may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphocytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructural heterogeneity (e.g., mixed cell types).

Preferably, compound of the disclosure, or a pharmaceutically acceptable salt or solvate thereof, may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the disclosure, or a pharmaceutically acceptable salt or solvate thereof, may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

The disorder in which EZH2-mediated protein methylation plays a part can be a neurological disease. The compound of this disclosure can thus also be used for treating neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by EZH2, plays a role may be treatable or preventable using compositions and methods described herein.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the disclosure, or a pharmaceutically acceptable salt, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the disclosure, or a pharmaceutically acceptable salt, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement.

Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the disclosure, or a pharmaceutically acceptable salt or solvate thereof, acts selectively on a cancer or precancerous cell but not on a normal cell. Preferably, a compound of the disclosure, or a pharmaceutically acceptable salt or solvate thereof, acts selectively to modulate one molecular target (e.g., a target protein methyltransferase) but does not significantly modulate another molecular target (e.g., a non-target protein methyltransferase). The disclosure also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A composition of the disclosure, e.g., a composition comprising any compound of Formulae (I)-(VIa) or pharmaceutically acceptable salt thereof, and one or more other therapeutic agents, such as prednisone, can modulate the activity of a molecular target (e.g., a target protein methyltransferase). Modulating refers to stimulating or inhibiting an activity of a molecular target. Preferably, a compound of the disclosure, or a pharmaceutically acceptable salt or solvate thereof, modulates the activity of a molecular target if it stimulates or inhibits the activity of the molecular target by at least 2-fold relative to the activity of the molecular target under the same conditions but lacking only the presence of said compound. More preferably, a compound of the disclosure, or a pharmaceutically acceptable salt or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A composition of the disclosure does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the disclosure, or a pharmaceutically acceptable salt or solvate thereof, demonstrates a minimum of a fourfold differential, preferably a tenfold differential, more preferably a fifty fold differential, in the dosage required to achieve a biological effect. Preferably, a compound of the disclosure, or a pharmaceutically acceptable salt or solvate thereof, demonstrates this differential across the range of inhibition, and the differential is exemplified at the $IC_{50}$, i.e., a 50% inhibition, for a molecular target of interest.

Administering a composition of the disclosure to a cell or a subject in need thereof can result in modulation (i.e., stimulation or inhibition) of an activity of a protein methyltransferase of interest.

Administering a compound of the disclosure, e.g., a composition comprising any compound of Formulae (I)-(VIa) or pharmaceutically acceptable salt thereof, and one or more other therapeutic agents, such as prednisone, to a cell or a subject in need thereof results in modulation (i.e., stimulation or inhibition) of an activity of an intracellular target (e.g., substrate). Several intracellular targets can be modulated with the compounds of the disclosure, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a composition of the disclosure, or a pharmaceutically acceptable salt or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a composition of the disclosure, or a pharmaceutically acceptable salt or solvate thereof, can induce or activate cell death selectively in cancer cells. Administering to a subject in need thereof a compound of the disclosure, or a pharmaceutically acceptable salt or solvate thereof, can induce or activate cell death selectively in cancer cells. Contacting a cell with a composition of the disclosure, or a pharmaceutically acceptable salt or solvate thereof, can induce cell death selectively in one or more cells affected by a cell proliferative disorder. Preferably, administering to a subject in need thereof a composition of the disclosure, or a pharmaceutically acceptable salt or solvate thereof, induces cell death selectively in one or more cells affected by a cell proliferative disorder.

The disclosure relates to a method of treating or preventing cancer by administering a composition of the disclosure, or a pharmaceutically acceptable salt or solvate thereof, to a subject in need thereof, where administration of the composition of the disclosure, or a pharmaceutically acceptable salt or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, 18th edition (1990). These texts can, of course, also be referred to in making or using an aspect of the disclosure.

Example 1: EZH2 Breast Cancer In Vitro Combination Studies

Methods: Studies were performed using breast cancer cell lines in vitro to evaluate the anti-proliferative effect of combinations of tazemetostat and a second agent. Initial proliferation studies were performed to determine the $IC_{50}$ of tazemetostat in each cell line. For the screen, tazemetostat was used at concentrations bracketed around the $IC_{50}$ value. If 50% inhibitory concentration was not reached then tazemetostat was tested starting at 10 μM.

In order to study the effect of dual combination of tazemetostat and a second agent on cell proliferation, cells in log-linear phase growth rate were pre-treated with various concentrations of tazemetostat or DMSO for 7 days in flasks, plated in 384-well plates in the absence of compounds and co-treated on day 8 with tazemetostat or DMSO and the second agent serially diluted for additional 6 days (as depicted in FIG. 1). On day 14 plates were developed for endpoint analysis using Cell Titer Glo to measure ATP content, which was used as an indicator of cell viability. DMSO concentration was kept constant throughout the assay at 0.2% v/v.

Cell lines: The cell lines BT-549, DU4475, HCC1187, HCC1395, HCC1419, HCC1569, HCC1806, HCC1937, HCC1954, HCC202, HCC38, HCC70, MCF-7, MDA-MB-157, MDA-MB-175VII, MDA-MB-231, MDA-MB-361, MDA-MB-436, MDA-MB-453, MDA-MB-468, SK-BR-3 and ZR-75-1 were obtained from American Type Culture Collection (ATCC; Rockville, MD) and cultured in RPMI medium containing 10% v/v Fetal Bovine Serum (FBS) and 1% v/v Penicillin/Streptomycin (P/S). BT-20 and CAMA-1 cell lines were obtained from ATCC and cultured in EMEM containing 10% v/v FBS and 1% v/v P/S. The cell line BT-474 was obtained from ATCC and cultured in DMEM containing 10% FBS v/v and 1% v/v P/S. MDA-MB-361 from ATCC and cultured in RPMI medium containing 20% v/v FBS and 1% v/v P/S. The cell lines SUM149PT, SUM159PT, SUM52PE were obtained from Asterand Bioscience (Detroit, MI) and cultured in RPMI medium containing 10% v/v FBS and 1% P/S v/v. The cell line SUM1315M02 was obtained from Asterand Bioscience and cultured in RPMI medium containing 20% v/v FBS and 1% v/v P/S. All cells were maintained and cultured at 37° C. in a humidified atmosphere and 5% $CO_2$.

Analysis of Synergy: A combination of tazemetostat and a second agent was considered synergistic if the IC50 value IC50 value of the second agent decreased by 2-fold or more when tazemetostat was added as compared to the DMSO control and antagonistic if the IC50 value increased by 2-fold or more.

Example 2: EZH2 Ovarian Cancer In Vitro Combination Studies

Figure 2:
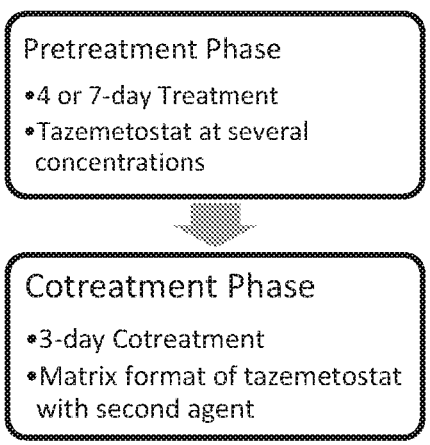
FIG. 2 is a schematic diagram depicting the experimental procedure of Example 2.
Figure 3:
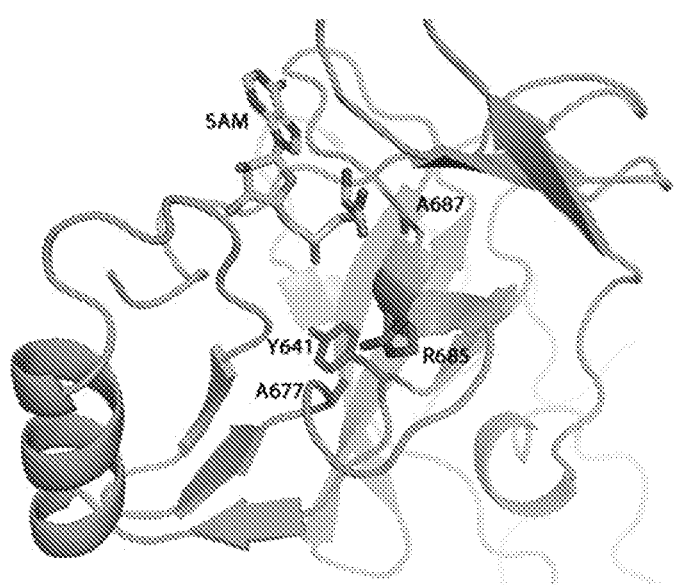
FIG. 3 is an illustration of the EZH2 protein structure.

Methods: Studies were performed using ovarian cancer cell lines in vitro to evaluate the anti-proliferative effect of combinations of tazemetostat and a second agent. Initial proliferation studies were performed to determine the $IC_{50}$ of tazemetostat in each cell line. In order to study the effect of dual combination of tazemetostat and a second agent on cell proliferation, cells in log-linear phase growth rate were pre-treated with various concentrations of tazemetostat starting at 10 μM or DMSO for 4 or 7 days (depending on the growth kinetics of the cell line), followed by co-treatment with tazemetostat or DMSO and the second agent serially diluted for additional 3 days (as depicted in FIG. 2). Plates were developed for endpoint analysis using Cell Titer Glo to measure ATP content, which was used as an indicator of cell viability. DMSO concentration was kept constant throughout the assay at 0.1% v/v. RMUG-S and COV644 were tested in a 7 day pre-treatment followed by co-treatment for 3 days (7+3 model) and the remaining cell lines were pre-treated for 4 days (4+3 model).

Cell lines: The cell lines CAOV-3, ES-2, OV-90, NIH:OVCAR-3, SKOV3, TOV112D, and TOV21G were obtained from American Type Culture Collection (ATCC; Rockville, MD). The cell lines A2780, COV434, COV504, and OAW42 were obtained from Sigma-Aldrich (St. Louis, MO). The cell line JHOS-4 was obtained from RIKEN BioResource Center (Japan). The cell lines KURAMOCHI, OVISE, OVMANA, OVSAHO, RMUG-S, and TYK-NU were obtained from Japanese Collection of Research Bioresources Cell Bank (JCRB; Japan). The cell lines COV362, COV644, and OV-7 were obtained from European Collection of Authenticated Cell Cultures (ECACC; United Kingdom). The cell line SNU-840 was obtained from the Korean Cell Line Bank (KCLB; Seoul, Korea). All cells were maintained as instructed by the supplier and cultures were maintained at 37° C. in a humidified atmosphere and 5% CO2.

Analysis of Synergy: A combination of tazemetostat and a second agent was considered synergistic if the $IC_{50}$ value of the second agent decreased by 2-fold or more when tazemetostat was added as compared to the DMSO control and antagonistic if it increased by 2-fold or more.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow. Where names of cell lines or genes are used, abbreviations and names conform to the nomenclature of the American Type Culture Collection (ATCC) or the National Center for Biotechnology Information (NCBI), unless otherwise noted or evident from the context.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating ovarian cancer or breast cancer comprising administering to a subject in need thereof
   (a) a therapeutically effective amount of Compound A:

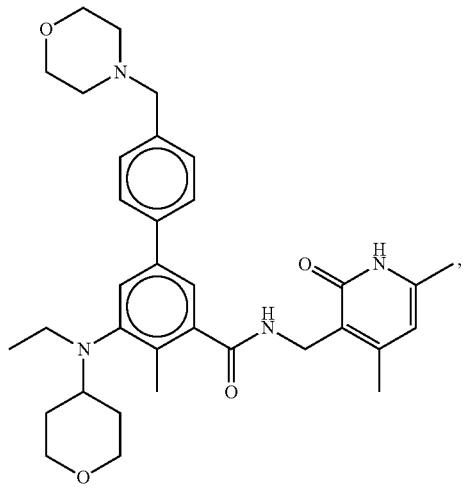

or a pharmaceutically acceptable salt thereof, and
   (b) a therapeutically effective amount of a PARP inhibitor selected from iniparib and olaparib.

2. The method of claim 1, wherein the therapeutically effective amount of Compound A, or a pharmaceutically acceptable salt thereof, is between about 100 mg and about 1600 mg per day, inclusive of the endpoints.

3. The method of claim 1, wherein the cancer is ovarian cancer.

4. The method of claim 1, wherein the cancer is breast cancer.

5. The method of claim 1, wherein Compound A, or a pharmaceutically acceptable salt thereof, and the PARP inhibitor are administered simultaneously.

6. The method of claim 1, wherein Compound A, or a pharmaceutically acceptable salt thereof, and the PARP inhibitor are administered sequentially.

7. The method of claim 6, wherein Compound A, or a pharmaceutically acceptable salt thereof, is administered prior to the PARP inhibitor.

8. The method of claim 6, wherein the PARP inhibitor is administered prior to Compound A, or a pharmaceutically acceptable salt thereof.

9. The method of claim 3, wherein the ovarian cancer is resistant or refractory to at least one prior monotherapy.

10. The method of claim 4, wherein the breast cancer is resistant or refractory to at least one prior monotherapy.

11. The method of claim 4, wherein the breast cancer is estrogen receptor (ER) negative, progesterone receptor (PR) negative, or HER2 negative.

12. The method of claim 4, wherein the breast cancer is ER negative, PR negative, and HER2 negative.

13. The method of claim 9, wherein the ovarian cancer is estrogen receptor (ER) negative, progesterone receptor (PR) negative, or HER2 negative.

14. The method of claim 9, wherein the ovarian cancer is ER negative, PR negative, and HER2 negative.

15. The method of claim 3, wherein the PARP inhibitor is olaparib.

16. The method of claim 4, wherein the PARP inhibitor is olaparib.

17. The method of claim 3, wherein the PARP inhibitor is iniparib.

18. The method of claim 4, wherein the PARP inhibitor is iniparib.

19. The method of claim 3, wherein Compound A, or a pharmaceutically acceptable salt thereof, and the PARP inhibitor are administered sequentially.

20. The method of claim 4, wherein Compound A, or a pharmaceutically acceptable salt thereof, and the PARP inhibitor are administered sequentially.

* * * * *